(12) United States Patent
Mattei et al.

(10) Patent No.: US 10,849,881 B2
(45) Date of Patent: Dec. 1, 2020

(54) OCTAHYDRO-CYCLOBUTA[1,2-C;3,4-C']DIPYRROL-2-YL

(71) Applicant: Hoffmann-La Roche Inc., Little Falls, NJ (US)

(72) Inventors: Patrizio Mattei, Riehen (CH); Daniel Hunziker, Moehlin (CH); Patrick Di Giorgio, Riehen (CH); Jerome Hert, Basel (CH); Markus Rudolph, Basel (CH); Lisha Wang, Basel (CH)

(73) Assignee: Hoffmann-La Roche Inc., Little Falls, NJ (US)

(*) Notice: Subject to any disclaimer, the term of this patent is extended or adjusted under 35 U.S.C. 154(b) by 0 days.

(21) Appl. No.: 15/997,341

(22) Filed: Jun. 4, 2018

(65) Prior Publication Data

US 2018/0280352 A1    Oct. 4, 2018

Related U.S. Application Data

(63) Continuation of application No. 15/164,122, filed on May 25, 2016, now abandoned, which is a continuation of application No. PCT/EP2014/075360, filed on Nov. 24, 2014.

(30) Foreign Application Priority Data

Nov. 26, 2013   (EP) .................................. 13194475

(51) Int. Cl.
  *A61K 31/407*    (2006.01)
  *C07D 209/56*    (2006.01)
  *C07D 487/04*    (2006.01)

(52) U.S. Cl.
  CPC .......... *A61K 31/407* (2013.01); *C07D 209/56* (2013.01); *C07D 487/04* (2013.01)

(58) Field of Classification Search
  CPC ... A61K 31/407; C07D 209/56; C07D 487/04
  USPC ....................................................... 514/411
  See application file for complete search history.

(56) References Cited

U.S. PATENT DOCUMENTS

| | | | |
|---|---|---|---|
| 3,392,149 A | 7/1968 | von der Emden et al. |
| 5,202,322 A | 4/1993 | Allen et al. |
| 5,238,942 A | 8/1993 | Chakravarty et al. |
| 5,240,928 A | 8/1993 | Allen et al. |
| 5,290,780 A | 3/1994 | Venkatesan |
| 5,304,565 A | 4/1994 | Morimoto et al. |
| 5,358,951 A | 10/1994 | Levin et al. |
| 5,472,961 A | 5/1995 | Gottschlich et al. |
| 5,470,975 A | 11/1995 | Atwal |
| 5,532,243 A | 7/1996 | Gilligan |
| 6,821,964 B2 | 11/2004 | Colon-Cruz et al. |
| 6,841,560 B2 | 1/2005 | Thompson et al. |
| 7,271,260 B2 | 9/2007 | Lee et al. |
| 8,329,907 B2 | 12/2012 | Schultz et al. |
| 8,440,694 B2 | 5/2013 | Turner et al. |
| 8,697,883 B2 | 4/2014 | Abouabdellah et al. |
| 8,841,324 B2 | 9/2014 | Staehle et al. |
| 8,946,264 B2 | 2/2015 | Shinozuka et al. |
| 9,029,387 B2 | 5/2015 | Staehle et al. |
| 9,493,486 B2 | 11/2016 | Hunziker et al. |
| 9,580,434 B2 | 2/2017 | Mazurov et al. |
| 9,598,418 B2 | 3/2017 | Srivastava et al. |
| 9,802,944 B2 | 10/2017 | Di Giorgio et al. |
| 10,208,052 B1 | 2/2019 | Zheng et al. |
| 10,633,384 B2 | 4/2020 | Hunziker et al. |
| 10,640,472 B2 | 5/2020 | Hert et al. |
| 10,647,719 B2 | 5/2020 | Di Giorgio et al. |
| 10,654,857 B2 | 5/2020 | Di Giorgio et al. |
| 10,669,268 B2 | 6/2020 | Hert et al. |
| 10,669,285 B2 | 6/2020 | Hunziker et al. |
| 10,676,446 B2 | 6/2020 | Hert et al. |
| 2005/0203112 A1 | 9/2005 | Castonguay et al. |
| 2008/0090802 A1 | 4/2008 | Letourneau et al. |
| 2010/0222341 A1 | 9/2010 | Schiemann et al. |
| 2010/0298290 A1 | 11/2010 | Anand et al. |
| 2011/0230471 A1 | 9/2011 | Staehle et al. |
| 2012/0015959 A1 | 1/2012 | Staehle et al. |
| 2012/0095040 A1 | 4/2012 | Abouabdellah et al. |
| 2012/0115852 A1 | 5/2012 | Schultz et al. |
| 2012/0115858 A1 | 5/2012 | Tesconi et al. |
| 2015/0252046 A1 | 9/2015 | Staehle et al. |
| 2015/0353559 A1 | 12/2015 | Hert et al. |
| 2015/0376194 A1 | 12/2015 | Hert et al. |
| 2016/0264586 A1 | 9/2016 | Mattei et al. |
| 2017/0008900 A1 | 1/2017 | Di Giorgio et al. |
| 2017/0008913 A1 | 1/2017 | Hunziker et al. |
| 2017/0029425 A1 | 2/2017 | Hunziker et al. |
| 2017/0050960 A1 | 2/2017 | Hert et al. |

(Continued)

FOREIGN PATENT DOCUMENTS

| | | | |
|---|---|---|---|
| CA | 2 768 095 | 1/2011 | |
| CA | 2768095 A1 * | 1/2011 | ........... C07D 487/04 |

(Continued)

OTHER PUBLICATIONS

Anderson, J Chemistry & Biology (2003), vol. 10, pp. 787-797. (Year: 2003).*

(Continued)

*Primary Examiner* — Craig D Ricci
*Assistant Examiner* — Janet L. Coppins
(74) *Attorney, Agent, or Firm* — Katherine J. Mackenzie

(57) ABSTRACT

The invention provides novel compounds having the general formula (I)

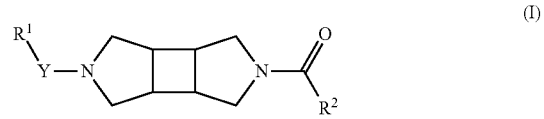

wherein $R^1$, Y and $R^2$ are as described herein, compositions including the compounds and methods of using the compounds.

20 Claims, No Drawings

(56) References Cited

U.S. PATENT DOCUMENTS

| | | |
|---|---|---|
| 2018/0208601 A1 | 7/2018 | Hert et al. |
| 2018/0208602 A1 | 7/2018 | Di Giorgio et al. |
| 2018/0258095 A1 | 9/2018 | Hert et al. |
| 2018/0280352 A1 | 10/2018 | Mattei et al. |
| 2018/0312515 A1 | 11/2018 | Mattei et al. |
| 2018/0327410 A1 | 11/2018 | Grice et al. |
| 2018/0327416 A1 | 11/2018 | Grice et al. |
| 2020/0002297 A1 | 1/2020 | Mattei et al. |
| 2020/0002336 A1 | 1/2020 | Hert et al. |
| 2020/0079779 A1 | 3/2020 | Di Giorgio et al. |
| 2020/0087307 A1 | 3/2020 | Mattei et al. |
| 2020/0199155 A1 | 6/2020 | Hunziker et al. |
| 2020/0207769 A1 | 7/2020 | Hunziker et al. |
| 2020/0216457 A1 | 7/2020 | Di Giorgio et al. |

FOREIGN PATENT DOCUMENTS

| | | |
|---|---|---|
| CA | 2878442 A1 | 4/2014 |
| CN | 1068114 A | 1/1993 |
| CN | 1751047 A1 | 3/2006 |
| CN | 102459207 A | 5/2012 |
| CN | 103237799 A | 8/2013 |
| CN | 104428299 A | 3/2015 |
| CN | 104918917 A | 9/2015 |
| EP | 0 417 631 A2 | 3/1991 |
| EP | 0 424 850 A1 | 5/1991 |
| EP | 2 301 936 A1 | 3/2011 |
| EP | 3 187 492 A1 | 7/2017 |
| EP | 3385261 A1 | 10/2018 |
| JP | 2001039950 | 2/2001 |
| JP | 2005-239708 | 9/2005 |
| JP | 2007-176809 | 7/2007 |
| JP | 2008-501743 | 1/2008 |
| JP | 2008-31064 | 2/2008 |
| JP | 2008-31064 A | 2/2008 |
| JP | 2008-531533 | 8/2008 |
| JP | 2008-540547 | 11/2008 |
| JP | 2009-161449 | 7/2009 |
| JP | 2011-502150 | 1/2011 |
| KR | 2006-0088557 | 8/2006 |
| RU | 2375352 C2 | 12/2009 |
| RU | 2 480 463 | 4/2013 |
| RU | 2 483 068 | 5/2013 |
| RU | 2 517 693 | 5/2014 |
| WO | 99/40070 | 8/1999 |
| WO | 01/30780 | 5/2001 |
| WO | 02/070523 A1 | 9/2002 |
| WO | 2004/074291 A1 | 9/2004 |
| WO | 2005/023762 A1 | 3/2005 |
| WO | 2005/040167 A1 | 5/2005 |
| WO | 2005/058798 A2 | 6/2005 |
| WO | 2005/084667 | 9/2005 |
| WO | 2005/121145 | 12/2005 |
| WO | 2006/015985 A1 | 2/2006 |
| WO | 2006/077035 A1 | 7/2006 |
| WO | 2006/090143 | 8/2006 |
| WO | 2006/122137 | 11/2006 |
| WO | 2007/030061 A1 | 3/2007 |
| WO | 2007/049771 | 5/2007 |
| WO | 2007/058322 | 5/2007 |
| WO | 2007/103719 | 9/2007 |
| WO | 2008/033456 A1 | 3/2008 |
| WO | 2008/033764 A2 | 3/2008 |
| WO | 2008/059026 A1 | 5/2008 |
| WO | 2008/060767 A2 | 5/2008 |
| WO | 2008/076223 A1 | 6/2008 |
| WO | 2008/116881 A1 | 10/2008 |
| WO | 2008/119662 A1 | 10/2008 |
| WO | 2008/126034 | 10/2008 |
| WO | 2008/135141 A1 | 11/2008 |
| WO | 2009/046841 A2 | 4/2009 |
| WO | 2009/054914 A1 | 4/2009 |
| WO | 2009/058347 | 5/2009 |
| WO | 2010/028761 | 3/2010 |
| WO | 2010/051977 | 5/2010 |
| WO | 2010/055006 A1 | 5/2010 |
| WO | 2010/060532 A1 | 6/2010 |
| WO | 2010/063352 A1 | 6/2010 |
| WO | 2010/099938 | 9/2010 |
| WO | 2010/108268 | 9/2010 |
| WO | 2010/108651 | 9/2010 |
| WO | 2010/112116 A1 | 10/2010 |
| WO | 2010/112124 A1 | 10/2010 |
| WO | 2010/115491 A2 | 10/2010 |
| WO | 2010/130944 A1 | 11/2010 |
| WO | 2010/135524 | 11/2010 |
| WO | 2010/141817 A1 | 12/2010 |
| WO | 2011/006569 A1 | 1/2011 |
| WO | 2011/017350 | 2/2011 |
| WO | 2011/017561 | 2/2011 |
| WO | 2011/053948 | 5/2011 |
| WO | 2011/085170 | 7/2011 |
| WO | 2011/114271 A1 | 9/2011 |
| WO | 2011/115813 A1 | 9/2011 |
| WO | 2011/116867 A1 | 9/2011 |
| WO | 2011/141716 A2 | 11/2011 |
| WO | 2009/154132 | 12/2011 |
| WO | 2011/151461 A2 | 12/2011 |
| WO | 2012/02008 | 2/2012 |
| WO | 2012/024620 | 2/2012 |
| WO | 2012/028243 | 3/2012 |
| WO | 2012/080727 | 6/2012 |
| WO | 2012/166415 | 12/2012 |
| WO | 2013/033059 A1 | 3/2013 |
| WO | 2013/054185 A1 | 4/2013 |
| WO | 2013/064467 A1 | 5/2013 |
| WO | 2013/065712 A1 | 5/2013 |
| WO | 2013/079223 A1 | 6/2013 |
| WO | 2013/175053 | 11/2013 |
| WO | 2013/186159 | 12/2013 |
| WO | 2014/007951 | 1/2014 |
| WO | 2014/018881 | 1/2014 |
| WO | 2014/018891 A1 | 1/2014 |
| WO | 2014/048865 A1 | 4/2014 |
| WO | 2014/048881 | 4/2014 |
| WO | 2014/055548 | 4/2014 |
| WO | 2014/066659 | 5/2014 |
| WO | 2014/102817 A1 | 7/2014 |
| WO | 2014/133112 A1 | 9/2014 |
| WO | 2014/139324 | 9/2014 |
| WO | 2014/139978 A1 | 9/2014 |
| WO | 2014/143579 | 9/2014 |
| WO | 2014/152725 A1 | 9/2014 |
| WO | 2014/164905 | 10/2014 |
| WO | 2015/008230 A1 | 1/2015 |
| WO | 2015/058031 | 4/2015 |
| WO | 2015/077503 A1 | 5/2015 |
| WO | 2015/078800 A1 | 6/2015 |
| WO | 2015/078803 | 6/2015 |
| WO | 2015/144480 A1 | 10/2015 |
| WO | 2015/144605 A1 | 10/2015 |
| WO | 2015/144609 A1 | 10/2015 |
| WO | 2015/144803 A1 | 10/2015 |
| WO | 2015/154023 A1 | 10/2015 |
| WO | 2016/031987 | 3/2016 |
| WO | 2016/061160 A1 | 4/2016 |
| WO | 2016/128529 A1 | 8/2016 |
| WO | 2016/162390 | 10/2016 |
| WO | 2017/005073 | 1/2017 |
| WO | 2017/037146 | 3/2017 |
| WO | 2017/037670 A1 | 3/2017 |
| WO | 2017/050732 | 3/2017 |
| WO | 2017/050747 | 3/2017 |
| WO | 2017/050791 | 3/2017 |
| WO | 2017/050792 | 3/2017 |
| WO | 2017/053722 A1 | 3/2017 |
| WO | 2017/091673 A2 | 6/2017 |
| WO | 2017/139978 A1 | 8/2017 |
| WO | 2018/167001 A1 | 9/2018 |
| WO | 2018/167113 | 9/2018 |

OTHER PUBLICATIONS

Matralis et al, Med Res Rev (2018), pp. 1-38. (Year: 2018).*

(56) References Cited

OTHER PUBLICATIONS

Thiel, Nature Biotechnology (2004), vol. 22 (5), pp. 513-519. (Year: 2004).*
Albers et al., "Structure-Based Design of a Novel Boronic Acid-Based Inhibitors of Autotaxin" Journal of Medicinal Chemistry 54(13):4619-4626 ( 2011).
Albers, H., et al., "Discovery and Optimization of Bornnic Add Based Inhibitors of Autotaxin" J. Med Chem 53:4958-4967 (Jun. 10, 2010).
Bora, Rajesh O., et al., "[1, 2, 4]-Oxadiazoles: Synthesis and Biological Applications" Mini-Reviews in Med. Chem 14(4):355-369 (Mar. 13, 2014).
CAS Registry Database, 959567-58-9, pp. 1-38 Dec. 26, 2007.
Erdik, Ender, "Transition Metal Catalyzed Reactions of Organozinc Reagents" Tetrahedron Report No. 23 48(44):9577-9648 (Jan. 1, 1992).
Farina, V. et al. Organic Reactions "The Stille Reaction" Paquette, Leo A., New York US: Wiley and Sons, vol. 50:1-704 (Apr. 1, 1997).
Green et al. Protective Groups in Organic Synthesis (Table of Contents only, in 4 pages), Second edition, New York:John Wiley & Sons, Inc., ( 1991).
Hall, Dennis, ed. et al. Boronic Acids: Preparation, Applications in Organic Synthesis and Medicine Hall, Dennis,Wiley, 571 pages (Jan. 1, 2006)—Description, Author information, and Table of Contents only.
Hemming, K. Science of Synthesis, Product 13: 1, 2, 3-Triazoles "Product Class 6: 1,2,4-Oxadiazoles" Storr, R.C. & Gilchrist, T.L., eds., Stuttgart-DE:Thieme Verlagsgruppe, vol. 13:127-184 (Jan. 1, 2004).
Henke, Brad R., et al., "Optimization of 3-(1H-Indazol-3-ylmethyl)-1,5-benzodiazepines as Potent, Orally Active CCK-A Agonists" J Med Chem 40:2706-2725 (Apr. 22, 1997).
ISR for PCT/EP2016/072277, 3 pages.
Li, Jie Jack et al. Name Reactions for Homologation, Part 1 "Name Reactions for Homologation, Part 1" (Abstract of text), Wiley and Sons;:1-685 (May 1, 2009)—Description, Author information, and Table of Contents only.
Mitchell, Terence N., "Palladium-Catalysed Reactions of Organotin Compounds" Synthesis 9:803-815 (Aug. 16, 1991).
Negishi, Ei-ichi, et al. Metal-Catalyzed Cross-Coupling Reactions "Chapter 1. Palladium or NickelCatalyzed CrossCoupling with Organometals Containing Zinc, Magnesium, Aluminum, and Zirconium" Diederich, Francois, Stang, Peter J., eds., Weinheim, DE:Wiley-VCH Verlag GmbH,:1-47 (Jan. 1, 2004)—Preface, Table of Contents, List of Contributors only.
Patani et al., "Bioisosterism: A Rational Approach in Drug Design," Chem.Rev. (1996), vol. 96, pp. 3147-3176.
Polshettiwar, Vivek, et al., "Suzuki-Miyaura Cross-Coupling Reactions in Aqueous Media: Green and Sustainable Syntheses of Biaryls" ChemSUSChem 3:502-522 (Jan. 1, 2010).
Pouliot, Marie-France, et al., "Synthesis of 1,3,4-oxadiazoles from 1,2-diacylhydrazines using [Et2NSF2]BF4 as a practical cyclodehydration agent" Org. Biomol. Chem 10:988-993, 2012.
Schlaeger, "The Protein Hydrolysate, Primatone RL, is a Cost-effective Multiple Growth Promoter of Mammalian Cell Cutlure in Serum-containing and Serum-free Media and Displays Anti-apoptosis Properties" J Immunol Methods 194:191-199 ( 1996).
Sheridan et al., "Cautious optimism surrounds early clinical data for PD-1 blocker" Nature Biotechnology 30:729-730 ( 2012).
Sheridan et al., "The Most Common Chemical Replacements in Drug-Like Compounds" J. Chem. Inf. Comput. Sci. 42(1):103-108 ( 2002).
Stille, John K., "The Palladium-Catalyzed Cross-Coupling Reactions of Organotin Reagents with Organic Electrophiles" Angew Chem. Int. Ed. Engl. 25:508-524 (Jan. 1, 1986).
Suzuki, A., et al., "Palladium-Catalyzed Cross-Coupling Reactions of Organoboron Compounds" Chem Rev. 95:2457-2483 (Jan. 31, 1995).
Suzuki, A., et al., "Recent advances in the cross-coupling reactions of organoboron derivatives with organic electrophiles, 1995-1998" J Organomet Chem 576:147-168 (Jan. 1, 1999).
Suzuki, A., et al., "Synthetic Studies via the cross-coupling reaction of oragnoboron derivatives with oragnic halides" Pure Appl Chem 63(3):419-422 (Jan. 1, 1991).
Tucker, Thomas J., et al., "Discovery of 3-{5-[(6-Amino-1H-pyrazolo[3,4-b]pyridine-3-yl)methoxy]-2-chlorophenoxy}-5-chlorobenzonitrile (MK-4965): A Potent, Orally Bioavailable HIV-1 Non-Nucleoside Reverse Transcriptase Inhibitor with Improved Potency against Key Mutant Viruses" J Med Chem 51:6503-6511 (Jul. 11, 2008).
WO:ISR, pp. 1-6 (International Search Report—PCT/EP2016/070561 dated Oct. 23, 2016 dated Oct. 12, 2016).
Pp. 1-13 (STN Columbus (STN International) Oct. 9, 2015).
1206969-43-8,Database Registry [retrieved online May 25, 2016] Chemical Abstracts Service, Feb. 22, 2010 (Feb. 22, 2010), BroadPharm: XP002707619, retrieved from STN Database accession No. 1206969-43-8 the whole document.
959567-58-9,Database Registry [retrieved online May 25, 2016] Chemical Abstracts Service Dec. 26, 2007 (Dec. 26, 2007), NIH Chemical Genomics Center: XP002707620, retrieved from STN Database accession No. 959567-58-9.
Albers et al., "Chemical Evolution of Autotaxin Hinhibitors" Chem Rev 112(5):2593-2603 (May 9, 2012).
Albers et al., "Chemical Evolution of Autotaxin Inhibitors" Chemical Reviews (XP055073234), 112(5):2593-2603 (May 9, 2012).
Barbayianni et al., "Autotaxin inhibitors: a patent review" Expert Opin Ther Patents 23(9):1123-1132 ( 2013).
Benesh et al., Febs Lett 588:2712-2727 ( 2014)
CAS Registry Database, 1300725-30-7,Database Registry [retrieved online May 25, 2016] Chemical Abstracts Service May 25, 2011 (May 25, 2011), Focus Synthesis. LLC: XP002707618, retrieved from STN Database accession No. 1300725-30-7 the whole document.
CAS Registry Database, 1352926-14-7,Database Registry [retrieved online May 25, 2016] Chemical Abstracts Service Jan. 12, 2012 (Jan. 12. 2012), All i chern LLC: XP002707617, retrieved from STN Database accession No. 1352926-14-7 see also RN: 135295-74-6; the whole document.
Database Capulus (online) Chemical Abstracts Service Columbus Ohio, 1993, Database accession No. 1994:483155 RN156411-73-3, 156411-74-4 (1993).
Garcia-Gutierrez et al., "Novel inhibitors to Taenia solium Cu/Zn superoxide dismutase identifed by virtual screening" J. Computer. Aided Molecular Design 25:1135-1145 ( 2011).
Gierse et al., "A Novel Autotaxin Inhibitor Reduces Lysophosphatidic Acid Levels in Plasma and the Site of Inflammation" Pharmacol Exp Ther 334:310-317 ( 2010).
Harald M.H.G. Albers et al., "Discovery and Optimization of Boronic Acid Based Inhibitors of Autotaxin" Journal of Medicinal Chemistry 53(13):4958-4967 (Jul. 8, 2010).
Hoeglund et al., "Optimization of a pidemidic acid autotaxin inhibitor" Journal of Medicinal Chemistry 53:1056-1066 (Dec. 30, 2009).
International Search Report for International Patent Application No. PCT/EP2014/075360.
ISR for PCT/EP2013/061890.
ISR for PCT/EP2013/069679.
Jones et al., ACS Med Chem Lett 7:857-861 ( 2016).
Kung et al., "Identification of spirocyclic piperidine-azetidine inverse agonists of the ghrelin receptor" Bioorganic & Medicinal Chemistry Letters (XP028490993), 22(13):4281-4287 (May 8, 2012).
Litherland et al., "The Amino-derivatives of Pentuerythritol. Part I. Preparation." (Published on Jan. 1, 1938. Downloaded by Roche Group on May 24, 2016 17:23:15.),:1588-1595.
Mayo Clinic Staff, (Lupus[online], retrieved from the internet on Jan. 24, 2017; http://www.mayoclinic.org/diseases-conditions-lupus basics/definition/CON-20019676) 2017.
Orr et al., "One-pot synthesis of chiral azetidines from chloroaldehyde and chiral amines" Tetrahedron Letters (XP055073241), 52:3618-3620 ( 2011).

(56) References Cited

OTHER PUBLICATIONS

Overberger et al., "Absolute Configuration of 2,7-Diazaspiro[4.4]nonane. A Reassignment" J. Org. Chem. (XP055072840), 46:2757-2764 ( 1981).
Sippy et al., "Preparation and characterization of N-(3-pyridinyl) spirocylic diamines as ligands for nicotinic acetylcholine receptors" Bioorganic & Medicinal Chemistry Letters 19:1682-1685 ( 2009).
Stocks et al., "A Practical Method for Targeted Library Design Balancing Lead-like Properties with Diversity" Chem Med Chem (XP002707616), 4:800-808 ( 2009).
Written Opinion for PCT/EP2013/061890.
Written Opinion for PCT/EP2013/069679.
Anderson, "The Process of Structure-Based Drug Design" Chemistry & Biology 10:787-797 (Sep. 2003).
Angeli et al., "Synthesis and carbonic anhydrase inhibition of polycyclic imides moieties" Bioorgan Med Chem 25(20):5373-5379 (Oct. 20, 2017).
Armstrong, J., et al., "Purification and Properties of Human Erythrocyte Carbonic Anhydrases" J Biol Chem 241(21):5137-5149 (Nov. 10, 1966).
"International Preliminary Report on Patentability—PCT/EP2018/056140":pp. 1-8 (dated Sep. 26, 2019).
"International Search Report—PCT/EP2014/054631":pp. 1-4 (dated Apr. 15, 2014).
"International Search Report—PCT/EP2015/056041":pp. 1-5 (dated May 6, 2015).
"International Search Report—PCT/EP2016/072349":pp. 1-5 (dated Nov. 29, 2016).
"International Search Report—PCT/EP2018/056140":pp. 1-9 (dated May 4, 2018).
"International Search Report—PCT/EP2018/056324" (x-cite P33952),:pp. 1-7 (dated May 8, 2018).
"International Search Report—PCT/EP2015/056032" (x-cite; P32055),:pp. 1-5 (dated Apr. 23, 2015).
"International Search Report—PCT/EP2016/057549":pp. 1-5 (dated Jun. 22, 2016).
"International Search Report—PCT/EP2016/072243":pp. 1-5 (dated Dec. 6, 2016).
"International Search Report—PCT/EP2016/072347":pp. 1-5 (dated Jan. 17, 2017).
"International Search Report—PCT/EP2016/070561":pp. 1-6 (dated Oct. 28, 2016).
Matralis et al., "Development and therapeutic potential of autotaxin small molecule inhibitors: From bench to advanced clinical trials" Med. Res. Rev.:1-38 ( 2018).
Thiel,, "Structure-aided drug design's next generation" Nat Biotechnol 22(5):513-519 (May 1, 2004).
Liu, Medicinal Chemistry (English translation),:349 (Aug. 31, 2007).
Tan, Pharmacology (English translation),:27-28 (Jul. 31, 2006).
"U.S. Appl. No. 16/793,178, filed Feb. 18, 2020".
"U.S. Appl. No. 16/811,656, filed Mar. 6, 2020".
"U.S. Appl. No. 16/818,409, filed Mar. 13, 2020".
"U.S. Appl. No. 16/832,553, filed Mar. 27, 2020".
"U.S. Appl. No. 16/889,322, filed Jun. 1, 2020".

* cited by examiner

OCTAHYDRO-CYCLOBUTA[1,2-C;3,4-C'] DIPYRROL-2-YL

RELATED APPLICATION DATA

This application is a Continuation of U.S. application Ser. No. 15/164,122, filed May 25, 2016, which is a Continuation of International Application No. PCT/EP2014/075360 filed on Nov. 24, 2014, which claims priority to EP Application No. 13194475.3 filed on Nov. 26, 2013, the disclosures of which are incorporated herein by reference in their entirety.

The present invention relates to organic compounds useful for therapy or prophylaxis in a mammal, and in particular to autotaxin (ATX) inhibitors which are inhibitors of lysophosphatidic acid (LPA) production and thus modulators of LPA levels and associated signaling, for the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection.

The present invention provides novel compounds of formula (I)

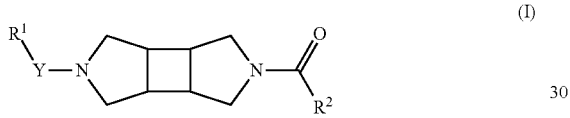

(I)

wherein $R^1$ is substituted quinolinyl, substituted 1,2,3,4-tetrahydroquinolinyl, substituted isoquinolinyl, substituted 1,2,3,4-tetrahydroisoquinolinyl, substituted 9H-carbazolyl, substituted chromanyl, substituted indolyl, substituted naphthyl, substituted oxazolyl, substituted phenyl, substituted phenylalkyl, substituted phenylcycloalkyl, substituted phenoxyalkyl, substituted phenylalkoxy, substituted phenylalkenyl, substituted phenylalkynyl, substituted pyridazinyl, substituted pyridazinylalkyl, substituted pyridazinylalkenyl, substituted pyridazinylalkynyl, substituted pyridinyl, substituted pyridinylalkyl, substituted pyridinylalkenyl, substituted pyridinylalkynyl, substituted pyridinonyl, substituted pyridinonylalkyl, substituted pyridinonylalkenyl, substituted pyridinonylalkynyl, substituted thiophenyl, substituted thiophenylalkyl, substituted thiophenylalkenyl, substituted thiophenylalkynyl, substituted tetralinyl or substituted tetralinonyl, wherein substituted quinolinyl, substituted 1,2,3,4-tetrahydroquinolinyl, substituted isoquinolinyl, substituted 1,2,3,4-tetrahydroisoquinolinyl, substituted 9H-carbazolyl, substituted chromanyl, substituted indolyl, substituted naphthyl, substituted oxazolyl, substituted phenyl, substituted phenylalkyl, substituted phenylcycloalkyl, substituted phenoxyalkyl, substituted phenylalkoxy, substituted phenylalkenyl, substituted phenylalkynyl, substituted pyridazinyl, substituted pyridazinylalkyl, substituted pyridazinylalkenyl, substituted pyridazinylalkynyl, substituted pyridinyl, substituted pyridinylalkyl, substituted pyridinylalkenyl, substituted pyridinylalkynyl, substituted pyridinonyl, substituted pyridinonylalkyl, substituted pyridinonylalkenyl, substituted pyridinonylalkynyl, substituted thiophenyl, substituted thiophenylalkyl, substituted thiophenylalkenyl, substituted thiophenylalkynyl, substituted tetralinyl and substituted tetralinonyl are substituted with $R^6$, $R^7$ and $R^8$;

Y is —C(O)— or —S(O)$_2$—;

$R^2$ is substituted pyridinyl, substituted phenyl or is selected from the ring systems A, B and C, wherein substituted pyridinyl and substituted phenyl are substituted with one substituted aminosulfonyl, wherein substituted aminosulfonyl is substituted on the nitrogen atom with one to two substituents independently selected from H, alkyl, cycloalkyl, cycloalkylalkyl, hydroxyalkyl and alkoxyalkyl;

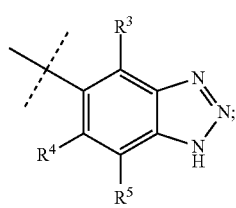

A

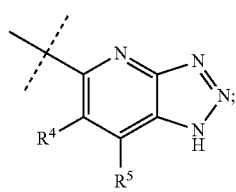

B

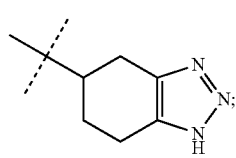

C $R^3$, $R^4$ and $R^5$ are independently selected from H, alkyl, halogen, haloalkyl and alkoxy;

$R^6$, $R^7$ and $R^8$ are independently selected from H, halogen, cyano, cyanoalkyl, alkyl, hydroxyalkyl, haloalkyl, hydroxyhaloalkyl, cycloalkyl, cycloalkylalkyl, cycloalkylalkoxy, cycloalkoxy, cycloalkoxyalkyl, cycloalkylalkoxyalkyl, alkoxy, alkoxyalkyl, haloalkoxy, alkoxyhaloalkyl, alkoxyalkoxy, alkoxyalkoxyalkyl, alkylsulfonyl, furanyl, tetrahydropyranyl, phenyl, substituted phenyl, phenylalkoxy, substituted phenylalkoxy, pyridinyl, substituted pyridinyl, pyrrolyl, substituted pyrrolyl, pyrrolydinyl and substituted pyrrolydinyl, wherein substituted phenyl, substituted phenylalkoxy, substituted pyridinyl, substituted pyrrolyl and substituted pyrrolydinyl are substituted with one to three halogen;

and pharmaceutically acceptable salts.

Autotaxin (ATX) is a secreted enzyme also called ectonucleotide pyrophosphatase/phosphodiesterase 2 or lysophospholipase D, which is important for converting lysophosphatidyl choline (LPC) to the bioactive signaling molecule lysophosphatidic acid (LPA). It has been shown that plasma LPA levels are well correlated with ATX activity and hence ATX is believed to be an important source of extracellular LPA. Early experiments with a prototype ATX inhibitor have shown that such a compound is able to inhibit the LPA synthesizing activity in mouse plasma. Work conducted in the 1970s and early 1980s has demonstrated that LPA can elicit a wide range of cellular responses; including smooth muscle cell contraction, platelet activation, cell proliferation, chemotaxis and others. LPA mediates its effects via signaling to several G protein coupled receptors (GPCRs); the first members were originally denoted Edg (endothelial cell differentiation gene) receptors or ventricular zone gene-1 (vzg-1) but are now called LPA receptors. The prototypic group now consists of LPA1/Edg-2/VZG-1, LPA2/Edg-4, and LPA3/Edg-7. Recently, three additional LPA receptors LPA4/p2y9/GPR23, LPA5/GPR92 and LPA6/p2Y5 have been described that are more closely related to nucleotide-selective purinergic receptors than to the prototypic LPA1-3 receptors. The ATX-LPA signaling axis is involved in a large range of physiological and pathophysiological functions, including, for example, nervous system function, vascular development, cardiovascular physiology, reproduction, immune system function, chronic inflammation, tumor metastasis and progression, organ fibrosis as well as obesity and/or other metabolic diseases such as diabetes mellitus. Therefore, increased activity of ATX and/or increased levels of LPA, altered LPA receptor expression and altered responses to LPA may contribute to the initiation, progression and/or outcome of a number of different pathophysiological conditions related to the ATX/LPA axis.

In accordance with the invention, the compounds of formula (I) or their pharmaceutically acceptable salts and esters can be used for the treatment or prophylaxis of diseases, disorders or conditions that are associated with the activity of autotaxin and/or the biological activity of lysophosphatidic acid (LPA).

The compounds of formula (I) or their pharmaceutically acceptable salts and esters herein inhibit autotaxin activity and therefore inhibit LPA production and modulate LPA levels and associated signaling. Autotaxin inhibitors described herein are useful as agents for the treatment or prevention of diseases or conditions in which ATX activity and/or LPA signaling participates, is involved in the etiology or pathology of the disease, or is otherwise associated with at least one symptom of the disease. The ATX-LPA axis has been implicated for example in angiogenesis, chronic inflammation, autoimmune diseases, fibrotic diseases, cancer and tumor metastasis and progression, ocular conditions, metabolic conditions such as obesity and/or diabetes mellitus, conditions such as cholestatic or other forms of chronic pruritus as well as acute and chronic organ transplant rejection.

Objects of the present invention are the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of disorders or conditions that are associated with the activity of ATX and/or the biological activity of lysophatidic acid (LPA), particularly in the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection, and the use of the said compounds, salts or esters for the production of medicaments for the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection.

The term "alkenyl" denotes a monovalent linear or branched hydrocarbon group of 2 to 7 carbon atoms with at least one double bond. In particular embodiments, alkenyl has 2 to 4 carbon atoms with at least one double bond. Examples of alkenyl include ethenyl, propenyl, prop-2-enyl, isopropenyl, n-butenyl and iso-butenyl. Particular alkenyl group is ethenyl.

The term "alkoxy" denotes a group of the formula —O—R', wherein R' is an alkyl group. Examples of alkoxy group include methoxy, ethoxy, n-propoxy, isopropoxy, n-butoxy, isobutoxy and tert-butoxy. Particular alkoxy group include methoxy, ethoxy and isopropoxy. More particular alkoxy group is isopropoxy.

The term "alkoxyalkoxy" denotes an alkoxy group wherein at least one of the hydrogen atoms of the alkoxy group has been replaced by another alkoxy group. Examples of alkoxyalkoxy group include methoxymethoxy, ethoxymethoxy, methoxyethoxy, ethoxyethoxy, methoxypropoxy and ethoxypropoxy. Particular alkoxyalkoxy group is methoxyethoxy.

The term "alkoxyalkoxyalkyl" denotes an alkyl group wherein at least one of the hydrogen atoms of the alkyl group has been replaced by an alkoxyalkoxy group. Examples of alkoxyalkoxyalkyl group include methoxymethoxymethyl, ethoxymethoxymethyl, methoxyethoxymethyl, ethoxyethoxymethyl, methoxypropoxymethyl, ethoxypropoxymethyl, methoxymethoxyethyl, ethoxymethoxyethyl, methoxyethoxyethyl, ethoxyethoxyethyl, methoxypropoxyethyl and ethoxypropoxyethyl.

The term "alkoxyalkyl" denotes an alkyl group wherein at least one of the hydrogen atoms of the alkyl group has been replaced by an alkoxy group. Exemplary alkoxyalkyl groups include methoxymethyl, ethoxymethyl, methoxyethyl, ethoxyethyl, methoxypropyl, ethoxypropyl and isopropoxymethyl. Particular alkoxyalkyl group is methoxpropyl.

The term "alkoxyhaloalkyl" denotes a haloalkyl group wherein at least one of the hydrogen atoms of the haloalkyl group has been replaced by an alkoxy group. Exemplary alkoxyalkyl groups include methoxytrifluoroethyl, ethoxytrifluoroethyl, methoxytrifluoropropyl and ethoxytrifluoropropyl.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl and sec-butyl, pentyl. Particular alkyl groups include methyl, isopropyl and iso-butyl.

The term "alkylsulfonyl" denotes a group of the formula —S(O)$_2$—R', wherein R' is an alkyl group. Examples of alkylsulfonyl groups include groups of the formula —S(O)$_2$—R' wherein R' is methyl, ethyl, n-propyl, isopropyl, n-butyl, isobutyl or tert-butyl. Particular alkylsulfonyl groups include group of the formula —S(O)$_2$—R', wherein R' is methyl.

The term "amino" denotes a —NH$_2$ group.

The term "aminosulfonyl" denotes a —S(O)$_2$—NH$_2$ group.

The term "cyano" denotes a —C≡N group.

The term "cyanoalkyl" denotes an alkyl group wherein one of the hydrogen atoms of the alkyl group has been replaced by a cyano group. Exemplary cyanoalkyl groups include cyanomethyl, cyanoethyl and cyanopropyl. Particular alkoxyalkyl group is cyanomethyl.

The term "cycloalkoxy" denotes a group of the formula —O—R', wherein R' is a cycloalkyl group. Examples of cycloalkoxy group include cyclopropoxy, cyclobutoxy, cyclopentyloxy, cyclohexyloxy, cycloheptyloxy and cyclooctyloxy. Particular cycloalkoxy group is cyclopropoxy.

The term "cycloalkoxyalkyl" denotes an alkyl group wherein at least one of the hydrogen atoms of the alkyl group has been replaced by a cycloalkoxy group. Examples of cycloalkoxyalkyl groups include cyclopropoxymethyl, cyclopropoxyethyl, cyclobutoxymethyl, cyclobutoxyethyl, cyclopentyloxymethyl, cyclopentyloxyethyl, cyclohexyloxymethyl, cyclohexyloxyethyl, cycloheptyloxymethyl, cycloheptyloxyethyl, cyclooctyloxymethyl and cyclooctyloxyethyl.

The term "cycloalkyl" denotes a monovalent saturated monocyclic or bicyclic hydrocarbon group of 3 to 10 ring carbon atoms. In particular embodiments, cycloalkyl denotes a monovalent saturated monocyclic hydrocarbon group of 3 to 8 ring carbon atoms. Bicyclic means a ring system consisting of two saturated carbocycles having two carbon atoms in common. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl or bicyclo[2.2.2]octanyl. Particular monocyclic cycloalkyl groups are cyclopropyl, cyclobutanyl, cyclopentyl and cyclohexyl. More particular monocyclic cycloalkyl group is cyclopropyl.

The term "cycloalkylalkoxy" denotes an alkoxy group wherein at least one of the hydrogen atoms of the alkoxy group is replaced by a cycloalkyl group. Examples of cycloalkylalkoxy include cyclopropylmethoxy, cyclobutylmethoxy, cyclopentylmethoxy, cyclohexylmethoxy, cycloheptylmethoxy and cyclooctylmethoxy. Particular cycloalkylalkoxy group is cyclopropylmethoxy.

The term "cycloalkylalkoxyalkyl" denotes an alkyl group wherein at least one of the hydrogen atoms of the alkyl group is replaced by a cycloalkylalkoxy group. Examples of cycloalkylalkoxyalkyl include cyclopropylmethoxymethyl, cyclopropylmethoxyethyl, cyclobutylmethoxymethyl, cyclobutylmethoxyethyl, cyclopentylmethoxyethyl, cyclopentylmethoxyethyl, cyclohexylmethoxymethyl, cyclohexylmethoxyethyl, cycloheptylmethoxymethyl, cycloheptylmethoxyethyl, cyclooctylmethoxymethyl and cyclooctylmethoxyethyl.

The term "cycloalkylalkyl" denotes an alkyl group wherein at least one of the hydrogen atoms of the alkyl group is replaced by a cycloalkyl group. Examples of cycloalkylalkyl include cyclopropylmethyl, cyclopropylethyl, cyclopropylbutyl, cyclobutylpropyl, 2-cyclopropylbutyl, cyclopentylbutyl, cyclohexylmethyl, cyclohexylethyl, bicyclo[4.1.0]heptanylmethyl, bicyclo[4.1.0]heptanylethyl, bicyclo[2.2.2]octanylmethyl, bicyclo[2.2.2]octanylethyl, adamantanylmethyl and adamantanylethyl. Particular examples of cycloalkylalkyl are cyclohexylmethyl, cyclohexylethyl, bicyclo[4.1.0]heptanylmethyl, bicyclo[4.1.0]heptanylethyl, bicyclo[2.2.2]octanylmethyl, bicyclo[2.2.2]octanylethyl, adamantanylmethyl and adamantanylethyl. Further particular examples cycloalkylalkyl are cyclohexylmethyl, cyclohexylethyl, bicyclo[4.1.0]heptanylmethyl, bicyclo[2.2.2]octanylmethyl, adamantanylmethyl and adamantanylethyl.

The term "haloalkoxy" denotes an alkoxy group wherein at least one of the hydrogen atoms of the alkoxy group has been replaced by the same or different halogen atoms. The term "perhaloalkoxy" denotes an alkoxy group where all hydrogen atoms of the alkoxy group have been replaced by the same or different halogen atoms. Examples of haloalkoxy include fluoromethoxy, difluoromethoxy, trifluoromethoxy, trifluoroethoxy, trifluoromethylethoxy, trifluorodimethylethoxy and pentafluoroethoxy. Particular haloalkoxy group are trifluoromethoxy and trifluoroethoxy.

The term "haloalkyl" denotes an alkyl group wherein at least one of the hydrogen atoms of the alkyl group has been replaced by the same or different halogen atoms. The term "perhaloalkyl" denotes an alkyl group where all hydrogen atoms of the alkyl group have been replaced by the same or different halogen atoms. Examples of haloalkyl include fluoromethyl, difluoromethyl, trifluoromethyl, trifluoroethyl, trifluoromethylethyl and pentafluoroethyl. Particular haloalkyl groups are trifluoromethyl and trifluoroethyl.

The term "halogen" and "halo" are used interchangeably herein and denote fluoro, chloro, bromo, or iodo. Particular halogens are chloro and fluoro. More particular halogen is chloro.

The term "hydroxy" denotes a —OH group.

The term "hydroxyalkyl" denotes an alkyl group wherein at least one of the hydrogen atoms of the alkyl group has been replaced by a hydroxy group. Examples of hydroxyalkyl include hydroxymethyl, hydroxyethyl, hydroxy-1-methyl-ethyl, hydroxypropyl, hydroxymethylpropyl and dihydroxypropyl. Particular examples are hydroxymethyl and hydroxyethyl.

The term "hydroxyhaloalkyl" denotes a haloalkyl group wherein at least one of the hydrogen atoms of the haloalkyl group has been replaced by an hydroxy group. Exemplary hydroxyhaloalkyl groups include hydroxytrifluoroethyl and hydroxytrifluoropropyl. Particular hydroxyhaloalkyl groups include hydroxytrifluoroethyl.

The term "phenoxy" denotes a group of the formula —O—R', wherein R' is a phenyl.

The term "phenoxyalkyl" denotes an alkyl group wherein at least one of the hydrogen atoms of the alkyl group has been replaced by a phenoxy group. Exemplary phenoxyalkyl groups include phenoxymethyl, phenoxyethyl and phenoxypropyl. Particular alkoxyalkyl group is phenoxymethyl.

The term "phenylalkenyl" denotes an alkenyl group wherein at least one of the hydrogen atoms of the alkenyl group has been replaced a phenyl. Particular phenylalkenyl group is phenylethenyl.

The term "phenylalkoxy" denotes an alkoxy group wherein at least one of the hydrogen atoms of the alkoxy group has been replaced by a phenyl group. Examples of phenylalkoxy include phenylmethoxy and phenylethoxy. Particular phenylalkoxy group is phenylmethoxy.

The term "phenylalkyl" denotes an alkyl group wherein at least one of the hydrogen atoms of the alkyl group has been replaced a phenyl. Particular phenylalkyl groups are benzyl, phenethyl and phenylpropyl. More particular phenylalkyl groups are benzyl and phenethyl. Further particular phenylalkyl group is benzyl.

The term "phenylalkynyl" denotes an alkynyl group wherein at least one of the hydrogen atoms of the alkynyl group has been replaced a phenyl. Particular phenylalkynyl group is phenylethynyl.

The term "phenylcycloalkyl" denotes a cycloalkyl group wherein at least one of the hydrogen atoms of the cycloalkyl group has been replaced a phenyl. Particular phenylcycloalkyl group is phenylcyclopropyl.

The term "pyridazinylalkenyl" denotes an alkenyl group wherein at least one of the hydrogen atoms of the alkenyl group has been replaced a pyridazinyl. Particular pyridazinylalkenyl group is pyridazinylethenyl.

The term "pyridazinylalkyl" denotes an alkyl group wherein at least one of the hydrogen atoms of the alkyl group has been replaced a pyridazinyl. Particular pyridazinylalkyl groups are pyridazinylmethyl, pyridazinylethyl and pyridazinylpropyl. More particular pyridazinylalkyl group is pyridazinylethyl.

The term "pyridazinylalkynyl" denotes an alkynyl group wherein at least one of the hydrogen atoms of the alkynyl group has been replaced a pyridazinyl. Particular pyridazinylalkynyl group is pyridazinylethynyl.

The term "pyridinonylalkenyl" denotes an alkenyl group wherein at least one of the hydrogen atoms of the alkenyl group has been replaced a pyridinonyl. Particular pyridinonylalkenyl group is pyridinonylethenyl.

The term "pyridinonylalkyl" denotes an alkyl group wherein at least one of the hydrogen atoms of the alkyl group has been replaced a pyridinonyl. Particular pyridinonylalkyl groups are pyridinonylmethyl, pyridinonylethyl and pyridinonylpropyl. More particular pyridinonylalkyl group is pyridinonylethyl.

The term "pyridinonyl alkynyl" denotes an alkynyl group wherein at least one of the hydrogen atoms of the alkynyl group has been replaced a pyridinonyl. Particular pyridinonyl alkynyl group is pyridinonylethynyl.

The term "pyridinylalkenyl" denotes an alkenyl group wherein at least one of the hydrogen atoms of the alkenyl group has been replaced a pyridinyl. Particular pyridinylalkenyl group is pyridinylethenyl.

The term "pyridinylalkyl" denotes an alkyl group wherein at least one of the hydrogen atoms of the alkyl group has been replaced a pyridinyl. Particular pyridinylalkyl groups are pyridinylmethyl, pyridinylethyl and pyridinylpropyl. More particular pyridinylalkyl group is pyridinylethyl.

The term "pyridinylalkynyl" denotes an alkynyl group wherein at least one of the hydrogen atoms of the alkynyl group has been replaced a pyridinyl. Particular pyridinylalkynyl group is pyridinylethynyl.

The term "thiophenylalkenyl" denotes an alkenyl group wherein at least one of the hydrogen atoms of the alkenyl group has been replaced a thiophenyl. Particular thiophenylalkenyl group is thiophenylethenyl.

The term "thiophenylalkyl" denotes an alkyl group wherein at least one of the hydrogen atoms of the alkyl group has been replaced a thiophenyl. Particular thiophenylalkyl groups are thiophenylmethyl, thiophenylethyl and thiophenylpropyl. More particular thiophenylalkyl group is thiophenylmethyl.

The term "thiophenylalkynyl" denotes an alkynyl group wherein at least one of the hydrogen atoms of the alkynyl group has been replaced a thiophenyl. Particular thiophenylalkynyl group is thiophenylethynyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition, these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the sodium and potassium salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes a group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn) groups. Further particular protecting groups are the tert-butoxycarbonyl (Boc) and the fluorenylmethoxycarbonyl (Fmoc) groups. More particular protecting group is the tert-butoxycarbonyl (Boc) group.

The abbreviation uM means microMolar and is equivalent to the symbol µM.

The abbreviation uL means microliter and is equivalent to the symbol µL.

The abbreviation ug means microgram and is equivalent to the symbol µg.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Also an embodiment of the present invention are compounds according to formula (I) as described herein and pharmaceutically acceptable salts or esters thereof, in particular compounds according to formula (I) as described herein and pharmaceutically acceptable salts thereof, more particularly compounds according to formula (I) as described herein.

A more particular embodiment of the present invention are compounds according to formula (I) as described herein, wherein the compounds are of formula (Ic).

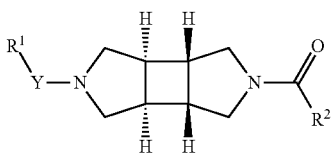

(Ic)

Another embodiment of the present invention are compounds according to formula (I) as described herein, wherein R¹ is substituted quinolinyl, substituted 1,2,3,4-tetrahydroquinolinyl, substituted isoquinolinyl, substituted 1,2,3,4-tetrahydroisoquinolinyl, substituted 9H-carbazolyl, substituted chromanyl, substituted indolyl, substituted naphthyl, substituted oxazolyl, substituted phenyl, substituted phenylalkyl, substituted phenoxyalkyl, substituted phenylalkoxy, substituted phenylalkenyl, substituted pyridazinyl, substituted pyridinyl, substituted pyridinonyl, substituted tetralinyl or substituted tetralinonyl, wherein substituted quinolinyl, substituted 1,2,3,4-tetrahydroquinolinyl, substituted isoquinolinyl, substituted 1,2,3,4-tetrahydroisoquinolinyl, substituted 9H-carbazolyl, substituted chromanyl, substituted indolyl, substituted naphthyl, substituted oxazolyl, substituted phenyl, substituted phenylalkyl, substituted phenoxyalkyl, substituted phenylalkoxy, substituted phenylalkenyl, substituted pyridazinyl, substituted pyridinyl, substituted pyridinonyl, substituted tetralinyl and substituted tetralinonyl are substituted with $R^6$, $R^7$ and $R^8$.

A particular embodiment of the present invention are compounds according to formula (I) as described herein, wherein $R^1$ is substituted quinolinyl, substituted indolyl, substituted naphthyl, substituted phenylalkoxy, substituted phenylalkenyl or substituted pyridinyl, wherein substituted quinolinyl, substituted indolyl, substituted naphthyl, substituted phenylalkoxy, substituted phenylalkenyl and substituted pyridinyl are substituted with $R^6$, $R^7$ and $R^8$.

In a further embodiment of the present invention are compounds according to formula (I) as described herein, wherein $R^1$ is substituted quinolinyl, substituted indolyl, substituted naphthyl or substituted pyridinyl, wherein substituted quinolinyl, substituted indolyl, substituted naphthyl and substituted pyridinyl are substituted with $R^6$, $R^7$ and $R^8$.

The present invention also relates to compounds according to formula (I) as described herein, wherein $R^2$ is selected from the ring systems A and C.

A further particular embodiment of the present invention are compounds according to formula (I) as described herein, wherein $R^2$ is the ring system A and of formula (Ia).

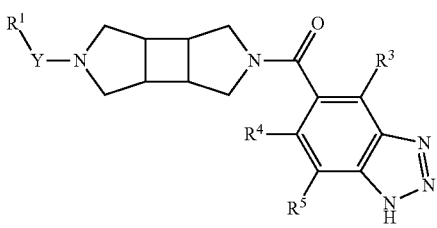

(Ia)

Also an embodiment of the present invention are compounds according to formula (I) as described herein, wherein Y is —C(O)—.

Another embodiment of the present invention are compounds according to formula (I) as described herein, wherein $R^3$, $R^4$ and $R^5$ are independently selected from H and halogen.

A further embodiment of the present invention are compounds according to formula (I) as described herein, wherein $R^3$, $R^4$ and $R^5$ are H.

The present invention also relates to compounds according to formula (I) as described herein, wherein $R^6$ is H, halogen, cyano, cyanoalkyl, alkyl, haloalkyl, cycloalkylalkoxy, alkoxy, alkoxyalkyl, haloalkoxy, alkoxyalkoxy, phenyl, phenylalkoxy or phenyl substituted with one to three halogen.

A further embodiment of the present invention are compounds according to formula (I) as described herein, wherein $R^6$ is alkoxy, haloalkoxy or alkoxyalkoxy.

Another embodiment of the present invention are compounds according to formula (I) as described herein, wherein $R^7$ is H, halogen, alkyl, cycloalkyl, alkoxy, haloalkoxy, alkylsulfonyl, furanyl or tetrahydropyranyl.

A further particular embodiment of the present invention are compounds according to formula (I) as described herein, wherein $R^7$ is H or halogen.

Also an embodiment of the present invention are compounds according to formula (I) as described herein, wherein $R^8$ is H or alkyl.

A particular embodiment of the present invention are compounds according to formula (I) as described herein, wherein $R^8$ is H.

A more particular embodiment of the present invention are compounds according to formula (I) as described herein, wherein $R^1$ is substituted quinolinyl, substituted indolyl, substituted naphthyl or substituted pyridinyl, wherein substituted quinolinyl, substituted indolyl, substituted naphthyl and substituted pyridinyl are substituted with $R^6$, $R^7$ and $R^8$, Y is —C(O)— and $R^2$ is the ring system A and of formula (Ib).

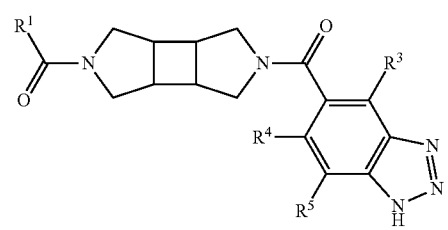

(Ib)

A further particular embodiment of the present invention are compounds according to formula (I) as described herein, wherein the compounds are of formula (Ic).

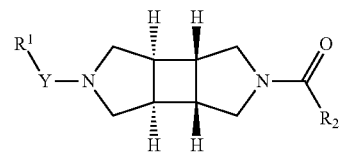

(Ic)

Particular examples of compounds of formula (I) as described herein are selected from [(3aS,3bS,6aR,6bR)-5-(1H-benzotriazole-5-carbonyl)-octahydro-cyclobuta[1,2-c;3,4-c']dipyrrol-2-yl]-(6-chloro-naphthalen-2-yl)-methanone;

1-[(3aS,3bR,6aS,6bR)-5-(1H-benzotriazole-5-carbonyl)-octahydro-cyclobuta[1,2-c;3,4-c']dipyrrol-2-yl]-3-(4-trifluoromethoxy-phenyl)-propan-1-one;

[(3aS,3bS,6aR,6bR)-5-(1H-benzotriazole-5-carbonyl)-octahydro-cyclobuta[1,2-c;3,4-c']dipyrrol-2-yl]-(4'-fluoro-biphenyl-4-yl)-methanone;

(E)-1-[(3aS,3bR,6aS,6bR)-5-(1H-benzotriazole-5-carbonyl)-octahydro-cyclobuta[1,2-c;3,4-c']dipyrrol-2-yl]-3-(4-trifluoromethoxy-phenyl)-propenone;

[(3aS,3bS,6aR,6bR)-5-(1H-benzotriazole-5-carbonyl)-octahydro-cyclobuta[1,2-c;3,4-c']dipyrrol-2-yl]-(6-bromo-naphthalen-2-yl)-methanone;

[(3aS,3bS,6aR,6bR)-5-(1H-benzotriazole-5-carbonyl)-octahydro-cyclobuta[1,2-c;3,4-c']dipyrrol-2-yl]-(6-methoxy-naphthalen-2-yl)-methanone;

(E)-1-[(3aS,3bS,6aR,6bR)-5-((R)-4,5,6,7-tetrahydro-1H-benzotriazole-5-carbonyl)-octahydro-cyclobuta[1,2-c;3,4-c']dipyrrol-2-yl]-3-(4-trifluoromethoxy-phenyl)-propenone;

6-[(3aS,3bS,6aR,6bR)-5-(1H-benzotriazole-5-carbonyl)-octahydro-cyclobuta[1,2-c;3,4-c']dipyrrole-2-carbonyl]-naphthalene-2-carbonitrile;

1-[(3aR,3bS,6aR,6bS)-5-(1H-benzotriazole-5-carbonyl)-octahydro-cyclobuta[1,2-c;3,4-c']dipyrrol-2-yl]-2-(4-trifluoromethoxy-phenoxy)-ethanone;

1-[(3aR,3bS,6aR,6bS)-5-(1H-benzotriazole-5-carbonyl)-octahydro-cyclobuta[1,2-c;3,4-c']dipyrrol-2-yl]-2-(2-isopropyl-phenoxy)-ethanone;

[(3aR,3bS,6aR,6bS)-5-(1H-benzotriazole-5-carbonyl)-octahydro-cyclobuta[1,2-c;3,4-c']dipyrrol-2-yl]-(5-trifluoromethoxy-1H-indol-2-yl)-methanone;

[(3aR,3bS,6aR,6bS)-5-(1H-benzotriazole-5-carbonyl)-octahydro-cyclobuta[1,2-c;3,4-c']dipyrrol-2-yl]-(6-trifluoromethoxy-1H-indol-2-yl)-methanone;

[(3aS,3bS,6aR,6bR)-5-(1H-benzotriazole-5-carbonyl)-octahydro-cyclobuta[1,2-c;3,4-c']dipyrrol-2-yl]-naphthalen-2-yl-methanone;

[(3aS,3bS,6aR,6bR)-5-(1H-benzotriazole-5-carbonyl)-octahydro-cyclobuta[1,2-c;3,4-c']dipyrrol-2-yl]-(6-methyl-naphthalen-2-yl)-methanone;

[(3aS,3bS,6aR,6bR)-5-(1H-benzotriazole-5-carbonyl)-octahydro-cyclobuta[1,2-c;3,4-c']dipyrrol-2-yl]-(7-methyl-naphthalen-2-yl)-methanone;

[(3aS,3bS,6aR,6bR)-5-(1H-benzotriazole-5-carbonyl)-octahydro-cyclobuta[1,2-c;3,4-c']dipyrrol-2-yl]-(6-phenyl-naphthalen-2-yl)-methanone;

(6-bromo-naphthalen-2-yl)-[(3aR,3bS,6aR,6bS)-5-((R)-4,5,6,7-tetrahydro-1H-benzotriazole-5-carbonyl)-octahydro-cyclobuta[1,2-c;3,4-c']dipyrrol-2-yl]-methanone;

[(3aS,3bS,6aR,6bR)-5-(1H-benzotriazole-5-carbonyl)-octahydro-cyclobuta[1,2-c;3,4-c']dipyrrol-2-yl]-(4'-chloro-biphenyl-4-yl)-methanone;

(4'-chloro-biphenyl-4-yl)-[(3aS,3bS,6aR,6bS)-5-((R)-4,5,6,7-tetrahydro-1H-benzotriazole-5-carbonyl)-octahydro-cyclobuta[1,2-c;3,4-c']dipyrrol-2-yl]-methanone;

[(3aR,3bS,6aR,6bS)-5-((R)-4,5,6,7-tetrahydro-1H-benzotriazole-5-carbonyl)-octahydro-cyclobuta[1,2-c;3,4-c']dipyrrol-2-yl]-(5-trifluoromethoxy-1H-indol-2-yl)-methanone;

[(3aR,3bS,6aR,6bS)-5-((R)-4,5,6,7-tetrahydro-1H-benzotriazole-5-carbonyl)-octahydro-cyclobuta[1,2-c;3,4-c']dipyrrol-2-yl]-(6-trifluoromethoxy-1H-indol-2-yl)-methanone;

[(3aS,3bS,6aR,6bR)-5-(1H-benzotriazole-5-carbonyl)-octahydro-cyclobuta[1,2-c;3,4-c']dipyrrol-2-yl]-(3-methoxy-naphthalen-2-yl)-methanone;

[(3aS,3bS,6aR,6bR)-5-(1H-benzotriazole-5-carbonyl)-octahydro-cyclobuta[1,2-c;3,4-c']dipyrrol-2-yl]-(1-methoxy-naphthalen-2-yl)-methanone;

[(3aR,3bS,6aR,6bS)-5-(1H-benzotriazole-5-carbonyl)-octahydro-cyclobuta[1,2-c;3,4-c']dipyrrol-2-yl]-(1H-indol-2-yl)-methanone;

[(3aR,3bS,6aR,6bS)-5-(1H-benzotriazole-5-carbonyl)-octahydro-cyclobuta[1,2-c;3,4-c']dipyrrol-2-yl]-(1-methyl-1H-indol-2-yl)-methanone;

[(3aS,3bS,6aR,6bR)-5-(1H-benzotriazole-5-carbonyl)-octahydro-cyclobuta[1,2-c;3,4-c']dipyrrol-2-yl]-(4-cyclopropylmethoxy-naphthalen-2-yl)-methanone;

[(3aS,3bS,6aR,6bR)-5-(1H-benzotriazole-5-carbonyl)-octahydro-cyclobuta[1,2-c;3,4-c']dipyrrol-2-yl]-(4-methoxy-naphthalen-2-yl)-methanone;

2-[(3aR,3bS,6aR,6bS)-5-(1H-benzotriazole-5-carbonyl)-octahydro-cyclobuta[1,2-c;3,4-c']dipyrrole-2-carbonyl]-1H-indole-5-carbonitrile;

[(3aS,3bS,6aR,6bR)-5-(1H-benzotriazole-5-carbonyl)-octahydro-cyclobuta[1,2-c;3,4-c']dipyrrol-2-yl]-(3-methoxy-phenyl)-methanone;

[(3aS,3bS,6aR,6bR)-5-(1H-benzotriazole-5-carbonyl)-octahydro-cyclobuta[1,2-c;3,4-c']dipyrrol-2-yl]-(4-methoxy-quinolin-2-yl)-methanone;

[(3aS,3bS,6aR,6bR)-5-(1H-benzotriazole-5-carbonyl)-octahydro-cyclobuta[1,2-c;3,4-c']dipyrrol-2-yl]-[2-(4-chloro-phenyl)-5-methyl-oxazol-4-yl]-methanone;

[(3aS,3bR,6aS,6bR)-5-(1H-benzotriazole-5-carbonyl)-octahydro-cyclobuta[1,2-c;3,4-c']dipyrrol-2-yl]-(1,2,3,4-tetrahydro-naphthalen-2-yl)-methanone;

[(3aR,3bS,6aR,6bS)-5-(1H-benzotriazole-5-carbonyl)-octahydro-cyclobuta[1,2-c;3,4-c']dipyrrol-2-yl]-(1-methyl-5-trifluoromethoxy-1H-indol-2-yl)-methanone;

[(3aS,3bS,6aR,6bR)-5-(1H-benzotriazole-5-carbonyl)-octahydro-cyclobuta[1,2-c;3,4-c']dipyrrol-2-yl]-(6-chloro-1H-indol-2-yl)-methanone;

[(3aR,3bS,6aR,6bS)-5-(1H-benzotriazole-5-carbonyl)-octahydro-cyclobuta[1,2-c;3,4-c']dipyrrol-2-yl]-(6-chloro-1-methyl-1H-indol-2-yl)-methanone;

[(3aR,3bS,6aR,6bS)-5-(1H-benzotriazole-5-carbonyl)-octahydro-cyclobuta[1,2-c;3,4-c']dipyrrol-2-yl]-(6-methyl-1H-indol-2-yl)-methanone;

{2-[(3aR,3bS,6aR,6bS)-5-(1H-benzotriazole-5-carbonyl)-octahydro-cyclobuta[1,2-c;3,4-c']dipyrrole-2-carbonyl]-indol-1-yl}-acetonitrile;

[(3aR,3bS,6aR,6bS)-5-(1H-benzotriazole-5-carbonyl)-octahydro-cyclobuta[1,2-c;3,4-c']dipyrrol-2-yl]-(1-isobutyl-1H-indol-2-yl)-methanone;

[(3aR,3bS,6aR,6bS)-5-(1H-benzotriazole-5-carbonyl)-octahydro-cyclobuta[1,2-c;3,4-c']dipyrrol-2-yl]-quinolin-2-yl-methanone;

[(3aR,3bS,6aR,6bS)-5-(1H-benzotriazole-5-carbonyl)-octahydro-cyclobuta[1,2-c;3,4-c']dipyrrol-2-yl]-isoquinolin-3-yl-methanone;

[(3aS,3bS,6aR,6bR)-5-(1H-benzotriazole-5-carbonyl)-octahydro-cyclobuta[1,2-c;3,4-c']dipyrrol-2-yl]-(1H-indol-6-yl)-methanone;

3-[(3aS,3bR,6aS,6bR)-5-(1H-benzotriazole-5-carbonyl)-octahydro-cyclobuta[1,2-c;3,4-c']dipyrrole-2-carbonyl]-3,4-dihydro-2H-naphthalen-1-one;

[(3aR,3bS,6aR,6bS)-5-(1H-benzotriazole-5-carbonyl)-octahydro-cyclobuta[1,2-c;3,4-c']dipyrrol-2-yl]-chroman-2-yl-methanone;

[(3aS,3bS,6aR,6bR)-5-(1H-benzotriazole-5-carbonyl)-octahydro-cyclobuta[1,2-c;3,4-c']dipyrrol-2-yl]-(1H-indol-5-yl)-methanone;

(4-methoxy-naphthalen-2-yl)-[(3aR,3bS,6aR,6bS)-5-((R)-4,5,6,7-tetrahydro-1H-benzotriazole-5-carbonyl)-octahydro-cyclobuta[1,2-c;3,4-c']dipyrrol-2-yl]-methanone;

[(3aS,3bS,6aR,6bR)-5-(1H-benzotriazole-5-carbonyl)-octahydro-cyclobuta[1,2-c;3,4-c']dipyrrol-2-yl]-[6-(4-chlorophenyl)-pyridin-3-yl]-methanone;
[(3aR,3bS,6aR,6bS)-5-(1H-benzotriazole-5-carbonyl)-octahydro-cyclobuta[1,2-c;3,4-c']dipyrrol-2-yl]-(1-methoxy-isoquinolin-3-yl)-methanone;
[(3aR,3bS,6aR,6bS)-5-(1H-benzotriazole-5-carbonyl)-octahydro-cyclobuta[1,2-c;3,4-c']dipyrrol-2-yl]-(4-methyl-quinolin-2-yl)-methanone;
[(3aR,3bS,6aR,6bS)-5-(1H-benzotriazole-5-carbonyl)-octahydro-cyclobuta[1,2-c;3,4-c']dipyrrol-2-yl]-(5-chloro-1H-indol-2-yl)-methanone;
[(3aS,3bS,6aR,6bR)-5-(1H-benzotriazole-5-carbonyl)-octahydro-cyclobuta[1,2-c;3,4-c']dipyrrol-2-yl]-[4-(2-methoxy-ethoxy)-naphthalen-2-yl]-methanone;
[(3aS,3bS,6aR,6bR)-5-(1H-benzotriazole-5-carbonyl)-octahydro-cyclobuta[1,2-c;3,4-c']dipyrrol-2-yl]-(7-phenyl-naphthalen-2-yl)-methanone;
[(3aS,3bS,6aR,6bR)-5-(1H-benzotriazole-5-carbonyl)-octahydro-cyclobuta[1,2-c;3,4-c']dipyrrol-2-yl]-(4-ethoxy-naphthalen-2-yl)-methanone;
[(3aS,3bS,6aR,6bR)-5-(1H-benzotriazole-5-carbonyl)-octahydro-cyclobuta[1,2-c;3,4-c']dipyrrol-2-yl]-(4-isopropoxy-naphthalen-2-yl)-methanone;
[(3aS,3bS,6aR,6bR)-5-(1H-benzotriazole-5-carbonyl)-octahydro-cyclobuta[1,2-c;3,4-c']dipyrrol-2-yl]-(4-benzyloxy-1H-indol-6-yl)-methanone;
[(3aS,3bS,6aR,6bR)-5-(1H-benzotriazole-5-carbonyl)-octahydro-cyclobuta[1,2-c;3,4-c']dipyrrol-2-yl]-(5,6,7,8-tetrahydro-naphthalen-2-yl)-methanone;
[(3aS,3bR,6aS,6bR)-5-(1H-benzotriazole-5-carbonyl)-octahydro-cyclobuta[1,2-c;3,4-c']dipyrrol-2-yl]-(4,4-dimethyl-1,2,3,4-tetrahydro-naphthalen-2-yl)-methanone;
[(3aS,3bR,6aS,6bR)-5-(1H-benzotriazole-5-carbonyl)-octahydro-cyclobuta[1,2-c;3,4-c']dipyrrol-2-yl]-[1-(3-methoxy-propyl)-1,2,3,4-tetrahydro-quinolin-3-yl]-methanone;
[(3aR,3bS,6aR,6bS)-5-(1H-benzotriazole-5-carbonyl)-octahydro-cyclobuta[1,2-c;3,4-c']dipyrrol-2-yl]-[1-(2-methoxy-ethoxy)-isoquinolin-3-yl]-methanone;
[(3aR,3bS,6aR,6bS)-5-(1H-benzotriazole-5-carbonyl)-octahydro-cyclobuta[1,2-c;3,4-c']dipyrrol-2-yl]-(1-cyclopropylmethoxy-isoquinolin-3-yl)-methanone;
(4-isopropoxy-naphthalen-2-yl)-[(3aR,3bS,6aR,6bS)-5-((R)-4,5,6,7-tetrahydro-1H-benzotriazole-5-carbonyl)-octahydro-cyclobuta[1,2-c;3,4-c']dipyrrol-2-yl]-methanone;
[(3aR,3bS,6aR,6bS)-5-(1H-benzotriazole-5-carbonyl)-octahydro-cyclobuta[1,2-c;3,4-c']dipyrrol-2-yl]-[1-(2,2,2-trifluoro-ethoxy)-isoquinolin-3-yl]-methanone;
[(3aS,3bS,6aR,6bR)-5-(1H-benzotriazole-5-carbonyl)-octahydro-cyclobuta[1,2-c;3,4-c']dipyrrol-2-yl]-(4-isopropoxy-1H-indol-6-yl)-methanone;
4-[(3aS,3bS,6aR,6bR)-5-(4-isopropoxy-naphthalene-2-carbonyl)-octahydro-cyclobuta[1,2-c;3,4-c']dipyrrole-2-carbonyl]-benzenesulfonamide;
[6-(4-chloro-phenyl)-pyridin-3-yl]-[(3aR,3bS,6aR,6bS)-5-((R)-4,5,6,7-tetrahydro-1H-benzotriazole-5-carbonyl)-octahydro-cyclobuta[1,2-c;3,4-c']dipyrrol-2-yl]-methanone;
(1-cyclopropylmethoxy-isoquinolin-3-yl)-[(3aR,3bS,6aR,6bS)-5-((R)-4,5,6,7-tetrahydro-1H-benzotriazole-5-carbonyl)-octahydro-cyclobuta[1,2-c;3,4-c']dipyrrol-2-yl]-methanone;
[(3aS,3bS,6aR,6bR)-5-(1H-benzotriazole-5-carbonyl)-octahydro-cyclobuta[1,2-c;3,4-c']dipyrrol-2-yl]-(4-isopropoxy-1-methyl-1H-indol-6-yl)-methanone;
[(3aR,3bS,6aR,6bS)-5-(1H-benzotriazole-5-carbonyl)-octahydro-cyclobuta[1,2-c;3,4-c']dipyrrol-2-yl]-(4-ethoxy-quinolin-2-yl)-methanone;
[(3aR,3bS,6aR,6bS)-5-(1H-benzotriazole-5-carbonyl)-octahydro-cyclobuta[1,2-c;3,4-c']dipyrrol-2-yl]-(4-isopropoxy-quinolin-2-yl)-methanone;
[(3aS,3bS,6aR,6bR)-5-(1H-benzotriazole-5-carbonyl)-octahydro-cyclobuta[1,2-c;3,4-c']dipyrrol-2-yl]-(6-chloro-9H-carbazol-2-yl)-methanone;
[(3aR,3bS,6aR,6bS)-5-(1H-benzotriazole-5-carbonyl)-octahydro-cyclobuta[1,2-c;3,4-c']dipyrrol-2-yl]-[4-(2-methoxy-ethoxy)-quinolin-2-yl]-methanone;
[(3aR,3bS,6aR,6bS)-5-(1H-benzotriazole-5-carbonyl)-octahydro-cyclobuta[1,2-c;3,4-c']dipyrrol-2-yl]-(4-isopropoxy-7-trifluoromethyl-quinolin-2-yl)-methanone;
[(3aR,3bS,6aR,6bS)-5-(1H-benzotriazole-5-carbonyl)-octahydro-cyclobuta[1,2-c;3,4-c']dipyrrol-2-yl]-(4-cyclopropylmethoxy-quinolin-2-yl)-methanone;
[(3aR,3bS,6aR,6bS)-5-(1H-benzotriazole-5-carbonyl)-octahydro-cyclobuta[1,2-c;3,4-c']dipyrrol-2-yl]-[5-(4-chloro-phenyl)-pyridin-2-yl]-methanone;
[(3aR,3bS,6aR,6bS)-5-(1H-benzotriazole-5-carbonyl)-octahydro-cyclobuta[1,2-c;3,4-c']dipyrrol-2-yl]-(1-ethoxy-isoquinolin-3-yl)-methanone;
[(3aS,3bS,6aR,6bR)-5-(1H-benzotriazole-5-carbonyl)-octahydro-cyclobuta[1,2-c;3,4-c']dipyrrol-2-yl]-(1-ethyl-4-isopropoxy-1H-indol-6-yl)-methanone;
6-[(3aS,3bS,6aR,6bS)-5-(1H-benzotriazole-5-carbonyl)-octahydro-cyclobuta[1,2-c;3,4-c']dipyrrole-2-carbonyl]-3-(4-chloro-phenyl)-1H-pyridin-2-one;
1-[(3aS,3bS,6aR,6bS)-5-(1H-benzotriazole-5-carbonyl)-octahydro-cyclobuta[1,2-c;3,4-c']dipyrrol-2-yl]-(7-chloro-4-ethoxy-quinolin-2-yl)-methanone;
(7-chloro-4-ethoxy-quinolin-2-yl)-[(3aR,3bS,6aR,6bS)-5-((R)-4,5,6,7-tetrahydro-1H-benzotriazole-5-carbonyl)-octahydro-cyclobuta[1,2-c;3,4-c']dipyrrol-2-yl]methanone;
[(3aS,3bS,6aR,6bR)-5-(1H-benzotriazole-5-carbonyl)-octahydro-cyclobuta[1,2-c;3,4-c']dipyrrol-2-yl]-(4-isopropoxy-5,6,7,8-tetrahydro-naphthalen-2-yl)-methanone;
(1H-benzotriazol-5-yl)-{(3aS,3bR,6aS,6bR)-5-[4-(2-methoxy-ethoxy)-7-trifluoromethyl-quinoline-2-carbonyl]-octahydro-cyclobuta[1,2-c;3,4-c']dipyrrol-2-yl}-methanone;
(1H-benzotriazol-5-yl)-[(3aS,3bR,6aS,6bR)-5-(4-ethoxy-6-trifluoromethyl-quinoline-2-carbonyl)-octahydro-cyclobuta[1,2-c;3,4-c']dipyrrol-2-yl]-methanone;
[(3aS,3bS,6aR,6bR)-5-(1H-benzotriazole-5-carbonyl)-octahydro-cyclobuta[1,2-c;3,4-c']dipyrrol-2-yl]-(4-ethoxy-1-ethyl-1H-indol-5-yl)-methanone;
[(3aS,3bS,6aR,6bR)-5-(1H-benzotriazole-5-carbonyl)-octahydro-cyclobuta[1,2-c;3,4-c']dipyrrol-2-yl]-[1-ethyl-4-(2,2,2-trifluoro-ethoxy)-1H-indol-5-yl]-methanone;
5-[(3aS,3bR,6aS,6bR)-5-(4-ethoxy-quinoline-2-carbonyl)-octahydro-cyclobuta[1,2-c;3,4-c']dipyrrole-2-carbonyl]-pyridine-2-sulfonic acid amide;
(1H-benzotriazol-5-yl)-{(3aS,3bR,6aS,6bR)-5-[4-(2,2,2-trifluoro-ethoxy)-quinoline-2-carbonyl]-octahydro-cyclobuta[1,2-c;3,4-c']dipyrrol-2-yl}-methanone;
(1H-benzotriazol-5-yl)-{(3aS,3bS,6aR,6bR)-5-[4-ethoxy-1-(2,2,2-trifluoro-ethyl)-1H-indole-6-carbonyl]-octahydro-cyclobuta[1,2-c;3,4-c']dipyrrol-2-yl}-methanone;
(1H-benzotriazol-5-yl)-[(3aS,3bR,6aS,6bR)-5-(5-chloro-4-cyclopropylmethoxy-pyridine-2-carbonyl)-octahydro-cyclobuta[1,2-c;3,4-c']dipyrrol-2-yl]-methanone;

(1H-benzotriazol-5-yl)-[(3aS,3bR,6aS,6bR)-5-(5-cyclopropyl-6-cyclopropylmethoxy-pyridine-2-carbonyl)-octahydro-cyclobuta[1,2-c;3,4-c']dipyrrol-2-yl]-methanone;

(3,4-dimethyl-phenyl)-[(3aS,3bR,6aS,6bR)-5-(4-ethoxy-5,6,7,8-tetrahydro-quinoline-2-carbonyl)-octahydro-cyclobuta[1,2-c;3,4-c']dipyrrol-2-yl]-methanone;

(1H-benzotriazol-5-yl)-[(3aS,3bS,6aR,6bR)-5-(4'-chloro-biphenyl-3-carbonyl)-octahydro-cyclobuta[1,2-c;3,4-c']dipyrrol-2-yl]-methanone;

(1H-benzotriazol-5-yl)-[(3aS,3bR,6aS,6bR)-5-(4-ethoxy-7-methoxy-quinoline-2-carbonyl)-octahydro-cyclobuta[1,2-c;3,4-c']dipyrrol-2-yl]-methanone;

[(3aS,3bS,6aR,6bR)-5-(4-Ethoxy-6-trifluoromethyl-quinoline-2-carbonyl)-octahydro-cyclobuta[1,2-c;3,4-c']dipyrrol-2-yl]-(1H-[1,2,3]triazolo[4,5-b]pyridin-5-yl)-methanone;

[(3aS,3bS,6aR,6bR)-5-(1-ethoxy-isoquinoline-3-carbonyl)-octahydro-cyclobuta[1,2-c;3,4-c']dipyrrol-2-yl]-(1H-[1,2,3]triazolo[4,5-b]pyridin-5-yl)-methanone;

(1H-benzotriazol-5-yl)-[(3aS,3bR,6aS,6bR)-5-(6-cyclopropylmethoxy-5-trifluoromethyl-pyridine-2-carbonyl)-octahydro-cyclobuta[1,2-c;3,4-c']dipyrrol-2-yl]-methanone;

(1H-benzotriazol-5-yl)-{(3aS,3bR,6aS,6bR)-5-[5-cyclopropyl-4-(2,2,2-trifluoro-ethoxy)-pyridine-2-carbonyl]-octahydro-cyclobuta[1,2-c;3,4-c']dipyrrol-2-yl}-methanone;

(1H-benzotriazol-5-yl)-{(3aS,3bR,6aS,6bR)-5-[6-cyclopropyl-5-(2,2,2-trifluoro-ethoxy)-pyridazine-3-carbonyl]-octahydro-cyclobuta[1,2-c;3,4-c']dipyrrol-2-yl}-methanone']dipyrrol-2-yl}-methanone;

[(3aR,3bS,6aR,6bS)-5-(1H-benzotriazole-5-carbonyl)-octahydro-cyclobuta[1,2-c;3,4-c']dipyrrol-2-yl]-(6-chloro-4-ethoxy-quinolin-2-yl)-methanone;

(1H-benzotriazol-5-yl)-{(3aS,3bR,6aS,6bR)-5-[6-(2,2,2-trifluoro-ethoxy)-5-trifluoromethyl-pyridine-2-carbonyl]-octahydro-cyclobuta[1,2-c;3,4-c']dipyrrol-2-yl}-methanone;

(1H-benzotriazol-5-yl)-{(3aS,3bR,6aS,6bR)-5-[6-(2,2,2-trifluoro-ethoxy)-pyridine-2-carbonyl]-octahydro-cyclobuta[1,2-c;3,4-c']dipyrrol-2-yl}-methanone;

(1H-benzotriazol-5-yl)-{(3aS,3bS,6aR,6bR)-5-[6-(2,2,2-trifluoro-ethoxy)-pyridine-3-carbonyl]-octahydro-cyclobuta[1,2-c;3,4-c']dipyrrol-2-yl}-methanone;

(1H-benzotriazol-5-yl)-{(3aS,3bS,6aR,6bR)-5-[5-bromo-6-(2,2,2-trifluoro-ethoxy)-pyridine-3-carbonyl]-octahydro-cyclobuta[1,2-c;3,4-c']dipyrrol-2-yl}-methanone;

(1H-benzotriazol-5-yl)-{(3aS,3bR,6aS,6bR)-5-[5-(2,2,2-trifluoro-ethoxy)-pyridine-2-carbonyl]-octahydro-cyclobuta[1,2-c;3,4-c']dipyrrol-2-yl}-methanone;

[(3aS,3bR,6aS,6bR)-5-(6-cyclopropylmethoxy-pyridazine-3-carbonyl)-octahydro-cyclobuta[1,2-c;3,4-c']dipyrrol-2-yl]-(3,4-dimethyl-phenyl)-methanone;

(1H-benzotriazol-5-yl)-{(3aS,3bS,6aR,6bR)-5-[5-bromo-2-methyl-6-(2,2,2-trifluoro-ethoxy)-pyridine-3-carbonyl]-octahydro-cyclobuta[1,2-c;3,4-c']dipyrrol-2-yl}-methanone;

(1H-benzotriazol-5-yl)-{(3aS,3bS,6aR,6bR)-5-[5-cyclopropyl-6-(2,2,2-trifluoro-ethoxy)-pyridine-3-carbonyl]-octahydro-cyclobuta[1,2-c;3,4-c']dipyrrol-2-yl}-methanone;

(1H-benzotriazol-5-yl)-{(3aS,3bS,6aR,6bR)-5-[6-(2,2,2-trifluoro-ethoxy)-5-trifluoromethyl-pyridine-3-carbonyl]-octahydro-cyclobuta[1,2-c;3,4-c']dipyrrol-2-yl}-methanone;

(1H-benzotriazol-5-yl)-{(3aS,3bS,6aR,6bR)-5-[5-(tetrahydro-pyran-4-yl)-6-(2,2,2-trifluoro-ethoxy)-pyridine-3-carbonyl]-octahydro-cyclobuta[1,2-c;3,4-c']dipyrrol-2-yl}-methanone;

(1H-benzotriazol-5-yl)-{(3aS,3bR,6aS,6bR)-5-[4-(4-chloro-phenyl)-5-(2,2,2-trifluoro-ethoxy)-pyridine-2-carbonyl]-octahydro-cyclobuta[1,2-c;3,4-c']dipyrrol-2-yl}-methanone;

(1H-benzotriazol-5-yl)-{(3aS,3bS,6aR,6bR)-5-[5-furan-2-yl-6-(2,2,2-trifluoro-ethoxy)-pyridine-3-carbonyl]-octahydro-cyclobuta[1,2-c;3,4-c']dipyrrol-2-yl}-methanone;

(1H-benzotriazol-5-yl)-{(3aS,3bS,6aR,6bR)-5-[5-chloro-6-(2,2,2-trifluoro-ethoxy)-pyridine-3-carbonyl]-octahydro-cyclobuta[1,2-c;3,4-c']dipyrrol-2-yl}-methanone;

[(3aS,3bR,6aS,6bR)-5-(4-ethoxy-quinoline-2-carbonyl)-octahydro-cyclobuta[1,2-c;3,4-c']dipyrrol-2-yl]-(4-fluoro-1H-benzotriazol-5-yl)-methanone;

{(3aS,3bS,6aR,6bR)-5-[5-methanesulfonyl-6-(2,2,2-trifluoro-ethoxy)-pyridine-3-carbonyl]-octahydro-cyclobuta[1,2-c;3,4-c']dipyrrol-2-yl}-phenyl-methanone;

(3aR,3bS,6aR,6bS)-5-(1H-benzotriazole-5-carbonyl)-octahydro-cyclobuta[1,2-c;3,4-c']dipyrrole-2-carboxylicacid 4-trifluoromethoxy-benzyl ester;

(3aR,3bS,6aR,6bS)-5-(1H-benzotriazole-5-carbonyl)-octahydro-cyclobuta[1,2-c;3,4-c']dipyrrole-2-carboxylic acid 3,5-dichloro-benzyl ester;

(1H-benzotriazol-5-yl)-[(3aS,3bR,6aS,6bR)-5-(4'-fluoro-biphenyl-4-sulfonyl)-octahydro-cyclobuta[1,2-c;3,4-c']dipyrrol-2-yl]-methanone;

(1H-benzotriazol-5-yl)-[(3aS,3bR,6aS,6bR)-5-(6-chloro-naphthalene-2-sulfonyl)-octahydro-cyclobuta[1,2-c;3,4-c']dipyrrol-2-yl]-methanone;

[(3aR,3bS,6aR,6bS)-5-(1H-benzotriazole-5-carbonyl)-octahydro-cyclobuta[1,2-c;3,4-c']dipyrrol-2-yl]-(6-trifluoromethyl-3,4-dihydro-1H-isoquinolin-2-yl)-methanone;

and pharmaceutically acceptable salts thereof.

Further particular examples of compounds of formula (I) as described herein are selected from (E)-1-[(3aS,3bR,6aS,6bR)-5-(1H-benzotriazole-5-carbonyl)-octahydro-cyclobuta[1,2-c;3,4-c']dipyrrol-2-yl]-3-(4-trifluoromethoxy-phenyl)-propenone;

(4-isopropoxy-naphthalen-2-yl)-[(3aR,3bS,6aR,6bS)-5-((R)-4,5,6,7-tetrahydro-1H-benzotriazole-5-carbonyl)-octahydro-cyclobuta[1,2-c;3,4-c']dipyrrol-2-yl]-methanone;

4-[(3aS,3bS,6aR,6bR)-5-(4-isopropoxy-naphthalene-2-carbonyl)-octahydro-cyclobuta[1,2-c;3,4-c']dipyrrole-2-carbonyl]-benzenesulfonamide;

[(3aS,3bS,6aR,6bR)-5-(1H-benzotriazole-5-carbonyl)-octahydro-cyclobuta[1,2-c;3,4-c']dipyrrol-2-yl]-(4-isopropoxy-1-methyl-1H-indol-6-yl)-methanone;

[(3aR,3bS,6aR,6bS)-5-(1H-benzotriazole-5-carbonyl)-octahydro-cyclobuta[1,2-c;3,4-c']dipyrrol-2-yl]-[4-(2-methoxy-ethoxy)-quinolin-2-yl]-methanone;

(1H-benzotriazol-5-yl)-{(3aS,3bS,6aR,6bR)-5-[5-bromo-6-(2,2,2-trifluoro-ethoxy)-pyridine-3-carbonyl]-octahydro-cyclobuta[1,2-c;3,4-c']dipyrrol-2-yl}-methanone;

(3aR,3bS,6aR,6bS)-5-(1H-benzotriazole-5-carbonyl)-octahydro-cyclobuta[1,2-c;3,4-c']dipyrrole-2-carboxylicacid 4-trifluoromethoxy-benzyl ester;

and pharmaceutically acceptable salts thereof.

Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reactions and purifications of the resulting products are known to those persons skilled in the art. In case a mixture of enantiomers or diastereoisomers is produced during a reaction, these enantiomers or diastereoisomers can be separated by methods described herein or known to the man skilled in the art such as e.g. (chiral) chromatography or crystallization. The substituents and indices used in the following description of the processes have the significance given herein.

Compounds of general formula (I) can be synthesised from amine precursor 1 and appropriate reagents, using methods well known in the art.

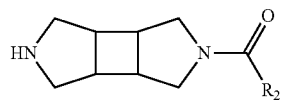
(I)

For instance, amine 1 is reacted with a suitable chloroformate ester of formula $R^1$—O—C(O)—Cl (2) ($R^1$=substituted phenylalkyl), or with an imidazole-1-carboxylate ester of formula (3A, $R^1$=substituted phenylalkyl), or with a succinimidyl carbonate derivative of formula (3B, $R^1$=phenylalkyl), leading to a compound of formula (I) wherein R is substituted phenylalkoxy.

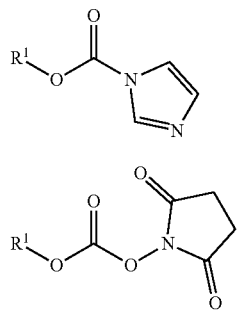

3A

3B

The reaction is performed in a suitable solvent such as dichloromethane, tetrahydrofuran, N,N-dimethylformamide, acetonitrile, acetone, water, or mixtures thereof, in the presence or not of a base, e.g., triethylamine, diisopropylethylamine, pyridine, potassium hydrogencarbonate, potassium carbonate, at temperatures between 0° C. and the boiling point of the solvent or solvent mixture.

Chloroformate esters 2 are commercially available or can be synthesised from the corresponding alcohol of formula $R^1$—OH ($R^1$=substituted phenylalkyl), by reaction with phosgene or a phosgene equivalent (e.g., diphosgene, triphosgene), as described in the literature.

Imidazole-1-carboxylate esters 3A are synthesised from the corresponding alcohols of formula $R^1$—OH ($R^1$=substituted phenylalkyl), by reaction with 1,1'-carbonyldiimidazole. The reaction is performed at room temperature, in a solvent such as dichloromethane, tetrahydrofuran or acetonitrile. The imidazole-1-carboxylate esters 3A are typically not isolated but directly reacted with amines 1 as described above.

Succinimidyl carbonate derivatives 3B are synthesised from the corresponding alcohols of formula $R^1$—OH ($R^1$=substituted phenylalkyl), by reaction with N,N'-disuccinimidyl carbonate. The reaction is performed at room temperature, in a solvent such as dichloromethane, tetrahydrofuran, or acetonitrile, optionally in the presence of a base, e.g., triethylamine. The succinimidyl carbonate derivatives 3B are typically not isolated but directly reacted with amines 1 as described above.

Alcohols of formula $R^1$—OH are commercially available or can be produced by methods described herein or known in the art.

Alternatively, amine 1 is reacted with a suitable N-(chlorocarbonyl)-1,2,3,4-tetrahydroisoquinoline 4, leading to compounds of formula (I) wherein $R^1$ is substituted 1,2,3,4-tetrahydroisoquinolin-2-yl.

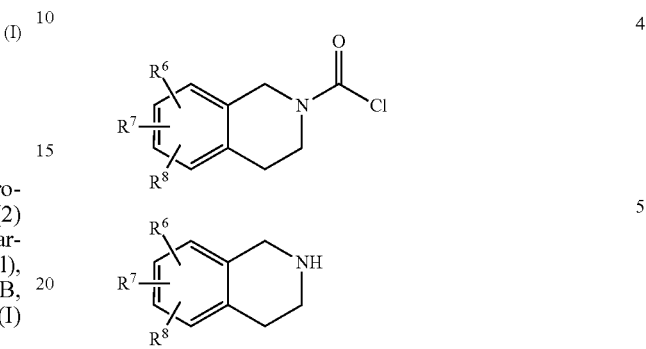

4

5

N-(chlorocarbonyl)-1,2,3,4-tetrahydroisoquinolines (4) are synthesised from the corresponding 1,2,3,4-tetrahydroisoquinolines 5 by reaction with phosgene or a phosgene equivalent, as described herein or in the literature.

Alternatively, amine 1 is reacted with a suitable carboxylic acid of formula $R^1$-COOH (6) leading to a compound of formula (I). The reaction is performed in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Amine 1 can also be reacted with suitable acylating reagents such as acyl chlorides of formula $R^1$-COCl (7) to lead to compounds of formula (I). The reaction is performed in a solvent such as dichloromethane, tetrahydrofuran, or N,N-dimethylformamide, in the presence of a base such as triethylamine or 4-methylmorpholine, at temperatures between 0° C. and 80° C.

Carboxylic acids (6) and acyl halides (7) are commercially available or can be prepared as described herein or in the literature.

Alternatively, amine 1 is reacted with a suitable sulfonyl chloride of formula $R^1$-$SO_2$Cl (8), leading to compounds of formula (I) wherein Y is —S($O_2$)—. The reaction is performed in a suitable solvent such as dichloromethane, tetrahydrofuran, N,N-dimethylformamide, acetonitrile, acetone, water, or mixtures thereof, in the presence of a base, e.g., triethylamine, diisopropylethylamine, pyridine, potassium hydrogencarbonate, potassium carbonate, at temperatures between 0° C. and the boiling point of the solvent or solvent mixture.

Sulfonyl chlorides (8) are commercially available or can be synthesised as described herein or in the literature.

Amines of general formula 1 are synthesised from tert-butyl carbamate precursors 9.

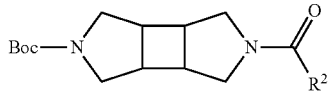

9

The deprotection of 9 may be performed in the presence of a suitable acid, e.g., hydrochloric acid or trifluoroacetic acid, in a solvent such as water, 2-propanol, dichloromethane, or 1,4-dioxane at temperatures between 0° C. and 30° C., leading to amine 1.

Amides 9 can be produced from amine 10 by reaction with appropriate reagents, using methods known in the art.

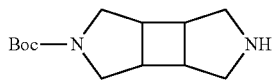

10

For instance, amine 10 is reacted with a suitable carboxylic acid of formula $R^2$—COOH (11), leading to compounds of formula 9, The reaction is performed in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Boc-protected amine 10 can be produced from diamine 12 using a suitable reagent, e.g., di-tert-butyl dicarbonate. The reaction is performed in a suitable solvent, e.g., dichloromethane, chloroform, or tetrahydrofuran at temperatures between 0° C. and 30° C.

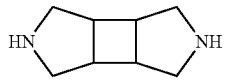

12

Alternatively, 10 can be produced from 12 in a two step sequence. In the first step, 12 is reacted with excess di-tert-butyl dicarbonate, leading to the diprotected intermediate 13. The dicarbamate 13 is mono-deprotected under suitable conditions, e.g., with hydrogen chloride, in solvents such as ethyl acetate, diethyl ether, 2-propanol, or mixtures thereof, leading to 10 as the hydrochloride salt.

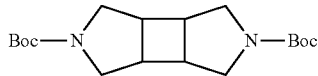

13

Amines of general formula 1 can also be synthesised from diamine 12 by reaction with appropriate reagents, using methods known in the art. For instance, diamine 12 is reacted with a suitable carboxylic acid of formula $R^2$—COOH (11), leading to compounds of formula 1, The reaction is performed in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Compounds of formula (I), can also be produced from amine precursors of general formula 14 by reaction with appropriate reagents, using methods known in the art.

14

For instance, amine 14 is reacted with a suitable carboxylic acid of formula $R^2$—COOH (11), leading to compounds of formula (I). The reaction is performed in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Amines 14 can be synthesised from diamine 12, using methods and reagents known in the art.

For instance, diamine 12 is reacted with a suitable chloroformate ester of formula $R^1$—O—C(O)—Cl (2) ($R^1$=substituted phenylalkyl), or with an imidazole-1-carboxylate ester of formula (3A, $R^1$=substituted phenylalkyl), or with a succinimidyl carbonate derivative of formula (3B, $R^1$=phenylalkyl), leading to a compound of formula 14 wherein $R^1$ is substituted phenylalkoxy. The reaction is performed in a suitable solvent such as dichloromethane, tetrahydrofuran, N,N-dimethylformamide, acetonitrile, acetone, water, or mixtures thereof, in the presence or not of a base, e.g., triethylamine, diisopropylethylamine, pyridine, potassium hydrogencarbonate, potassium carbonate, at temperatures between 0° C. and the boiling point of the solvent or solvent mixture.

Alternatively, diamine 12 is reacted with a suitable N-(chlorocarbonyl)-1,2,3,4-tetrahydroisoquinoline 4, leading to compounds of formula 14 wherein $R^1$ is substituted 1,2,3,4-tetrahydroisoquinolin-2-yl.

Alternatively, diamine 12 is reacted with a suitable carboxylic acid of formula $R^1$—COOH (6) leading to a compound of formula 14. The reaction is performed in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluorophosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Diamine 12 can also be reacted with suitable acylating reagents such as acyl chlorides of formula $R^1$-COCl (7) to lead to compounds of formula 14. The reaction is performed in a solvent such as dichloromethane, tetrahydrofuran, or N,N-dimethylformamide, in the presence of a base such as triethylamine or 4-methylmorpholine, at temperatures between 0° C. and 80° C.

Alternatively, diamine 12 is reacted with a suitable sulfonyl chloride of formula $R^1$—$SO_2Cl$ (8), leading to compounds of formula 14 wherein Y is —$S(O_2)$—. The reaction is performed in a suitable solvent such as dichloromethane, tetrahydrofuran, N,N-dimethylformamide, acetonitrile, acetone, water, or mixtures thereof, in the presence of a base, e.g., triethylamine, diisopropylethylamine, pyridine, potassium hydrogencarbonate, potassium carbonate, at temperatures between 0° C. and the boiling point of the solvent or solvent mixture.

Alternatively, amines 14 can be synthesised from their tert-butyl carbamate derivatives of formula 15 by carbamate deprotection. The deprotection may be performed in the presence of a suitable acid, e.g, hydrochloric acid or trifluoroacetic acid, in a solvent such as water, 2-propanol, dichloromethane, or 1,4-dioxane, at temperatures between 0° C. and 30° C.

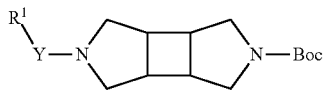

15

Intermediates 15 can be produced from amine 10 by reaction with appropriate reagents, using methods known in the art.

For instance, amine 10 is reacted with a suitable chloroformate ester of formula $R^1$-O—C(O)—Cl (2) ($R^1$=substituted phenylalkyl), or with an imidazole-1-carboxylate ester of formula (3A, $R^1$=substituted phenylalkyl), or with a succinimidyl carbonate derivative of formula (3B, $R^1$=phenylalkyl), leading to a compound of formula 15 wherein $R^1$ is substituted phenylalkoxy. The reaction is performed in a suitable solvent such as dichloromethane, tetrahydrofuran, N,N-dimethylformamide, acetonitrile, acetone, water, or mixtures thereof, in the presence or not of a base, e.g., triethylamine, diisopropylethylamine, pyridine, potassium hydrogencarbonate, potassium carbonate, at temperatures between 0° C. and the boiling point of the solvent or solvent mixture.

Alternatively, amine 10 is reacted with a suitable N-(chlorocarbonyl)-1,2,3,4-tetrahydroisoquinoline 4, leading to compounds of formula 15 wherein $R^1$ is substituted 1,2,3,4-tetrahydroisoquinolin-2-yl.

Alternatively, amine 10 is reacted with a suitable carboxylic acid of formula $R^1$-COOH (6) leading to a compound of formula 15. The reaction is performed in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Amine 12 can also be reacted with suitable acylating reagents such as acyl chlorides of formula $R^1$-COCl (7) to lead to compounds of formula 15. The reaction is performed in a solvent such as dichloromethane, tetrahydrofuran, or N,N-dimethylformamide, in the presence of a base such as triethylamine or 4-methylmorpholine, at temperatures between 0° C. and 80° C.

Alternatively, amine 10 is reacted with a suitable sulfonyl chloride of formula $R^1$—$SO_2Cl$ (8), leading to compounds of formula 15 wherein Y is —$S(O_2)$—. The reaction is performed in a suitable solvent such as dichloromethane, tetrahydrofuran, N,N-dimethylformamide, acetonitrile, acetone, water, or mixtures thereof, in the presence of a base, e.g., triethylamine, diisopropylethylamine, pyridine, potassium hydrogencarbonate, potassium carbonate, at temperatures between 0° C. and the boiling point of the solvent or solvent mixture.

Diamine 12 can be synthesised in three step from N-benzylmaleimide (16), as illustrated in scheme 1.

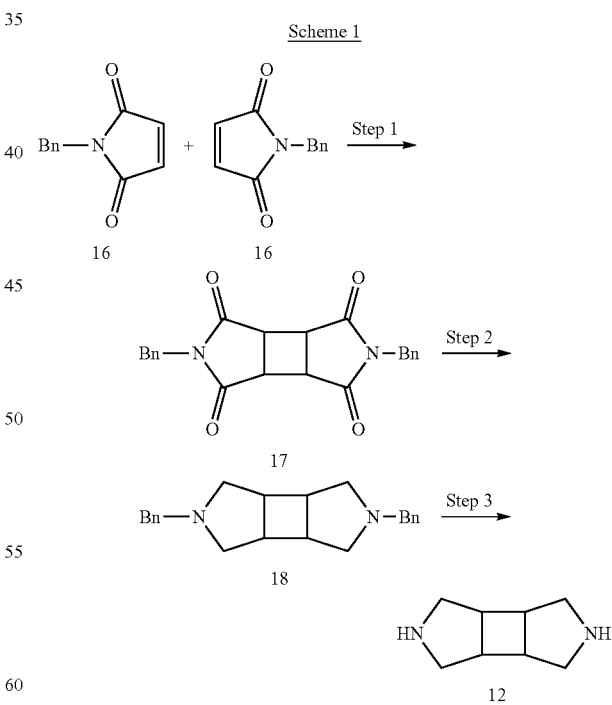

In step 1, scheme 1, N-benzylmaleimide (16) undergoes photodimerisation by irradiation with ultraviolet light (λ=300 nm), leading to diimide 17. This reaction is performed in a suitable solvent, e.g., acetonitrile or dichloromethane, at temperatures between −30° C. and +40° C.

The reaction can be performed either in batch mode or, more preferably, in a continuous flow reactor. The dimeric products can be formed as a mixture of stereoisomers (i.e., 3aS,3bS,6aR,6bR-17 and 3aS,3bR,6aS,6bR-17), which can be separated, e.g., by crystallisation.

In step 2, scheme 1, diimide 17 is reduced to the corresponding diamine 18, using reagents and conditions known in the art. The reaction is performed, e.g., using lithium aluminum hydride, in a solvent such as diethyl ether or tetrahydrofuran, at temperatures between 0° C. and the boiling point of the solvent.

In step 3, scheme 1, the benzyl groups of 18 are removed, leading to diamine 12, using methods and reagents known in the art, e.g., by catalytic hydrogenation. The reaction is performed in a suitable solvent, e.g., methanol or ethanol, at hydrogen pressures between 1 bar and 100 bar, at temperatures between 0° C. and 100° C., in the presence of a suitable catalyst, e.g., palladium on activated charcoal.

Also an embodiment of the present invention is a process to prepare a compound of formula (I) as defined above comprising the reaction of a compound of formula (II) in the presence of a compound of formula (III);

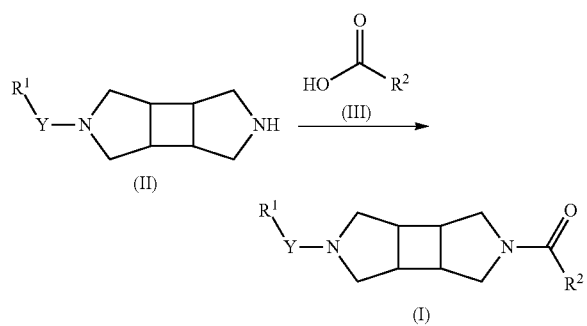

wherein $R^1$, $R^2$, A and Y are as defined above.

In particular, in the presence of a coupling agent such as O-(7-azabenzotriazol-1-yl)-N,N,N',N'-tetramethyluronium hexafluoro-phosphate, in a solvent such as N,N-dimethylformamide, in the presence of a base such as 4-methylmorpholine and at a temperature comprised between −78° C. and reflux, particularly between −10° C. and room temperature.

Also an object of the present invention is a compound according to formula (I) as described herein for use as a therapeutically active substance.

Likewise an object of the present invention is a pharmaceutical composition comprising a compound according to formula (I) as described herein and a therapeutically inert carrier.

A more particular object of the invention is the use of a compound according to formula (I) as described herein for the treatment or prophylaxis of fibrotic diseases, cancer and ocular conditions.

A furthermore particular object of the invention is the use of a compound according to formula (I) as described herein for the treatment or prophylaxis of fibrotic diseases and ocular conditions.

Renal conditions include, but are not limited to, acute kidney injury and chronic renal disease with and without proteinuria including end-stage renal disease (ESRD). In more detail, this includes decreased creatinine clearance and decreased glomerular filtration rate, micro-albuminuria, albuminuria and proteinuria, glomerulosclerosis with expansion of reticulated mesangial matrix with or without significant hypercellularity (particularly diabetic nephropathy and amyloidosis), focal thrombosis of glomerular capillaries (particularly thrombotic microangiopathies), global fibrinoid necrosis, ischemic lesions, malignant nephrosclerosis (such as ischemic retraction, reduced renal blood flow and renal arteriopathy), swelling and proliferation of intracapillary (endothelial and mesangial) and/or extracapillary cells (crescents) like in glomerular nephritis entities, focal segmental glomerular sclerosis, IgA nephropathy, vasculitides/systemic diseases as well as acute and chronic kidney transplant rejection.

Liver conditions include, but are not limited to, liver cirrhosis, hepatic congestion, cholestatic liver disease including pruritus, nonalcoholic steatohepatitis and acute and chronic liver transplant rejection.

Inflammatory conditions include, but are not limited to, arthritis, osteoarthritis, multiple sclerosis, systemic lupus erythematodes, inflammatory bowel disease, abnormal evacuation disorder and the like as well as inflammatory airways diseases such as idiopathic pulmonary fibrosis (IPF), chronic obstructive pulmonary disease (COPD) or chronic asthma bronchiale.

Further conditions of the respiratory system include, but are not limited to, other diffuse parenchymal lung diseases of different etiologies including iatrogenic drug-induced fibrosis, occupational and/or environmental induced fibrosis, systemic diseases and vasculitides, granulomatous diseases (sarcoidosis, hypersensitivity pneumonia), collagen vascular disease, alveolar proteinosis, Langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease), radiation induced fibrosis, silicosis, asbestos induced pulmonary fibrosis or acute respiratory distress syndrome (ARDS).

Conditions of the nervous system include, but are not limited to, neuropathic pain, schizophrenia, neuro-inflammation (e.g. astrogliosis), peripheral and/or autonomic (diabetic) neuropathies and the like.

Vascular conditions include, but are not limited to, atherosclerosis, thrombotic vascular disease as well as thrombotic microangiopathies, proliferative arteriopathy (such as swollen myointimal cells surrounded by mucinous extracellular matrix and nodular thickening), atherosclerosis, decreased vascular compliance (such as stiffness, reduced ventricular compliance and reduced vascular compliance), endothelial dysfunction and the like.

Cardiovascular conditions include, but are not limited to, acute coronary syndrome, coronary heart disease, myocardial infarction, arterial and pulmonary hypertension, cardiac arrhythmia such as atrial fibrillation, stroke and other vascular damage.

Fibrotic diseases include, but are not limited to myocardial and vascular fibrosis, renal fibrosis, liver fibrosis, pulmonary fibrosis, skin fibrosis, scleroderma and encapsulating peritonitis. A particular fibrotic disease is idiopathic pulmonary fibrosis.

In a particular embodiment, the compounds of formula (I) or their pharmaceutically acceptable salts and esters can be used for the treatment or prophylaxis of organ or skin fibrosis.

In another embodiment, the fibrotic disease is renal tubulo-interstitial fibrosis or glomerulosclerosis.

In another embodiment, the fibrotic disease is non-alcoholic liver steatosis, liver fibrosis or liver cirrhosis.

In another embodiment, the fibrotic disease is idiopathic pulmonary fibrosis.

Cancer and cancer metastasis include, but are not limited to, breast cancer, ovarian cancer, lung cancer, prostate cancer, mesothelioma, glioma, hepatic carcinoma, gastrointestinal cancers and progression and metastatic aggressiveness thereof.

Ocular conditions include, but are not limited to, proliferative and non-proliferative (diabetic) retinopathy, dry and wet age-related macular degeneration (AMD), (diabetic) macular edema, central arterial/venous occlusion, traumatic injury, glaucoma and the like. A particular ocular condition is glaucoma.

Metabolic conditions include, but are not limited to, obesity and diabetes.

In another embodiment, the compounds of formula (I) or their pharmaceutically acceptable salts and esters can be used for the treatment or prophylaxis of cholestatic or non-cholestatic chronic pruritus.

The present invention also relates to the use of a compound according to formula (I) as described herein for the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection.

The present invention also particularly relates to the use of a compound according to formula (I) as described herein for the treatment or prophylaxis of fibrotic diseases, cancer and ocular conditions.

The present invention also more particularly relates to the use of a compound according to formula (I) as described herein for the treatment or prophylaxis of fibrotic diseases and ocular conditions.

Another embodiment of the present invention is a compound according to formula (I) as described herein for the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection.

Another particular embodiment of the present invention is a compound according to formula (I) as described herein for the treatment or prophylaxis fibrotic diseases, cancer and ocular conditions.

Another more particular embodiment of the present invention is a compound according to formula (I) as described herein for the treatment or prophylaxis fibrotic diseases and ocular conditions.

The present invention also relates to the use of a compound according to formula (I) as described herein for the preparation of a medicament for the treatment or prophylaxis renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection.

The present invention also particularly relates to the use of a compound according to formula (I) as described herein for the preparation of a medicament for the treatment or prophylaxis of fibrotic diseases, cancer and ocular conditions.

The present invention also further particularly relates to the use of a compound according to formula (I) as described herein for the preparation of a medicament for the treatment or prophylaxis of fibrotic diseases and ocular conditions.

Also an object of the invention is a method for the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection, which method comprises administering an effective amount of a compound according to formula (I) as described herein.

Also a particular object of the invention is a method for the treatment or prophylaxis of fibrotic diseases, cancer and ocular conditions, which method comprises administering an effective amount of a compound according to formula (I) as described herein.

Also a more particular object of the invention is a method for the treatment or prophylaxis of fibrotic diseases and ocular conditions, which method comprises administering an effective amount of a compound according to formula (I) as described herein.

In a particular embodiment, the renal condition is selected from the group consisting of acute kidney injury, chronic kidney disease, diabetic nephropathy, acute kidney transplant rejection and chronic allograft nephropathy.

In another particular embodiment, the renal condition is acute kidney injury.

In another particular embodiment, the renal condition is chronic kidney disease.

In a further particular embodiment, the renal condition is diabetic nephropathy.

In another particular embodiment, the renal condition is acute kidney transplant rejection.

In another particular embodiment, the renal condition is chronic allograft nephropathy.

In a particular embodiment, the liver condition is acute and chronic liver transplant rejection In a particular embodiment, the inflammatory condition is arthritis.

In a particular embodiment, the condition of the nervous system is neuropathic pain.

In another embodiment, the fibrotic disease is encapsulating peritonitis

In another embodiment, the fibrotic disease is idiopathic pulmonary fibrosis.

In another embodiment, the fibrotic disease is non-alcoholic liver steatosis, liver fibrosis or liver cirrhosis.

Also an embodiment of the present invention are compounds of formula (I) as described herein, when manufactured according to any one of the described processes.

Assay Procedures

Production of Human Full Length ATX, with and without His Tag

Autotaxin (ATX-ENPP2) Cloning:

cDNA was prepared from commercial human hematopoietic cells total RNA and used as template in overlapping PCR to generate a full length human ENPP2 ORF with or without a 3'-6×His tag. These full length inserts were cloned into the pcDNA3.1V5-His TOPO (Invitrogen) vector. The DNA sequences of several single clones were verified. The DNA from a correct full length clone was used to transfect Hek293 cells for verification of protein expression. The sequence of the encoded ENPP2 conforms to Swissprot entry Q13822, with or without the additional C-terminal 6×His tag.

ATX Fermentation:

Recombinant protein was produced by large-scale transient transfection in 20 L controlled stirred tank bioreactors (Sartorius). During cell growth and transfection, temperature, stirrer speed, pH and dissolved oxygen concentration were maintained at 37° C., 120 rpm, 7.1 and 30% DO, respectively. FreeStyle 293-F cells (Invitrogen) were cultivated in suspension in FreeStyle 293 medium (Invitrogen) and transfected at ca. 1-1.5×10E6 cells/mL with above plasmid DNAs using X-tremeGENE Ro-1539 (commercial product, Roche Diagnostics) as complexing agent. Cells were fed a concentrated nutrient solution (J Immunol Methods 194 (1996), 19, 1-199 (page 193)) and induced by sodium butyrate (2 mM) at 72 h post-transfection and harvested at 96 h post-transfection. Expression was analyzed by Western Blot, enzymatic assay and/or analytical IMAC chromatography. After cooling the cell suspension to 4° C. in a flow-through heat exchanger, cell separation and sterile filtration of supernatant was performed by filtration through Zeta Plus 60M02 E16 (Cuno) and Sartopore 2 XLG (Sartorius) filter units. The supernatant was stored at 4° C. prior to purification.

ATX Purification:

20 liter of culture supernatant were conditioned for ultrafiltration by adding Brij 35 to a final concentration of 0.02% and by adjusting the pH to 7.0 using 1 M HCl. Then the supernatant was first microfiltred through a 0.2 μm Ultran-Pilot Open Channel PES filter (Whatman) and afterwards concentrated to 1 liter through an Ultran-Pilot Screen Channel PES filter with 30 kDa MWCO (Whatman). Prior to IMAC chromatography, $NiSO_4$ was added to a final concentration of 1 mM. The cleared supernatant was then applied to a HisTrap column (GE Healthcare) previously equilibrated in 50 mM $Na_2HPO_4$ pH 7.0, 0.5 M NaCl, 10% glycerol, 0.3% CHAPS, 0.02% $NaN_3$. The column was washed stepwise with the same buffer containing 20 mM, 40 mM and 50 mM imidazole, respectively. The protein was subsequently eluted using a linear gradient to 0.5 M imidazole in 15 column volumes. ATX containing fractions were pooled and concentrated using an Amicon cell equipped with a 30 kDa PES filter membrane. The protein was further purified by size exclusion chromatography on Superdex S-200 prep grade (XK 26/100) (GE Healthcare) in 20 mM BICINE pH 8.5, 0.15 M NaCl, 10% glycerol, 0.3% CHAPS, 0.02% $NaN_3$. Final yield of protein after purification was 5-10 mg ATX per liter of culture supernatant. The protein was stored at −80° C.

Human ATX Enzyme Inhibition Assay

ATX inhibition was measured by a fluorescence quenching assay using a specifically labeled substrate analogue (MR121 substrate). To obtain this MR121 substrate, BOC and TBS protected 6-amino-hexanoic acid (R)-3-({2-[3-(2-{2-[2-(2-amino-ethoxy)-ethoxy]-ethoxy}-ethoxy)-propionylamino]-ethoxy}-hydroxy-phosphoryloxy)-2-hydroxy-propyl ester (Ferguson et al., Org Lett 2006, 8 (10), 2023) was labeled with MR121 fluorophore (CAS 185308-24-1, 1-(3-carboxypropyl)-11-ethyl-1,2,3,4,8,9,10,11-octahydro-dipyrido[3,2-b:2',3'-i]phenoxazin-13-ium) on the free amine of the ethanolamine side and then, after deprotection, subsequently with tryptophan on the side of the aminohexanoic acid.

Assay working solutions were made as follows:

Assay buffer (50 mM Tris-HCl, 140 mM NaCl, 5 mM KCl, 1 mM $CaCl_2$, 1 mM $MgCl_2$, 0.01% Triton-X-100, pH 8.0;

ATX solution: ATX (human His-tagged) stock solution (1.08 mg/mL in 20 mM bicine, pH 8.5, 0.15 M NaCl, 10% glycerol, 0.3% CHAPS, 0.02% $NaN_3$), diluted to 1.4-2.5× final concentration in assay buffer;

MR121 substrate solution: MR121 substrate stock solution (800 μM MR121 substrate in DMSO), diluted to 2-5× final concentration in assay buffer.

Test compounds (10 mM stock in DMSO, 8 μL) were obtained in 384 well sample plates (Corning Costar #3655) and diluted with 8 μL DMSO. Row-wise serial dilutions were made by transferring 8 μL cpd solution to the next row up to row O. The compound and control solutions were mixed five times and 2 μL were transferred to 384 well assay plates (Corning Costar #3702). Then, 15 μL of 41.7 nM ATX solution was added (30 nM final concentration), mixed five times and then incubated for 15 minutes at 30° C. 10 μL of MR121 substrate solution was added (1 μM final concentration), mixed 30 times and then incubated for 15 minutes at 30'C. Fluorescence was then measured every 2 minutes for 1 hour (Perkin Elmer plate: vision multimode reader); light intensity: 2.5%; exp. time: 1.4 sec, Filter: Fluo_630/690 nm) and $IC_{50}$ values were calculated from these readouts.

$IC_{50}$ values for the examples of this invention are given in the table below:

| Example | IC50 (μM) |
| --- | --- |
| 1 | 0.034 |
| 1.001 | 0.011 |
| 1.002 | 0.064 |
| 1.003 | 0.0085 |
| 1.004 | 0.017 |
| 1.005 | 0.12 |
| 1.006 | 0.008 |
| 1.007 | 0.062 |
| 1.008 | 0.036 |
| 1.009 | 0.008 |
| 1.010 | 0.016 |
| 1.011 | 0.008 |
| 1.012 | 0.086 |
| 1.013 | 0.054 |
| 1.014 | 0.045 |
| 1.015 | 0.011 |
| 1.016 | 0.017 |
| 1.017 | 0.008 |
| 1.018 | 0.016 |
| 1.019 | 0.0115 |
| 1.020 | 0.006 |
| 1.021 | 0.265 |
| 1.022 | 0.155 |
| 1.023 | 1.473 |
| 1.024 | 0.377 |
| 1.025 | 0.0085 |
| 1.026 | 0.0115 |
| 1.027 | 0.828 |
| 1.028 | 2.834 |
| 1.029 | 0.07 |
| 1.030 | 0.104 |
| 1.031 | 0.224 |
| 1.032 | 0.013 |
| 1.033 | 0.104 |
| 1.034 | 0.489 |
| 1.035 | 0.243 |
| 1.036 | 0.13 |
| 1.037 | 0.1587 |
| 1.038 | 0.687 |
| 1.039 | 3.33 |
| 1.040 | 8.674 |

-continued

| Example | IC50 (µM) |
|---|---|
| 1.041 | 0.538 |
| 1.042 | 0.632 |
| 1.043 | 1.406 |
| 1.044 | 0.013 |
| 1.045 | 0.011 |
| 1.046 | 0.028 |
| 1.047 | 0.205 |
| 1.048 | 0.208 |
| 1.049 | 0.004 |
| 1.050 | 0.008 |
| 1.051 | 0.007 |
| 1.052 | 0.0035 |
| 1.053 | 0.014 |
| 1.054 | 0.0592 |
| 1.055 | 0.022 |
| 1.056 | 0.029 |
| 1.057 | 0.0077 |
| 1.058 | 0.0053 |
| 1.059 | 0.0013 |
| 1.060 | 0.0047 |
| 1.061 | 0.0405 |
| 1.062 | 0.009 |
| 1.063 | 0.001 |
| 1.064 | 0.001 |
| 1.065 | 0.0065 |
| 1.066 | 0.005 |
| 1.067 | 0.005 |
| 1.068 | 0.0143 |
| 1.069 | 0.008 |
| 1.070 | 0.004 |
| 1.071 | 0.0035 |
| 1.072 | 0.006 |
| 1.073 | 0.0035 |
| 1.074 | 0.005 |
| 1.075 | 0.02 |
| 1.076 | 0.0125 |
| 1.077 | 0.0075 |
| 1.078 | 0.0035 |
| 1.079 | 0.0315 |
| 1.080 | 0.0025 |
| 1.081 | 0.0075 |
| 1.082 | 0.003 |
| 1.083 | 0.1535 |
| 1.084 | 0.005 |
| 1.085 | 0.0027 |
| 1.086 | 0.017 |
| 1.087 | 0.0153 |
| 1.088 | 0.0413 |
| 1.089 | 0.02 |
| 1.090 | 0.019 |
| 1.091 | 0.017 |
| 1.092 | 0.018 |
| 1.093 | 0.017 |
| 1.094 | 0.077 |
| 1.095 | 0.032 |
| 1.096 | 0.012 |
| 1.097 | 0.025 |
| 1.098 | 0.859 |
| 1.099 | 0.277 |
| 1.100 | 0.01 |
| 1.101 | 4.433 |
| 1.102 | 0.992 |
| 1.103 | 0.027 |
| 1.104 | 0.01 |
| 1.105 | 0.008 |
| 1.106 | 0.169 |
| 1.107 | 0.141 |
| 1.108 | 0.006 |
| 1.109 | 0.301 |
| 1.110 | 0.0325 |
| 1.111 | 0.3305 |
| 2 | 0.014 |
| 2.001 | 0.0045 |
| 3 | 0.173 |
| 3.001 | 0.232 |
| 4 | 0.07 |

Compounds of formula (I) and their pharmaceutically acceptable salts or esters thereof as described herein have $IC_{50}$ values between 0.00001 µM and 1000 µM, particular compounds have $IC_{50}$ values between 0.0005 µM and 500 µM, further particular compounds have $IC_{50}$ values between 0.0005 µM and 50 µM, more particular compounds have $IC_{50}$ values between 0.0005 µM and 5 µM. These results have been obtained by using the enzymatic assay described above.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parenterally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided preferably into 1-3 individual doses, which can consist, for example, of the same amounts, should it be appropriate. It will, however, be clear that the upper limit given herein can be exceeded when this is shown to be indicated.

The invention is illustrated hereinafter by Examples, which have no limiting character.

In case the preparative examples are obtained as a mixture of enantiomers, the pure enantiomers can be obtained by methods described herein or by methods known to those skilled in the art, such as e.g. chiral chromatography or crystallization.

EXAMPLES

All examples and intermediates were prepared under nitrogen atmosphere if not specified otherwise.

Abbreviations aq.=aqueous; CAS-RN=Chemical Abstracts Service Registry Number; e.r.=enantiomeric ratio; HPLC=high performance liquid chromatography; MS=mass spectrum; NMR=nuclear magnetic resonance spectrum; sat.=saturated

Example 1

[(3aS,3bS,6aR,6bR)-5-(1H-Benzotriazole-5-carbonyl)-octahydro-cyclobuta[1,2-c;3,4-c']dipyrrol-2-yl]-(6-chloro-naphthalen-2-yl)-methanone

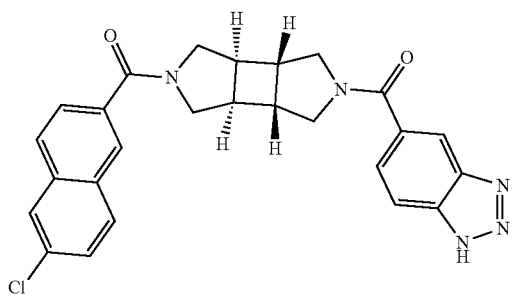 [SMILES: O=C(c1ccc2cc(Cl)ccc2c1)N1C[C@@H]2[C@H](C1)[C@H]1CN(C(=O)c3ccc4[nH]nnc4c3)C[C@@H]21]

To a solution of (3aS,3bS,6aR,6bR)-decahydro-cyclobuta[1,2-c;3,4-c']dipyrrole (intermediate 1; 30 mg, 217 μmol) in N,N-dimethylformamide (3.5 ml) were added N-methylmorpholine (110 mg, 1.09 mmol), 6-chloro-naphthalene-2-carboxylic acid (CAS-RN 5042-97-7; 44.9 mg, 217 μmol) and O-(7-azabenzotriazol-1-yl)-N,N,N',N'-tetramethyluronium hexafluoro-phosphate (82.5 mg, 217 μmol). After stirring for 8 h at room temperature 1H-benzo[d][1,2,3]triazole-5-carboxylic acid (35.4 mg, 217 μmol, Eq: 1.00) and O-(7-azabenzotriazol-1-yl)-N,N,N',N'-tetramethyluronium hexafluoro-phosphate (82.5 mg, 217 μmol) were added, then after 16 h the reaction mixture was partitioned between sat. aq. ammonium chloride solution and ethyl acetate. The organic layer was washed with brine, dried over magnesium sulfate, filtered and evaporated. Chromatography (silica gel; gradient dichloromethane to dichloromethane/methanol/25% aq. ammonia solution 90:10:0.25) produced the title compound (51 mg, 50%). Off-white solid, MS: 472.5 (M+H)$^+$.

The following examples were produced in analogy to example 1, replacing 6-chloro-naphthalene-2-carboxylic acid and 1H-benzo[d][1,2,3]triazole-5-carboxylic acid by carboxylic acid 1 and carboxylic acid 2, respectively.

| Ex. | Systematic Name | carboxylic acid 1 | carboxylic acid 2 | MS, m/e |
|---|---|---|---|---|
| 1.001 | 1-[(3aS,3bR,6aS,6bR)-5-(1H-benzotriazole-5-carbonyl)-octahydro-cyclobuta[1,2-c;3,4-c']dipyrrol-2-yl]-3-(4-trifluoromethoxy-phenyl)-propan-1-one | 4-(trifluoromethoxy)-hydrocinnamic acid (CAS-RN 886499-74-7) | 1H-benzo[d]-[1,2,3]triazole-5-carboxylic acid | 500.6 (M + H)$^+$ |
| 1.002 | [(3aS,3bS,6aR,6bR)-5-(1H-benzotriazole-5-carbonyl)-octahydro-cyclobuta[1,2-c;3,4-c']dipyrrol-2-yl]-(4'-fluoro-biphenyl-4-yl)-methanone | 4'-fluorobiphenyl-4-carboxylic acid (CAS-RN 5731-10-2) | 1H-benzo[d]-[1,2,3]triazole-5-carboxylic acid | 482.5 (M + H)$^+$ |

-continued

| Ex. | Systematic Name | carboxylic acid 1 | carboxylic acid 2 | MS, m/e |
|---|---|---|---|---|
| 1.003 | (E)-1-[(3aS,3bR,6aS,6bR)-5-(1H-benzotriazole-5-carbonyl)-octahydro-cyclobuta[1,2-c;3,4-c']dipyrrol-2-yl]-3-(4-trifluoromethoxy-phenyl)-propenone | 4-(trifluoromethoxy)-cinnamic acid (CAS-RN 199679-35-1) | 1H-benzo[d]-[1,2,3]triazole-5-carboxylic acid | 498.5 (M + H)+ |
| 1.004 | [(3aS,3bS,6aR,6bR)-5-(1H-benzotriazole-5-carbonyl)-octahydro-cyclobuta[1,2-c;3,4-c']dipyrrol-2-yl]-(6-bromo-naphthalen-2-yl)-methanone | 6-bromo-2-naphthoic acid (CAS-RN 5773-80-8) | 1H-benzo[d]-[1,2,3]triazole-5-carboxylic acid | 514.8 (M − H)− |
| 1.005 | [(3aS,3bS,6aR,6bR)-5-(1H-benzotriazole-5-carbonyl)-octahydro-cyclobuta[1,2-c;3,4-c']dipyrrol-2-yl]-(6-methoxy-naphthalen-2-yl)-methanone | 6-methoxy-2-naphthoic acid (CAS-RN 2471-70-7) | 1H-benzo[d]-[1,2,3]triazole-5-carboxylic acid | 468.7 (M + H)+ |

-continued

| Ex. | Systematic Name | carboxylic acid 1 | carboxylic acid 2 | MS, m/e |
|---|---|---|---|---|
| 1.006 | (E)-1-[(3aS,3bS,6aR,6bR)-5-((R)-4,5,6,7-tetrahydro-1H-benzotriazole-5-carbonyl)-octahydro-cyclobuta[1,2-c;3,4-c']dipyrrol-2-yl]-3-(4-trifluoromethoxy-phenyl)-propenone | 4-(trifluoromethoxy)-cinnamic acid (CAS-RN 199679-35-1) | (+)-(R)-4,5,6,7-tetrahydro-1H-benzo[d]-[1,2,3]triazole-5-carboxylic acid (intermediate 11) | 502.7 (M + H)+ |
| 1.007 | 6-[(3aS,3bS,6aR,6bR)-5-(1H-benzotriazole-5-carbonyl)-octahydro-cyclobuta[1,2-c;3,4-c']dipyrrole-2-carbonyl]-naphthalene-2-carbonitrile | 6-cyano-2-naphthoic acid (CAS-RN 5159-60-4) | 1H-benzo[d]-[1,2,3]triazole-5-carboxylic acid | 463.5 (M + H)+ |
| 1.008 | 1-[(3aR,3bS,6aR,6bS)-5-(1H-benzotriazole-5-carbonyl)-octahydro-cyclobuta[1,2-c;3,4-c']dipyrrol-2-yl]-2-(4-trifluoromethoxy-phenoxy)-ethanone | 2-(4-(trifluoromethoxy)-phenoxy)acetic acid (CAS-RN 72220-50-9) | 1H-benzo[d]-[1,2,3]triazole-5-carboxylic acid | 502.4 (M + H)+ |

-continued

| Ex. | Systematic Name | carboxylic acid 1 | carboxylic acid 2 | MS, m/e |
|---|---|---|---|---|
| 1.009 | 1-[(3aR,3bS,6aR,6bS)-5-(1H-benzotriazole-5-carbonyl)-octahydro-cyclobuta[1,2-c;3,4-c']dipyrrol-2-yl]-2-(2-isopropyl-phenoxy)-ethanone | 2-(2-isopropyl-phenoxy)acetic acid (CAS-RN 25141-58-6) | 1H-benzo[d]-[1,2,3]triazole-5-carboxylic acid | 460.4 (M + H)+ |
| 1.010 | [(3aR,3bS,6aR,6bS)-5-(1H-benzotriazole-5-carbonyl)-octahydro-cyclobuta[1,2-c;3,4-c']dipyrrol-2-yl]-(5-trifluoromethoxy-1H-indol-2-yl)-methanone | 5-(trifluoro-methoxy)-1H-indole-2-carboxylic acid (CAS-RN 175203-84-6) | 1H-benzo[d]-[1,2,3]triazole-5-carboxylic acid | 511.0 (M + H)+ |
| 1.011 | [(3aR,3bS,6aR,6bS)-5-(1H-benzotriazole-5-carbonyl)-octahydro-cyclobuta[1,2-c;3,4-c']dipyrrol-2-yl]-(6-trifluoromethoxy-1H-indol-2-yl)-methanone | 6-(trifluoro-methoxy)-1H-indole-2-carboxylic acid (CAS-RN 923259-70-5) | 1H-benzo[d]-[1,2,3]triazole-5-carboxylic acid | 511.7 (M + H)+ |
| 1.012 | [(3aS,3bS,6aR,6bR)-5-(1H-benzotriazole-5-carbonyl)-octahydro-cyclobuta[1,2-c;3,4-c']dipyrrol-2-yl]-naphthalen-2-yl-methanone | 2-naphthoic acid (CAS-RN 93-09-4) | 1H-benzo[d]-[1,2,3]triazole-5-carboxylic acid | 438.7 (M + H)+ |

-continued

| Ex. | Systematic Name | carboxylic acid 1 | carboxylic acid 2 | MS, m/e |
|---|---|---|---|---|
| 1.013 | [(3aS,3bS,6aR,6bR)-5-(1H-benzotriazole-5-carbonyl)-octahydro-cyclobuta[1,2-c;3,4-c']dipyrrol-2-yl]-(6-methyl-naphthalen-2-yl)-methanone | 6-methyl-2-naphthoic acid (CAS-RN 5774-08-3) | 1H-benzo[d]-[1,2,3]triazole-5-carboxylic acid | 452.6 (M + H)+ |
| 1.014 | [(3aS,3bS,6aR,6bR)-5-(1H-benzotriazole-5-carbonyl)-octahydro-cyclobuta[1,2-c;3,4-c']dipyrrol-2-yl]-(7-methyl-naphthalen-2-yl)-methanone | 7-methyl-2-naphthoic acid (CAS-RN 5159-64-8) | 1H-benzo[d]-[1,2,3]triazole-5-carboxylic acid | 452.7 (M + H)+ |
| 1.015 | [(3aS,3bS,6aR,6bR)-5-(1H-benzotriazole-5-carbonyl)-octahydro-cyclobuta[1,2-c;3,4-c']dipyrrol-2-yl]-(6-phenyl-naphthalen-2-yl)-methanone | 6-phenyl-2-naphthoic acid (CAS-RN 855207-53-3) | 1H-benzo[d]-[1,2,3]triazole-5-carboxylic acid | 514.6 (M + H)+ |

-continued

| Ex. | Systematic Name | carboxylic acid 1 | carboxylic acid 2 | MS, m/e |
|---|---|---|---|---|
| 1.016 | (6-bromo-naphthalen-2-yl)-[(3aR,3bS,6aR,6bS)-5-((R)-4,5,6,7-tetrahydro-1H-benzotriazole-5-carbonyl)-octahydro-cyclobuta[1,2-c;3,4-c']dipyrrol-2-yl]-methanone | 6-bromo-2-naphthoic acid (CAS-RN 5773-80-8) | (+)-(R)-4,5,6,7-tetrahydro-1H-benzo[d]-[1,2,3]triazole-5-carboxylic acid (intermediate 11) | 520.5 (M + H)+ |
| 1.017 | [(3aS,3bS,6aR,6bR)-5-(1H-benzotriazole-5-carbonyl)-octahydro-cyclobuta[1,2-c;3,4-c']dipyrrol-2-yl]-(4'-chloro-biphenyl-4-yl)-methanone | 4'-chlorobiphenyl-4-carboxylic acid (CAS-RN 5748-41-4) | 1H-benzo[d]-[1,2,3]triazole-5-carboxylic acid | 498.6 (M + H)+ |
| 1.018 | (4'-chloro-biphenyl-4-yl)-[(3aR,3bS,6aR,6bS)-5-((R)-4,5,6,7-tetrahydro-1H-benzotriazole-5-carbonyl)-octahydro-cyclobuta[1,2-c;3,4-c']dipyrrol-2-yl]-methanone | 4'-chlorobiphenyl-4-carboxylic acid (CAS-RN 5748-41-4) | (+)-(R)-4,5,6,7-tetrahydro-1H-benzo[d]-[1,2,3]triazole-5-carboxylic acid (intermediate 11) | 502.5 (M + H)+ |

-continued

| Ex. | Systematic Name | carboxylic acid 1 | carboxylic acid 2 | MS, m/e |
|---|---|---|---|---|
| 1.019 | [(3aR,3bS,6aR,6bS)-5-((R)-4,5,6,7-tetrahydro-1H-benzotriazole-5-carbonyl)-octahydro-cyclobuta[1,2-c;3,4-c']dipyrrol-2-yl]-(5-trifluoromethoxy-1H-indol-2-yl)-methanone | 5-(trifluoromethoxy)-1H-indole-2-carboxylic acid (CAS-RN 175203-84-6) | (+)-(R)-4,5,6,7-tetrahydro-1H-benzo[d][1,2,3]triazole-5-carboxylic acid (intermediate 11) | 515.7 (M + H)+ |
| 1.020 | [(3aR,3bS,6aR,6bS)-5-((R)-4,5,6,7-tetrahydro-1H-benzotriazole-5-carbonyl)-octahydro-cyclobuta[1,2-c;3,4-c']dipyrrol-2-yl]-(6-trifluoromethoxy-1H-indol-2-yl)-methanone | 6-(trifluoromethoxy)-1H-indole-2-carboxylic acid (CAS-RN 923259-70-5) | (+)-(R)-4,5,6,7-tetrahydro-1H-benzo[d][1,2,3]triazole-5-carboxylic acid (intermediate 11) | 515.7 (M + H)+ |
| 1.021 | [(3aS,3bS,6aR,6bR)-5-(1H-benzotriazole-5-carbonyl)-octahydro-cyclobuta[1,2-c;3,4-c']dipyrrol-2-yl]-(3-methoxy-naphthalen-2-yl)-methanone | 3-methoxy-2-naphthoic acid (CAS-RN 883-62-5) | 1H-benzo[d][1,2,3]triazole-5-carboxylic acid | 468.6 (M + H)+ |

-continued

| Ex. | Systematic Name | carboxylic acid 1 | carboxylic acid 2 | MS, m/e |
|---|---|---|---|---|
| 1.022 | [(3aS,3bS,6aR,6bR)-5-(1H-benzotriazole-5-carbonyl)-octahydro-cyclobuta[1,2-c;3,4-c']dipyrrol-2-yl]-(1-methoxy-naphthalen-2-yl)-methanone | 1-methoxy-2-naphthoic acid (CAS-RN 883-21-6) | 1H-benzo[d]-[1,2,3]triazole-5-carboxylic acid | 468.6 (M + H)+ |
| 1.023 | [(3aR,3bS,6aR,6bS)-5-(1H-benzotriazole-5-carbonyl)-octahydro-cyclobuta[1,2-c;3,4-c']dipyrrol-2-yl]-(1H-indol-2-yl)-methanone | 1H-indole-2-carboxylic acid (CAS-RN 1477-50-5) | 1H-benzo[d]-[1,2,3]triazole-5-carboxylic acid | 427.5 (M + H)+ |
| 1.024 | [(3aR,3bS,6aR,6bS)-5-(1H-benzotriazole-5-carbonyl)-octahydro-cyclobuta[1,2-c;3,4-c']dipyrrol-2-yl]-(1-methyl-1H-indol-2-yl)-methanone | 1-methyl-1H-indole-2-carboxylic acid (CAS-RN 16136-58-6) | 1H-benzo[d]-[1,2,3]triazole-5-carboxylic acid | 441.5 (M + H)+ |
| 1.025 | [(3aS,3bS,6aR,6bR)-5-(1H-benzotriazole-5-carbonyl)-octahydro-cyclobuta[1,2-c;3,4-c']dipyrrol-2-yl]-(4-cyclopropylmethoxy-naphthalen-2-yl)-methanone | 4-(cyclopropyl-methoxy)-2-naphthoic acid | 1H-benzo[d]-[1,2,3]triazole-5-carboxylic acid | 508.6 (M + H)+ |

| Ex. | Systematic Name | carboxylic acid 1 | carboxylic acid 2 | MS, m/e |
|---|---|---|---|---|
| 1.026 | [(3aS,3bS,6aR,6bR)-5-(1H-benzotriazole-5-carbonyl)-octahydro-cyclobuta[1,2-c;3,4-c']dipyrrol-2-yl]-(4-methoxy-naphthalen-2-yl)-methanone | 4-methoxy-2-naphthoic acid (CAS-RN 5773-93-3) | 1H-benzo[d]-[1,2,3]triazole-5-carboxylic acid | 468.5 (M + H)+ |
| 1.027 | 2-[(3aR,3bS,6aR,6bS)-5-(1H-benzotriazole-5-carbonyl)-octahydro-cyclobuta[1,2-c;3,4-c']dipyrrole-2-carbonyl]-1H-indole-5-carbonitrile | 5-cyano-1H-indole-2-carboxylic acid (CAS-RN 169463-44-9) | 1H-benzo[d]-[1,2,3]triazole-5-carboxylic acid | 452.6 (M + H)+ |
| 1.028 | [(3aS,3bS,6aR,6bR)-5-(1H-benzotriazole-5-carbonyl)-octahydro-cyclobuta[1,2-c;3,4-c']dipyrrol-2-yl]-(3-methoxy-phenyl)-methanone | 3-methoxy-benzoic acid (CAS-RN 586-38-9) | 1H-benzo[d]-[1,2,3]triazole-5-carboxylic acid | 418.5 (M + H)+ |
| 1.029 | [(3aR,3bS,6aR,6bS)-5-(1H-benzotriazole-5-carbonyl)-octahydro-cyclobuta[1,2-c;3,4-c']dipyrrol-2-yl]-(4-methoxy-quinolin-2-yl)-methanone | 4-methoxy-2-quinoline-carboxylic acid (CAS-RN 15733-83-2) | 1H-benzo[d]-[1,2,3]triazole-5-carboxylic acid | 469.5 (M + H)+ |

-continued

| Ex. | Systematic Name | carboxylic acid 1 | carboxylic acid 2 | MS, m/e |
|---|---|---|---|---|
| 1.030 | [(3aR,3bS,6aR,6bS)-5-(1H-benzotriazole-5-carbonyl)-octahydro-cyclobuta[1,2-c;3,4-c']dipyrrol-2-yl]-[2-(4-chloro-phenyl)-5-methyl-oxazol-4-yl]-methanone | 2-(4-chlorophenyl)-5-methyl-1,3-oxazole-4-carboxylic acid (CAS-RN 2940-23-0) | 1H-benzo[d]-[1,2,3]triazole-5-carboxylic acid | 503.6 (M + H)+ |
| 1.031 | [(3aS,3bR,6aS,6bR)-5-(1H-benzotriazole-5-carbonyl)-octahydro-cyclobuta[1,2-c;3,4-c']dipyrrol-2-yl]-(1,2,3,4-tetrahydro-naphthalen-2-yl)-methanone | 1,2,3,4-tetrahydro-2-naphthoic acid (CAS-RN 53440-12-3) | 1H-benzo[d]-[1,2,3]triazole-5-carboxylic acid | 442.7 (M + H)+ |
| 1.032 | [(3aR,3bS,6aR,6bS)-5-(1H-benzotriazole-5-carbonyl)-octahydro-cyclobuta[1,2-c;3,4-c']dipyrrol-2-yl]-(1-methyl-5-trifluoromethoxy-1H-indol-2-yl)-methanone | 1-methyl-5-(trifluoromethoxy)-1H-indole-2-carboxylic acid (CAS-RN 1257122-42-1) | 1H-benzo[d]-[1,2,3]triazole-5-carboxylic acid | 525.7 (M + H)+ |

-continued

| Ex. | Systematic Name | carboxylic acid 1 | carboxylic acid 2 | MS, m/e |
|---|---|---|---|---|
| 1.033 | [(3aR,3bS,6aR,6bS)-5-(1H-benzotriazole-5-carbonyl)-octahydro-cyclobuta[1,2-c;3,4-c']dipyrrol-2-yl]-(6-chloro-1H-indol-2-yl)-methanone | 6-chloro-1H-indole-2-carboxylic acid (CAS-RN 16732-75-5) | 1H-benzo[d][1,2,3]triazole-5-carboxylic acid | 461.6 (M + H)+ |
| 1.034 | [(3aR,3bS,6aR,6bS)-5-(1H-benzotriazole-5-carbonyl)-octahydro-cyclobuta[1,2-c;3,4-c']dipyrrol-2-yl]-(6-chloro-1-methyl-1H-indol-2-yl)-methanone | 6-chloro-1-methyl-1H-indole-2-carboxylic acid (CAS-RN 680569-83-9) | 1H-benzo[d][1,2,3]triazole-5-carboxylic acid | 475.6 (M + H)+ |
| 1.035 | [(3aR,3bS,6aR,6bS)-5-(1H-benzotriazole-5-carbonyl)-octahydro-cyclobuta[1,2-c;3,4-c']dipyrrol-2-yl]-(6-methyl-1H-indol-2-yl)-methanone | 6-methyl-1H-indole-2-carboxylic acid (CAS-RN 18474-59-4) | 1H-benzo[d][1,2,3]triazole-5-carboxylic acid | 441.7 (M + H)+ |
| 1.036 | {2-[(3aR,3bS,6aR,6bS)-5-(1H-benzotriazole-5-carbonyl)-octahydro-cyclobuta[1,2-c;3,4-c']dipyrrole-2-carbonyl]-indol-1-yl}-acetonitrile | 1-(cyanomethyl)-1H-indole-2-carboxylic acid (CAS-RN 959089-89-5) | 1H-benzo[d][1,2,3]triazole-5-carboxylic acid | 466.6 (M + H)+ |

-continued

| Ex. | Systematic Name | carboxylic acid 1 | carboxylic acid 2 | MS, m/e |
|---|---|---|---|---|
| 1.037 | [(3aR,3bS,6aR,6bS)-5-(1H-benzotriazole-5-carbonyl)-octahydro-cyclobuta[1,2-c;3,4-c']dipyrrol-2-yl]-(1-isobutyl-1H-indol-2-yl)-methanone | 1-isobutyl-1H-indole-2-carboxylic acid (CAS-RN 1020986-39-3) | 1H-benzo[d]-[1,2,3]triazole-5-carboxylic acid | 483.7 (M + H)+ |
| 1.038 | [(3aR,3bS,6aR,6bS)-5-(1H-benzotriazole-5-carbonyl)-octahydro-cyclobuta[1,2-c;3,4-c']dipyrrol-2-yl]-quinolin-2-yl-methanone | quinaldic acid (CAS-RN 93-10-7) | 1H-benzo[d]-[1,2,3]triazole-5-carboxylic acid | 439.5 (M + H)+ |
| 1.039 | [(3aR,3bS,6aR,6bS)-5-(1H-benzotriazole-5-carbonyl)-octahydro-cyclobuta[1,2-c;3,4-c']dipyrrol-2-yl]-isoquinolin-3-yl-methanone | isoquinoline-3-carboxylic acid (CAS-RN 6624-49-3) | 1H-benzo[d]-[1,2,3]triazole-5-carboxylic acid | 439.5 (M + H)+ |
| 1.040 | [(3aS,3bS,6aR,6bR)-5-(1H-benzotriazole-5-carbonyl)-octahydro-cyclobuta[1,2-c;3,4-c']dipyrrol-2-yl]-(1H-indol-6-yl)-methanone | indole-6-carboxylic acid (CAS-RN 1670-82-2) | 1H-benzo[d]-[1,2,3]triazole-5-carboxylic acid | 427.7 (M + H)+ |

-continued

| Ex. | Systematic Name | carboxylic acid 1 | carboxylic acid 2 | MS, m/e |
|---|---|---|---|---|
| 1.041 | 3-[(3aS,3bR,6aS,6bR)-5-(1H-benzotriazole-5-carbonyl)-octahydro-cyclobuta[1,2-c;3,4-c']dipyrrole-2-carbonyl]-3,4-dihydro-2H-naphthalen-1-one | 4-oxo-1,2,3,4-tetrahydro-naphthalene-2-carboxylic acid (CAS-RN 6566-40-1) | 1H-benzo[d]-[1,2,3]triazole-5-carboxylic acid | 456.5 (M + H)+ |
| 1.042 | [(3aR,3bS,6aR,6bS)-5-(1H-benzotriazole-5-carbonyl)-octahydro-cyclobuta[1,2-c;3,4-c']dipyrrol-2-yl]-chroman-2-yl-methanone | chroman-2-carboxylic acid (CAS-RN 51939-71-0) | 1H-benzo[d]-[1,2,3]triazole-5-carboxylic acid | 444.7 (M + H)+ |
| 1.043 | [(3aS,3bS,6aR,6bR)-5-(1H-benzotriazole-5-carbonyl)-octahydro-cyclobuta[1,2-c;3,4-c']dipyrrol-2-yl]-(1H-indol-5-yl)-methanone | indole-5-carboxylic acid (CAS-RN 1670-81-1) | 1H-benzo[d]-[1,2,3]triazole-5-carboxylic acid | 427.6 (M + H)+ |
| 1.044 | (4-methoxy-naphthalen-2-yl)-[(3aR,3bS,6aR,6bS)-5-((R)-4,5,6,7-tetrahydro-1H-benzotriazole-5-carbonyl)-octahydro-cyclobuta[1,2-c;3,4-c']dipyrrol-2-yl]-methanone | 4-methoxy-2-naphthoic acid (CAS-RN 5773-93-3) | (+)-(R)-4,5,6,7-tetrahydro-1H-benzo[d][1,2,3]triazole-5-carboxylic acid (intermediate 11) | 472.7 (M + H)+ |

-continued

| Ex. | Systematic Name | carboxylic acid 1 | carboxylic acid 2 | MS, m/e |
|---|---|---|---|---|
| 1.045 | [(3aS,3bS,6aR,6bR)-5-(1H-benzotriazole-5-carbonyl)-octahydro-cyclobuta[1,2-c;3,4-c']dipyrrol-2-yl]-[6-(4-chloro-phenyl)-pyridin-3-yl]-methanone | 6-(4-chlorophenyl)-nicotinic acid (CAS-RN 31676-66-1) | 1H-benzo[d]-[1,2,3]triazole-5-carboxylic acid | 499.4 (M + H)+ |
| 1.046 | [(3aR,3bS,6aR,6bS)-5-(1H-benzotriazole-5-carbonyl)-octahydro-cyclobuta[1,2-c;3,4-c']dipyrrol-2-yl]-(1-methoxy-isoquinolin-3-yl)-methanone | 1-methoxyiso-quinoline-3-carboxylic acid (CAS-RN 1094553-95-3) | 1H-benzo[d]-[1,2,3]triazole-5-carboxylic acid | 469.6 (M + H)+ |
| 1.047 | [(3aR,3bS,6aR,6bS)-5-(1H-benzotriazole-5-carbonyl)-octahydro-cyclobuta[1,2-c;3,4-c']dipyrrol-2-yl]-(4-methyl-quinolin-2-yl)-methanone | 4-methylquinoline-2-carboxylic acid (CAS-RN 40609-76-5) | 1H-benzo[d]-[1,2,3]triazole-5-carboxylic acid | 453.5 (M + H)+ |
| 1.048 | [(3aR,3bS,6aR,6bS)-5-(1H-benzotriazole-5-carbonyl)-octahydro-cyclobuta[1,2-c;3,4-c']dipyrrol-2-yl]-(5-chloro-1H-indol-2-yl)-methanone | 5-chloroindole-2-carboxylic acid (CAS-RN 10517-21-2) | 1H-benzo[d]-[1,2,3]triazole-5-carboxylic acid | 461.4 (M + H)+ |

-continued

| Ex. | Systematic Name | carboxylic acid 1 | carboxylic acid 2 | MS, m/e |
|---|---|---|---|---|
| 1.049 | [(3aS,3bS,6aR,6bR)-5-(1H-benzotriazole-5-carbonyl)-octahydro-cyclobuta[1,2-c;3,4-c']dipyrrol-2-yl]-[4-(2-methoxy-ethoxy)-naphthalen-2-yl]-methanone | 4-(2-methoxyethoxy)-2-naphthoic acid | 1H-benzo[d]-[1,2,3]triazole-5-carboxylic acid | 512.4 (M + H)+ |
| 1.050 | [(3aS,3bS,6aR,6bR)-5-(1H-benzotriazole-5-carbonyl)-octahydro-cyclobuta[1,2-c;3,4-c']dipyrrol-2-yl]-(7-phenyl-naphthalen-2-yl)-methanone | 7-phenyl-naphthalene-2-carboxylic acid (CAS-RN 229006-56-8) | 1H-benzo[d]-[1,2,3]triazole-5-carboxylic acid | 514.6 (M + H)+ |
| 1.051 | [(3aS,3bS,6aR,6bR)-5-(1H-benzotriazole-5-carbonyl)-octahydro-cyclobuta[1,2-c;3,4-c']dipyrrol-2-yl]-(4-ethoxy-naphthalen-2-yl)-methanone | 4-ethoxy-naphthalene-2-carboxylic acid (CAS-RN 1368864-77-0) | 1H-benzo[d]-[1,2,3]triazole-5-carboxylic acid | 482.6 (M + H)+ |

-continued

| Ex. | Systematic Name | carboxylic acid 1 | carboxylic acid 2 | MS, m/e |
|---|---|---|---|---|
| 1.052 | [(3aS,3bS,6aR,6bR)-5-(1H-benzotriazole-5-carbonyl)-octahydro-cyclobuta[1,2-c;3,4-c']dipyrrol-2-yl]-(4-isopropoxy-naphthalen-2-yl)-methanone | 4-isopropoxy-naphthalene-2-carboxylic acid (CAS-RN 1368865-02-4) | 1H-benzo[d]-[1,2,3]triazole-5-carboxylic acid | 496.5 (M + H)+ |
| 1.053 | [(3aS,3bS,6aR,6bR)-5-(1H-benzotriazole-5-carbonyl)-octahydro-cyclobuta[1,2-c;3,4-c']dipyrrol-2-yl]-(4-benzyloxy-1H-indol-6-yl)-methanone | 4-benzyloxy-1H-indole-6-carboxylic acid (CAS-RN 105265-24-5) | 1H-benzo[d]-[1,2,3]triazole-5-carboxylic acid | 533.4 (M + H)+ |
| 1.054 | [(3aS,3bS,6aR,6bR)-5-(1H-benzotriazole-5-carbonyl)-octahydro-cyclobuta[1,2-c;3,4-c']dipyrrol-2-yl]-(5,6,7,8-tetrahydro-naphthalen-2-yl)-methanone | 5,6,7,8-tetrahydro-2-naphthoic acid (CAS-RN 1131-63-1) | 1H-benzo[d]-[1,2,3]triazole-5-carboxylic acid | 442.5 (M + H)+ |

| Ex. | Systematic Name | carboxylic acid 1 | carboxylic acid 2 | MS, m/e |
|---|---|---|---|---|
| 1.055 | [(3aS,3bR,6aS,6bR)-5-(1H-benzotriazole-5-carbonyl)-octahydro-cyclobuta[1,2-c;3,4-c']dipyrrol-2-yl]-(4,4-dimethyl-1,2,3,4-tetrahydro-naphthalen-2-yl)-methanone | 4,4-dimethyl-1,2,3,4-tetrahydro-naphthalene-2-carboxylic acid (CAS-RN 23204-02-6) | 1H-benzo[d]-[1,2,3]triazole-5-carboxylic acid | 470.7 (M + H)$^+$ |
| 1.056 | [(3aS,3bR,6aS,6bR)-5-(1H-benzotriazole-5-carbonyl)-octahydro-cyclobuta[1,2-c;3,4-c']dipyrrol-2-yl]1-(3-methoxy-propyl)-1,2,3,4-tetrahydro-quinolin-3-yl]-methanone | 1-(3-methoxypropyl)-1,2,3,4-tetrahydro-quinoline-3-carboxylic acid (intermediate 6) | 1H-benzo[d]-[1,2,3]triazole-5-carboxylic acid | 515.5 (M + H)$^+$ |
| 1.057 | [(3aR,3bS,6aR,6bS)-5-(1H-benzotriazole-5-carbonyl)-octahydro-cyclobuta[1,2-c;3,4-c']dipyrrol-2-yl]-[1-(2-methoxy-ethoxy)-isoquinoline-3-yl]-methanone | 1-(2-methoxyethoxy)-isoquinolin-3-carboxylic acid (CAS-RN 1094758-42-5) | 1H-benzo[d]-[1,2,3]triazole-5-carboxylic acid | 513.5 (M + H)$^+$ |

-continued

| Ex. | Systematic Name | carboxylic acid 1 | carboxylic acid 2 | MS, m/e |
|---|---|---|---|---|
| 1.058 | [(3aR,3bS,6aR,6bS)-5-(1H-benzotriazole-5-carbonyl)-octahydro-cyclobuta[1,2-c;3,4-c']dipyrrol-2-yl]-(1-cyclopropylmethoxy-isoquinolin-3-yl)-methanone | 1-(cyclopropyl-methoxy)iso-quinoline-3-carboxylic acid (CAS-RN 1097166-34-1) | 1H-benzo[d]-[1,2,3]triazole-5-carboxylic acid | 509.5 (M + H)+ |
| 1.059 | (4-isopropoxy-naphthalen-2-yl)-[(3aR,3bS,6aR,6bS)-5-((R)-4,5,6,7-tetrahydro-1H-benzotriazole-5-carbonyl)-octahydro-cyclobuta[1,2-c;3,4-c']dipyrrol-2-yl]-methanone | 4-isopropoxy-naphthalene-2-carboxylic acid (CAS-RN 1368865-02-4) | (+)-(R)-4,5,6,7-tetrahydro-1H-benzo[d]-[1,2,3]triazole-5-carboxylic acid (intermediate 11) | 500.7 (M + H)+ |
| 1.060 | [(3aR,3bS,6aR,6bS)-5-(1H-benzotriazole-5-carbonyl)-octahydro-cyclobuta[1,2-c;3,4-c']dipyrrol-2-yl]-[1-(2,2,2-trifluoro-ethoxy)-isoquinolin-3-yl]-methanone | 1-(2,2,2-trifluoroethoxy)-isoquinoline-3-carboxylic acid (CAS-RN 1096982-79-4) | 1H-benzo[d]-[1,2,3]triazole-5-carboxylic acid | 537.6 (M + H)+ |
| 1.061 | [(3aS,3bS,6aR,6bR)-5-(1H-benzotriazole-5-carbonyl)-octahydro-cyclobuta[1,2-c;3,4-c']dipyrrol-2-yl]-(4-isopropoxy-1H-indol-6-yl)-methanone | 4-isopropoxy-1H-indole-6-carboxylic acid (intermediate 3.3) | 1H-benzo[d]-[1,2,3]triazole-5-carboxylic acid | 485.4 (M + H)+ |

-continued

| Ex. | Systematic Name | carboxylic acid 1 | carboxylic acid 2 | MS, m/e |
|---|---|---|---|---|
| 1.062 | 4-[(3aS,3bS,6aR,6bR)-5-(4-isopropoxy-naphthalene-2-carbonyl)-octahydro-cyclobuta[1,2-c;3,4-c']dipyrrole-2-carbonyl]benzenesulfonamide | 4-isopropoxy-naphthalene-2-carboxylic acid (CAS-RN 1368865-02-4) | 4-sulfamoyl-benzoic acid | 534.6 (M + H)+ |
| 1.063 | [6-(4-chloro-phenyl)-pyridin-3-yl]-[(3aR,3bS,6aR,6bS)-5-((R)-4,5,6,7-tetrahydro-1H-benzotriazole-5-carbonyl)-octahydro-cyclobuta[1,2-c;3,4-c']dipyrrol-2-yl]-methanone | 6-(4-chlorophenyl)-nicotinic acid (CAS-RN 31676-66-1) | (+)-(R)-4,5,6,7-tetrahydro-1H-benzo[d][1,2,3]triazole-5-carboxylic acid (intermediate 11) | 503.4 (M + H)+ |
| 1.064 | (1-cyclopropylmethoxy-isoquinolin-3-yl)-[(3aR,3bS,6aR,6bS)-5-((R)-4,5,6,7-tetrahydro-1H-benzotriazole-5-carbonyl)-octahydro-cyclobuta[1,2-c;3,4-c']dipyrrol-2-yl]-methanone | 1-(cyclopropyl-methoxy)iso-quinoline-3-carboxylic acid (CAS-RN 1097166-34-1) | (+)-(R)-4,5,6,7-tetrahydro-1H-benzo[d][1,2,3]triazole-5-carboxylic acid (intermediate 11) | 513.7 (M + H)+ |

-continued

| Ex. | Systematic Name | carboxylic acid 1 | carboxylic acid 2 | MS, m/e |
|---|---|---|---|---|
| 1.065 | [(3aS,3bS,6aR,6bR)-5-(1H-benzotriazole-5-carbonyl)-octahydro-cyclobuta[1,2-c;3,4-c']dipyrrol-2-yl]-(4-isopropoxy-1-methyl-1H-indol-6-yl)-methanone | 4-isopropoxy-1-methyl-1H-indole-6-carboxylic acid (intermediate 10) | 1H-benzo[d]-[1,2,3]triazole-5-carboxylic acid | 499.7 (M + H)+ |
| 1.066 | [(3aR,3bS,6aR,6bS)-5-(1H-benzotriazole-5-carbonyl)-octahydro-cyclobuta[1,2-c;3,4-c']dipyrrol-2-yl]-(4-ethoxy-quinolin-2-yl)-methanone | 4-ethoxyquinoline-2-carboxylic acid (CAS-RN 40609-78-7) | 1H-benzo[d]-[1,2,3]triazole-5-carboxylic acid | 483.6 (M + H)+ |
| 1.067 | [(3aR,3bS,6aR,6bS)-5-(1H-benzotriazole-5-carbonyl)-octahydro-cyclobuta[1,2-c;3,4-c']dipyrrol-2-yl]-(4-isopropoxy-quinolin-2-yl)-methanone | 4-isopropoxy-quinoline-2-carboxylic acid (CAS-RN 1406553-19-2) | 1H-benzo[d]-[1,2,3]triazole-5-carboxylic acid | 497.4 (M + H)+ |

-continued

| Ex. | Systematic Name | carboxylic acid 1 | carboxylic acid 2 | MS, m/e |
|---|---|---|---|---|
| 1.068 | [(3aS,3bS,6aR,6bR)-5-(1H-benzotriazole-5-carbonyl)-octahydro-cyclobuta[1,2-c;3,4-c']dipyrrol-2-yl]-(6-chloro-9H-carbazol-2-yl)-methanone | 6-chloro-9H-carbazole-2-carboxylic acid (CAS-RN 58479-49-5) | 1H-benzo[d]-[1,2,3]triazole-5-carboxylic acid | 511.6 (M + H)+ |
| 1.069 | [(3aR,3bS,6aR,6bS)-5-(1H-benzotriazole-5-carbonyl)-octahydro-cyclobuta[1,2-c;3,4-c']dipyrrol-2-yl]-[4-(2-methoxy-ethoxy)-quinolin-2-yl]-methanone | 4-(2-methoxy-ethoxy)quinoline-2-carboxylic acid (CAS-RN 52144-36-2) | 1H-benzo[d]-[1,2,3]triazole-5-carboxylic acid | 513.4 (M + H)+ |
| 1.070 | [(3aR,3bS,6aR,6bS)-5-(1H-benzotriazole-5-carbonyl)-octahydro-cyclobuta[1,2-c;3,4-c']dipyrrol-2-yl]-(4-isopropoxy-7-trifluoromethyl-quinolin-2-yl)-methanone | 4-isopropoxy-7-(trifluoromethyl)quinoline-2-carboxylic acid (intermediate 2) | 1H-benzo[d]-[1,2,3]triazole-5-carboxylic acid | 565.4 (M + H)+ |

-continued

| Ex. | Systematic Name | carboxylic acid 1 | carboxylic acid 2 | MS, m/e |
|---|---|---|---|---|
| 1.071 | [(3aR,3bS,6aR,6bS)-5-(1H-benzotriazole-5-carbonyl)-octahydro-cyclobuta[1,2-c;3,4-c′]dipyrrol-2-yl]-(4-cyclopropylmethoxy-quinolin-2-yl)-methanone | 4-(cyclopropyl-methoxy)-quinoline-2-carboxylic acid (CAS-RN 1275281-11-2) | 1H-benzo[d]-[1,2,3]triazole-5-carboxylic acid | 509.6 (M + H)+ |
| 1.072 | [(3aR,3bS,6aR,6bS)-5-(1H-benzotriazole-5-carbonyl)-octahydro-cyclobuta[1,2-c;3,4-c′]dipyrrol-2-yl]-[5-(4-chloro-phenyl)-pyridin-2-yl]-methanone | 5-(4-chlorophenyl)-picolinic acid (CAS-RN 87789-85-3) | 1H-benzo[d]-[1,2,3]triazole-5-carboxylic acid | 499.4 (M + H)+ |
| 1.073 | [(3aR,3bS,6aR,6bS)-5-(1H-benzotriazole-5-carbonyl)-octahydro-cyclobuta[1,2-c;3,4-c′]dipyrrol-2-yl]-(1-ethoxy-isoquinolin-3-yl)-methanone | 1-ethoxyiso-quinoline-3-carboxylic acid (CAS-RN 1094758-39-0) | 1H-benzo[d]-[1,2,3]triazole-5-carboxylic acid | 483.4 (M + H)+ |

-continued

| Ex. | Systematic Name | carboxylic acid 1 | carboxylic acid 2 | MS, m/e |
|---|---|---|---|---|
| 1.074 | [(3aS,3bS,6aR,6bR)-5-(1H-benzotriazole-5-carbonyl)-octahydro-cyclobuta[1,2-c;3,4-c']dipyrrol-2-yl]-(1-ethyl-4-isopropoxy-1H-indol-6-yl)-methanone | 1-ethyl-4-isopropoxy-1H-indole-6-carboxylic acid (intermediate 2.6) | 1H-benzo[d]-[1,2,3]triazole-5-carboxylic acid | 513.7 (M + H)+ |
| 1.075 | 6-[(3aR,3bS,6aR,6bS)-5-(1H-benzotriazole-5-carbonyl)-octahydro-cyclobuta[1,2-c;3,4-c']dipyrrole-2-carbonyl]-3-(4-chloro-phenyl)-1H-pyridin-2-one | 5-(4-chlorophenyl)-6-oxo-1,6-dihydropyridine-2-carboxylic acid (intermediate 3.2) | 1H-benzo[d]-[1,2,3]triazole-5-carboxylic acid | 515.6 (M + H)+ |
| 1.076 | [(3aR,3bS,6aR,6bS)-5-(1H-benzotriazole-5-carbonyl)-octahydro-cyclobuta[1,2-c;3,4-c']dipyrrol-2-yl]-(7-chloro-4-ethoxy-quinolin-2-yl)-methanone | 7-chloro-4-ethoxyquinoline-2-carboxylic acid (intermediate 2.5) | 1H-benzo[d]-[1,2,3]triazole-5-carboxylic acid | 517.4 (M + H)+ |

-continued

| Ex. | Systematic Name | carboxylic acid 1 | carboxylic acid 2 | MS, m/e |
|---|---|---|---|---|
| 1.077 | (7-chloro-4-ethoxy-quinolin-2-yl)-[(3aR,3bS,6aR,6bS)-5-((R)-4,5,6,7-tetrahydro-1H-benzotriazole-5-carbonyl)-octahydro-cyclobuta[1,2-c;3,4-c']dipyrrol-2-yl]methanone | 7-chloro-4-ethoxyquinoline-2-carboxylic acid (intermediate 2.5) | (+)-(R)-4,5,6,7-tetrahydro-1H-benzo[d][1,2,3]triazole-5-carboxylic acid (intermediate 11) | 521.4 (M + H)+ |
| 1.078 | [(3aS,3bS,6aR,6bR)-5-(1H-benzotriazole-5-carbonyl)-octahydro-cyclobuta[1,2-c;3,4-c']dipyrrol-2-yl]-(4-isopropoxy-5,6,7,8-tetrahydro-naphthalen-2-yl)-methanone | 5,6,7,8-tetrahydro-2-naphthoic acid (intermediate 2.4) | 1H-benzo[d][1,2,3]triazole-5-carboxylic acid | 500.7 (M + H)+ |
| 1.079 | (1H-benzotriazol-5-yl)-{(3aS,3bR,6aS,6bR)-5-[4-(2-methoxy-ethoxy)-7-trifluoromethyl-quinoline-2-carbonyl]-octahydro-cyclobuta[1,2-c;3,4-c']dipyrrol-2-yl}-methanone | 4-(2-methoxyethoxy)-7-(trifluoromethyl)quinoline-2-carboxylic acid (intermediate 2.3) | 1H-benzo[d][1,2,3]triazole-5-carboxylic acid | 581.7 (M + H)+ |

-continued

| Ex. | Systematic Name | carboxylic acid 1 | carboxylic acid 2 | MS, m/e |
|---|---|---|---|---|
| 1.080 | (1H-benzotriazol-5-yl)-[(3aS,3bR,6aS,6bR)-5-(4-ethoxy-6-trifluoromethyl-quinoline-2-carbonyl)-octahydro-cyclobuta[1,2-c;3,4-c']dipyrrol-2-yl]-methanone | 4-ethoxy-6-(trifluoromethyl)-quinoline-2-carboxylic acid (intermediate 2.2) | 1H-benzo[d]-[1,2,3]triazole-5-carboxylic acid | 551.6 (M + H)⁺ |
| 1.081 | [(3aS,3bS,6aR,6bR)-5-(1H-benzotriazole-5-carbonyl)-octahydro-cyclobuta[1,2-c;3,4-c']dipyrrol-2-yl]-(4-ethoxy-1-ethyl-1H-indol-5-yl)-methanone | 4-ethoxy-1-ethyl-1H-indole-6-carboxylic acid (intermediate 3.1) | 1H-benzo[d]-[1,2,3]triazole-5-carboxylic acid | 499.5 (M + H)⁺ |
| 1.082 | [(3aS,3bS,6aR,6bR)-5-(1H-benzotriazole-5-carbonyl)-octahydro-cyclobuta[1,2-c;3,4-c']dipyrrol-2-yl]-[1-ethyl-4-(2,2,2-trifluoro-ethoxy)-1H-indol-5-yl]-methanone | 1-ethyl-4-(2,2,2-trifluoroethoxy)-1H-indole-6-carboxylic acid (intermediate 2.1) | 1H-benzo[d]-[1,2,3]triazole-5-carboxylic acid | 553.4 (M + H)⁺ |
| 1.083 | 5-[(3aS,3bR,6aS,6bR)-5-(4-ethoxy-quinoline-2-carbonyl)-octahydro-cyclobuta[1,2-c;3,4-c']dipyrrole-2-carbonyl]-pyridine-2-sulfonic acid amide | 4-ethoxyquinoline-2-carboxylic acid (CAS-RN 40609-78-7) | 6-sulfamoyl-nicotinic acid (CAS-RN 285135-56-0) | 522.4 (M + H)⁺ |

-continued

| Ex. | Systematic Name | carboxylic acid 1 | carboxylic acid 2 | MS, m/e |
|---|---|---|---|---|
| 1.084 | (1H-benzotriazol-5-yl)-{(3aS,3bR,6aS,6bR)-5-[4-(2,2,2-trifluoro-ethoxy)-quinoline-2-carbonyl]-octahydro-cyclobuta[1,2-c;3,4-c']dipyrrol-2-yl}-methanone | 4-(2,2,2-trifluoroethoxy)-quinoline-2-carboxylic acid (CAS-RN 1281584-65-3) | 1H-benzo[d]-[1,2,3]triazole-5-carboxylic acid | 537.4 (M + H)+ |
| 1.085 | (1H-benzotriazol-5-yl)-{(3aS,3bS,6aR,6bR)-5-[4-ethoxy-1-(2,2,2-trifluoro-ethyl)-1H-indole-6-carbonyl]-octahydro-cyclobuta[1,2-c;3,4-c']dipyrrol-2-yl}-methanone | 4-ethoxy-1-(2,2,2-trifluoroethyl)-1H-indole-6-carboxylic acid (intermediate 2.9) | 1H-benzo[d]-[1,2,3]triazole-5-carboxylic acid | 553.4 (M + H)+ |
| 1.086 | (1H-benzotriazol-5-yl)-[(3aS,3bR,6aS,6bR)-5-(5-chloro-4-cyclopropylmethoxy-pyridine-2-carbonyl)-octahydro-cyclobuta[1,2-c;3,4-c']dipyrrol-2-yl]-methanone | 5-chloro-4-(cyclopropyl-methoxy)picolinic acid | 1H-benzo[d]-[1,2,3]triazole-5-carboxylic acid | 493.4 (M + H)+ |

| Ex. | Systematic Name | carboxylic acid 1 | carboxylic acid 2 | MS, m/e |
|---|---|---|---|---|
| 1.087 | (1H-benzotriazol-5-yl)-[(3aS,3bR,6aS,6bR)-5-(5-cyclopropyl-6-cyclopropylmethoxy-pyridine-2-carbonyl)-octahydro-cyclobuta[1,2-c;3,4-c']dipyrrol-2-yl]-methanone | 5-cyclopropyl-6-(cyclopropyl-methoxy)picolinic acid (CAS-RN 1415898-71-3) | 1H-benzo[d]-[1,2,3]triazole-5-carboxylic acid | 499.4 (M + H)+ |
| 1.088 | (3,4-dimethyl-phenyl)-[(3aS,3bR,6aS,6bR)-5-(4-ethoxy-5,6,7,8-tetrahydro-quinoline-2-carbonyl)-octahydro-cyclobuta[1,2-c;3,4-c']dipyrrol-2-yl]-methanone | 4-ethoxy-5,6,7,8-tetrahydro-quinoline-2-carboxylic acid (intermediate 8) | 1H-benzo[d]-[1,2,3]triazole-5-carboxylic acid | 487.7 (M + H)+ |
| 1.089 | (1H-benzotriazol-5-yl)-[(3aS,3bS,6aR,6bR)-5-(4'-chloro-biphenyl-3-carbonyl)-octahydro-cyclobuta[1,2-c;3,4-c']dipyrrol-2-yl]-methanone | 4'-chlorobiphenyl-3-carboxylic acid (CAS-RN 4655-10-1) | 1H-benzo[d]-[1,2,3]triazole-5-carboxylic acid | 498.6 (M + H)+ |
| 1.090 | (1H-benzotriazol-5-yl)-[(3aS,3bR,6aS,6bR)-5-(4-ethoxy-7-methoxy-quinoline-2-carbonyl)-octahydro-cyclobuta[1,2-c;3,4-c']dipyrrol-2-yl]-methanone | 4-ethoxy-7-methoxy-quinoline-2-carboxylic acid (intermediate 2.8) | 1H-benzo[d]-[1,2,3]triazole-5-carboxylic acid | 513.4 (M + H)+ |

-continued

| Ex. | Systematic Name | carboxylic acid 1 | carboxylic acid 2 | MS, m/e |
| --- | --- | --- | --- | --- |
| 1.091 | [(3aS,3bS,6aR,6bR)-5-(4-ethoxy-6-trifluoromethyl-quinoline-2-carbonyl)-octahydro-cyclobuta[1,2-c;3,4-c']dipyrrol-2-yl]-(1H-[1,2,3]triazolo[4,5-b]pyridin-5-yl)-methanone | 4-ethoxy-6-(trifluoromethyl)-quinoline-2-carboxylic acid (intermediate 2.2) | 1H-[1,2,3]tri-azolo[4,5-b]pyridine-5-carboxylic acid (CAS-RN 1216149-55-1) | 552.4 (M + H)+ |
| 1.092 | [(3aS,3bS,6aR,6bR)-5-(1-ethoxy-isoquinoline-3-carbonyl)-octahydro-cyclobuta[1,2-c;3,4-c']dipyrrol-2-yl]-(1H-[1,2,3]triazolo[4,5-b]pyridin-5-yl)-methanone | 1-ethoxyiso-quinoline-3-carboxylic acid (CAS-RN 1094758-39-0) | 1H-[1,2,3]tri-azolo[4,5-b]pyridine-5-carboxylic acid CAS RN 1216149-55-1) | 484.6 (M + H)+ |
| 1.093 | (1H-benzotriazol-5-yl)-[(3aS,3bR,6aS,6bR)-5-(6-cyclopropylmethoxy-5-trifluoromethyl-pyridine-2-carbonyl)-octahydro-cyclobuta[1,2-c;3,4-c']dipyrrol-2-yl]-methanone | 6-(cyclopropyl-methoxy)-5-(trifluoromethyl)-picolinic acid (CAS-RN 1415899-19-2) | 1H-benzo[d]-[1,2,3]triazole-5-carboxylic acid | 527.4 (M + H)+ |

| Ex. | Systematic Name | carboxylic acid 1 | carboxylic acid 2 | MS, m/e |
|---|---|---|---|---|
| 1.094 | (1H-benzotriazol-5-yl)-{(3aS,3bR,6aS,6bR)-5-[5-cyclopropyl-4-(2,2,2-trifluoro-ethoxy)-pyridine-2-carbonyl]-octahydro-cyclobuta[1,2-c;3,4-c']dipyrrol-2-yl}-methanone | 5-cyclopropyl-4-(2,2,2-trifluoroethoxy)-picolinic acid | 1H-benzo[d]-[1,2,3]triazole-5-carboxylic acid | 527.4 (M + H)⁺ |
| 1.095 | (1H-benzotriazol-5-yl)-{(3aS,3bR,6a[6-cyclopropyl-5-(2,2,2-trifluoro-ethoxy)-pyridazine-3-carbonyl]-octahydro-cyclobuta[1,2-c;3,4-c']dipyrrol-2-yl}-methanone']dipyrrol-2-yl}-methanone | 6-cyclopropyl-5-(2,2,2-trifluoroethoxy)-pyridazine-3-carboxylic acid | 1H-benzo[d]-[1,2,3]triazole-5-carboxylic acid | 528.4 (M + H)⁺ |
| 1.096 | [(3aR,3bS,6aR,6bS)-5-(1H-benzotriazole-5-carbonyl)-octahydro-cyclobuta[1,2-c;3,4-c']dipyrrol-2-yl]-(6-chloro-4-ethoxy-quinolin-2-yl)-methanone | 6-chloro-4-ethoxyquinoline-2-carboxylic acid (CAS-RN 1355234-15-9) | 1H-benzo[d]-[1,2,3]triazole-5-carboxylic acid | 517.4 (M + H)⁺ |

-continued

| Ex. | Systematic Name | carboxylic acid 1 | carboxylic acid 2 | MS, m/e |
|---|---|---|---|---|
| 1.097 | (1H-benzotriazol-5-yl)-{(3aS,3bR,6aS,6bR)-5-[6-(2,2,2-trifluoro-ethoxy)-5-trifluoromethyl-pyridine-2-carbonyl]-octahydro-cyclobuta[1,2-c;3,4-c']dipyrrol-2-yl}-methanone | 6-(2,2,2-trifluoroethoxy)-5-(trifluoromethyl)-picolinic acid | 1H-benzo[d]-[1,2,3]triazole-5-carboxylic acid | 555.4 (M + H)+ |
| 1.098 | (1H-benzotriazol-5-yl)-{(3aS,3bR,6aS,6bR)-5-[6-(2,2,2-trifluoro-ethoxy)-pyridine-2-carbonyl]-octahydro-cyclobuta[1,2-c;3,4-c']dipyrrol-2-yl}-methanone | 6-(2,2,2-trifluoroethoxy)-picolinic acid (CAS-RN 1247503-48-5) | 1H-benzo[d]-[1,2,3]triazole-5-carboxylic acid | 487.7 (M + H)+ |
| 1.099 | (1H-benzotriazol-5-yl)-{(3aS,3bS,6aR,6bR)-5-[6-(2,2,2-trifluoro-ethoxy)-pyridine-3-carbonyl]-octahydro-cyclobuta[1,2-c;3,4-c']dipyrrol-2-yl}-methanone | 6-(2,2,2-trifluoroethoxy)-nicotinic acid (CAS-RN 175204-90-7) | 1H-benzo[d]-[1,2,3]triazole-5-carboxylic acid | 487.7 (M + H)+ |
| 1.100 | (1H-benzotriazol-5-yl)-{(3aS,3bS,6aR,6bR)-5-[5-bromo-6-(2,2,2-trifluoro-ethoxy)-pyridine-3-carbonyl]-octahydro-cyclobuta[1,2-c;3,4-c']dipyrrol-2-yl}-methanone | 5-bromo-6-(2,2,2-trifluoroethoxy)-nicotinic acid (CAS-RN 1211586-75-2) | 1H-benzo[d]-[1,2,3]triazole-5-carboxylic acid | 565.5 (M + H)+ |

-continued

| Ex. | Systematic Name | carboxylic acid 1 | carboxylic acid 2 | MS, m/e |
|---|---|---|---|---|
| 1.101 | (1H-benzotriazol-5-yl)-{(3aS,3bR,6aS,6bR)-5-[5-(2,2,2-trifluoro-ethoxy)-pyridine-2-carbonyl]-octahydro-cyclobuta[1,2-c;3,4-c']dipyrrol-2-yl}-methanone | 5-(2,2,2-trifluoroethoxy)-picolinic acid (CAS-RN 881409-53-6) | 1H-benzo[d]-[1,2,3]triazole-5-carboxylic acid | 487.4 (M + H)+ |
| 1.102 | [(3aS,3bR,6aS,6bR)-5-(6-cyclopropylmethoxy-pyridazine-3-carbonyl)-octahydro-cyclobuta[1,2-c;3,4-c']dipyrrol-2-yl]-(3,4-dimethyl-phenyl)-methanone | 6-(cyclopropyl-methoxy)-pyridazine-3-carboxylic acid (CAS-RN 1184404-57-6) | 1H-benzo[d]-[1,2,3]triazole-5-carboxylic acid | 460.7 (M + H)+ |
| 1.103 | (1H-benzotriazol-yl)-{(3aS,3bS,6aR,6bR)-5-[5-bromo-2-methyl-6-(2,2,2-trifluoro-ethoxy)-pyridine-3-carbonyl]-octahydro-cyclobuta[1,2-c;3,4-c']dipyrrol-2-yl}-methanone | 5-bromo-2-methyl-6-(2,2,2-trifluoroethoxy)-nicotinic acid | 1H-benzo[d]-[1,2,3]triazole-5-carboxylic acid | 577.7 (M − H)− |
| 1.104 | (1H-benzotriazol-5-yl)-{(3aS,3bS,6aR,6bR)-5-[5-cyclopropyl-6-(2,2,2-trifluoro-ethoxy)-pyridine-3-carbonyl]-octahydro-cyclobuta[1,2-c;3,4-c']dipyrrol-2-yl}-methanone | 5-cyclopropyl-6-(2,2,2-trifluoroethoxy)-nicotinic acid (CAS-RN 1427064-90-1) | 1H-benzo[d]-[1,2,3]triazole-5-carboxylic acid | 527.7 (M + H)+ |

-continued

| Ex. | Systematic Name | carboxylic acid 1 | carboxylic acid 2 | MS, m/e |
|---|---|---|---|---|
| 1.105 | (1H-benzotriazol-5-yl)-{(3aS,3bS,6aR,6bR)-5-[6-(2,2,2-trifluoro-ethoxy)-5-trifluoromethyl-pyridine-3-carbonyl]-octahydro-cyclobuta[1,2-c;3,4-c']dipyrrol-2-yl}-methanone | 6-(2,2,2-trifluoroethoxy)-5-(trifluoro-methyl)nicotinic acid | 1H-benzo[d]-[1,2,3]triazole-5-carboxylic acid | 555.6 (M + H)+ |
| 1.106 | (1H-benzotriazol-5-yl)-{(3aS,3bS,6aR,6bR)-5-[5-(tetrahydro-pyran-4-yl)-6-(2,2,2-trifluoro-ethoxy)-pyridine-3-carbonyl]-octahydro-cyclobuta[1,2-c;3,4-c']dipyrrol-2-yl}-methanone | 5-(tetrahydro-2H-pyran-4-yl)-6-(2,2,2-trifluoro-ethoxy)nicotinic acid (CAS-RN 1427064-92-3) | 1H-benzo[d]-[1,2,3]triazole-5-carboxylic acid | 571.7 (M + H)+ |
| 1.107 | (1H-benzotriazol-5-yl)-{(3aS,3bR,6aS,6bR)-5-[4-(4-chloro-phenyl)-5-(2,2,2-trifluoro-ethoxy)-pyridine-2-carbonyl]-octahydro-cyclobuta[1,2-c;3,4-c']dipyrrol-2-yl}-methanone | 4-(4-chlorophenyl)-5-(2,2,2-trifluoro-ethoxy)picolinic acid (CAS-RN 1364677-00-8) | 1H-benzo[d]-[1,2,3]triazole-5-carboxylic acid | 597.2 (M + H)+ |

-continued

| Ex. | Systematic Name | carboxylic acid 1 | carboxylic acid 2 | MS, m/e |
|---|---|---|---|---|
| 1.108 | (1H-benzotriazol-5-yl)-{(3aS,3bS,6aR,6bR)-5-[5-furan-2-yl-6-(2,2,2-trifluoro-ethoxy)-pyridine-3-carbonyl]-octahydro-cyclobuta[1,2-c;3,4-c']dipyrrol-2-yl}-methanone | 5-(furan-2-yl)-6-(2,2,2-trifluoro-ethoxy)nicotinic acid | 1H-benzo[d]-[1,2,3]triazole-5-carboxylic acid | 553.2 (M + H)⁺ |
| 1.109 | (1H-benzotriazol-5-yl)-{(3aS,3bS,6aR,6bR)-5-[5-chloro-6-(2,2,2-trifluoro-ethoxy)-pyridine-3-carbonyl]-octahydro-cyclobuta[1,2-c;3,4-c']dipyrrol-2-yl}-methanone | 5-chloro-6-oxo-1-(2,2,2-trifluoroethyl)-1,6-dihydro-pyridine-3-carboxylic acid (intermediate 3) | 1H-benzo[d]-[1,2,3]triazole-5-carboxylic acid | 521.1 (M + H)⁺ |
| 1.110 | [(3aS,3bR,6aS,6bR)-5-(4-ethoxy-quinoline-2-carbonyl)-octahydro-cyclobuta[1,2-c;3,4-c']dipyrrol-2-yl]-(4-fluoro-1H-benzotriazol-5-yl)-methanone | 4-ethoxyquinoline-2-carboxylic acid (CAS-RN 40609-78-7) | 4-fluoro-1H-benzo[d]-[1,2,3]triazole-5-carboxylic acid (intermediate 10) | 501.2 (M + H)⁺ |
| 1.111 | {(3aS,3bS,6aR,6bR)-5-[5-methanesulfonyl-6-(2,2,2-trifluoro-ethoxy)-pyridine-3-carbonyl]-octahydro-cyclobuta[1,2-c;3,4-c']dipyrrol-2-yl}-phenyl-methanone | 5-(methylsulfonyl)-6-(2,2,2-trifluoro-ethoxy)nicotinic acid (intermediate 5) | 1H-benzo[d]-[1,2,3]triazole-5-carboxylic acid | 565.2 (M + H)⁺ |

Example 2

(3aR,3bS,6aR,6bS)-5-(1H-Benzotriazole-5-carbonyl)-octahydro-cyclobuta[1,2-c;3,4-c']dipyrrole-2-carboxylic acid 4-trifluoromethoxy-benzyl Ester

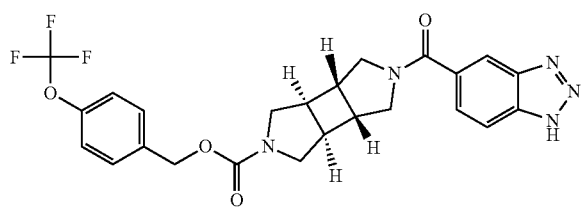 [SMILES: O=C(OCc1ccc(OC(F)(F)F)cc1)N1C[C@@H]2[C@H](C1)[C@H]1CN(C(=O)c3ccc4[nH]nnc4c3)C[C@@H]21]

To a solution of (3aS,3bS,6aR,6bR)-decahydro-cyclobuta[1,2-c;3,4-c']dipyrrole (intermediate 1; 40 mg. 289 μmol) in N,N-dimethylformamide (2 mL) were added N-methylmorpholine (146 mg, 1.45 mmol), 1H-benzo[d][1,2,3]triazole-5-carboxylic acid (47.2 mg, 289 μmol) and O-(7-azabenzotriazol-1-yl)-N,N,N',N'-tetramethyluronium hexafluorophosphate (110 mg, 289 μmol). In the meantime a second solution with (4-(trifluoromethoxy)phenyl)methanol (CAS-RN 1736-74-9; 55.6 mg, 289 μmol,) and 1,1'-carbonyldiimidazole (49.3 mg, 304 μmol) in DMF (2 ml) was prepared. The two reaction mixtures were stirred at room temperature for 4 h, then combined and stirred for another 16 h, then partitioned between sat. aq. ammonium chloride solution and ethyl acetate. The organic layer was washed with brine, dried over magnesium sulfate, filtered and evaporated. Chromatography (silica gel; gradient dichloromethane to dichloromethane/methanol/25% aq. ammonia solution 90:10:0.25) produced the title compound (38 mg, 26%). White solid, MS: 502.3 (M+H)+.

Example 2.001

(3aR,3bS,6aR,6bS)-5-(1H-Benzotriazole-5-carbonyl)-octahydro-cyclobuta[1,2-c;3,4-c']dipyrrole-2-carboxylic Acid 3,5-dichloro-benzyl Ester

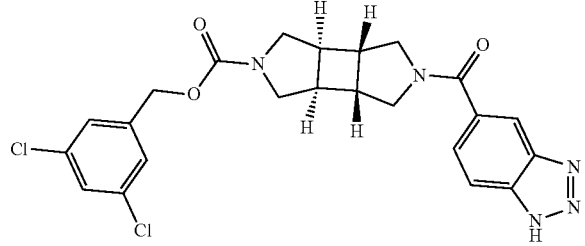 [SMILES: O=C(OCc1cc(Cl)cc(Cl)c1)N1C[C@@H]2[C@H](C1)[C@H]1CN(C(=O)c3ccc4[nH]nnc4c3)C[C@@H]21]

The title compound was produced in analogy to example 2, replacing (4-(trifluoromethoxy)-phenyl)methanol by (3,5-dichlorophenyl)methanol (CAS-RN 60211-57-6). White solid, MS: 486.5 (M+H)+.

Example 3

(1H-Benzotriazol-5-yl)-[(3aS,3bR,6aS,6bR)-5-(4'-fluoro-biphenyl-4-sulfonyl)-octahydro-cyclobuta[1,2-c;3,4-c']dipyrrol-2-yl]-methanone

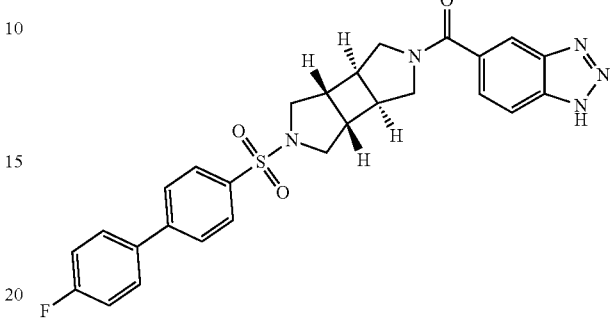

(3aS,3bR,6aS,6bR)-5-(4'-Fluoro-biphenyl-4-sulfonyl)-octahydro-cyclobuta[1,2-c;3,4-c']dipyrrole-2-carboxylic acid tert-butyl ester (intermediate 12; 26 mg, 55.0 μmol) was combined with hydrochloric acid solution (5-6 M in 2-propanol; 1 mL) and stirred at room temperature for 18 h. After evaporation of volatile material the residue was taken up in N,N-dimethylformamide (1 mL), then N-methylmorpholine (27.8 mg, 275 μmol), 1H-benzo[d][1,2,3]triazole-5-carboxylic acid (9.9 mg, 61 μmol) and O-(7-azabenzotriazol-1-yl)-N,N,N',N'-tetramethyluronium hexafluoro-phosphate (23 mg, 61 μmol) were added. After 16 h the reaction mixture was partitioned between water sat. aq. ammonium chloride solution and ethyl acetate. The organic layer was washed with brine, dried over magnesium sulfate, filtered, and evaporated. Chromatography (silica gel; gradient dichloromethane to dichloromethane/methanol/25% aq. ammonia solution 90:10:0.25) produced the title compound (26 mg, 82%). Light yellow gum, MS: 516.6 (M−H)−.

Example 3.001

(1H-Benzotriazol-5-yl)-[(3aS,3bR,6aS,6bR)-5-(6-chloro-naphthalene-2-sulfonyl)-octahydro-cyclobuta[1,2-c;3,4-c']dipyrrol-2-yl]-methanone

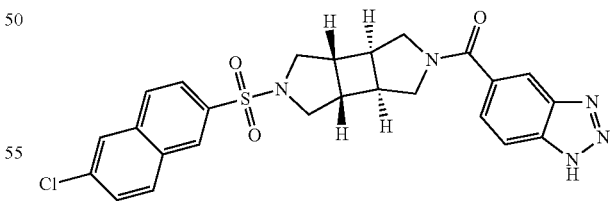

A solution of 6-chloro-naphthalene-2-sulfonyl chloride (CAS-RN 102153-63-9, 33.6 mg, 129 μmol) in dichloromethane (1 mL) was added at room temperature to a solution of (3aS,3bS,6aR,6bR)-decahydro-cyclobuta[1,2-c;3,4-c']dipyrrole (intermediate 1; 11.9 mg, 86 μmol) in dichloromethane (2 mL) and pyridine (33.9 mg, 34.7 μl, 428 μmol, Eq: 5), then after 4 h the reaction mixture was evaporated. The residue was taken up with N,N-dimethylformamide, then 1H-benzo[d]-[1,2,3]triazole-5-carboxylic acid (14.0 mg, 86 µmol) and O-(7-azabenzotriazol-1-yl)-N,N',N'-tetramethyluronium hexafluoro-phosphate (35.8 mg, 94 µmol) and 4-methylmorpholine (43.3 mg, 428 µmol) were added, then after 16 h the reaction mixture was partitioned between sat. aq. ammonium chloride solution and ethyl acetate. The organic layer was washed with brine, dried over magnesium sulfate, filtered, and evaporated. Chromatography (silica gel; dichloromethane/methanol/25% aq. ammonia solution 90:10:0.25) produced the title compound (4 mg, 9%). Colourless gum, MS: 508.6 (M+H)+.

Example 4

[(3aR,3bS,6aR,6bS)-5-(1H-Benzotriazole-5-carbonyl)-octahydro-cyclobuta[1,2-c;3,4-c']dipyrrol-2-yl]-(6-trifluoromethyl-3,4-dihydro-1H-isoquinolin-2-yl)-methanone

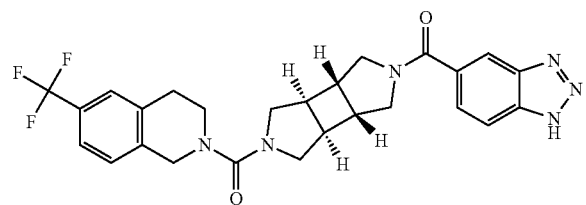 [SMILES: O=C(c1ccc2[nH]nnc2c1)N1C[C@@H]2[C@H](C1)[C@H]1CN(C(=O)N3CCc4cc(C(F)(F)F)ccc4C3)C[C@@H]21]

To a solution of (3aS,3bS,6aR,6bR)-decahydro-cyclobuta[1,2-c;3,4-c']dipyrrole (intermediate 1; 30 mg, 217 µmol) and N-methylmorpholine (108 mg, 1.07 mmol) and N,N-dimethylformamide (3 mL) was added a solution of 6-(trifluoromethyl)-3,4-dihydroisoquinoline-2(1H)-carbonyl chloride (intermediate 7; 57 mg, 214 µmol) in N,N-dimethylformamide DMF (1 ml) dropwise at room temperature, then after 1 h 1H-benzo[d][1,2,3]triazole-5-carboxylic acid (34.9 mg, 214 µmol) and O-(7-azabenzotriazol-1-yl)-N,N,N',N'-tetramethyluronium hexafluoro-phosphate (81.4 mg, 214 µmol) were added. After another 16 h the reaction mixture was partitioned between sat. aq. ammonium chloride solution and ethyl acetate. The organic layer was washed with brine, dried over magnesium sulfate, filtered, and evaporated. Chromatography (silica gel; dichloromethane/methanol/25% aq. ammonia solution 90:10:0.25) produced the title compound (24 mg, 22%). White solid, MS: 511.4 (M+H)+.

INTERMEDIATES

Intermediate 1

(3aS,3bS,6aR,6bR)-Decahydro-cyclobuta[1,2-c;3,4-c']dipyrrole

Step 1: (3aS,3bS,6aR,6bR)-2,5-Dibenzyl-tetrahydro-cyclobuta[1,2-c;3,4-c']dipyrrole-1,3,4,6-tetraone A solution of 1-benzyl-1H-pyrrole-2,5-dione (1.12 g, 5.98 mmol) in acetonitrile (60 ml) was purged with nitrogen for 10 min, then irradiated at 300 nm for 6 h to produce a white suspension. About 30 mL of acetonitrile was distilled off, then the product was collected by filtration (447 mg, 40%). Off-white solid, MS: 375.5 (M+H)+, H-NMR (300 MHz, DMSO-$d_6$): 7.35-7.25 (m, 10H), 4.63 (s, 4H), 3.45 (s, 4H).

Step 2: (3aS,3bS,6aR,6bR)-2,5-Dibenzyl-decahydro-cyclobuta[1,2-c;3,4-c']dipyrrole To a suspension of lithium aluminum hydride (3.05 g, 80.3 mmol) in diethyl ether (120 mL) was added portionwise (3aS,3bS,6aR,6bR)-2,5-dibenzyl-tetrahydro-cyclobuta[1,2-c;3,4-c']dipyrrole-1,3,4,6-tetraone (7.52 g, 20.1 mmol) over 10 min at room temperature. The reaction mixture was stirred at room temperature for 4 h, then cooled down to 0° C. and quenched by slow addition of water (40 mL) and 2 M aq. sodium hydroxide solution. Water (500 mL) and ethyl acetate (500 mL) were added, then after filtration through diatomaceous earth the organic layer was washed with brine, dried over magnesium sulfate, filtered, and evaporated. The residue was triturated in methanol (40 mL) to produce the title compound (4.60 g, 72%). White solid, MS: 319.6 (M+H)+, $^1$H-NMR (300 MHz, CDCl$_3$): 7.4-7.2 (m, 10H), 3.65 (s, 4H), 2.82 (d, J=9.3, 4H), 2.39 (d, J=4.4, 4H), 2.05 (dd, J=9.3, 4.4, 4H).

Step 3: (3aS,3bS,6aR,6bR)-Decahydro-cyclobuta[1,2-c;3,4-c']dipyrrole

A solution of (3aS,3bS,6aR,6bR)-2,5-dibenzyl-decahydro-cyclobuta[1,2-c;3,4-c']dipyrrole (4.6 g, 14.4 mmol, Eq: 1.00) was stirred for 4 h at 50° C. under a hydrogen atmosphere (3 bar) in the presence of palladium (10% on activated charcoal, 2.08 g), then insoluble material was removed by filtration through diatomaceous earth. The filtrate was evaporated to produce the title compound (1.72 g, 86%). White solid, MS: 139.2 (M+H)+, $^1$H-NMR (300 MHz, CDCl$_3$): 2.99 (d, J=11.4, 4H), 2.68 (dd, J=11.4, 4.4, 4H), 2.25-2.15 (m, 6H).

Intermediate 2

4-isopropoxy-7-(trifluoromethyl)quinoline-2-carboxylic Acid

Step 1: Methyl 4-isopropoxy-7-(trifluoromethyl)quinoline-2-carboxylate

To a stirring suspension of methyl 4-hydroxy-7-(trifluoromethyl)quinoline-2-carboxylate (300 mg, 1.08 mmol) in acetonitrile (3 mL) were added potassium carbonate (449 mg, 3.25 mmol) and 2-iodopropane (570 mg, 3.25 mmol). The reaction mixture was stirred for 16 h at 80° C., then partitioned between water and ethyl acetate. The organic layer was washed with brine, dried over magnesium sulfate, filtered, and evaporated. Chromatography (silica gel; heptane-ethyl acetate gradient) produced the title compound (334 mg, 98%) as a white solid.

Step 2: 4-Isopropoxy-7-(trifluoromethyl)quinoline-2-carboxylic Acid

A mixture of methyl 4-isopropoxy-7-(trifluoromethyl)quinoline-2-carboxylate (330 mg, 1.05 mmol), potassium hydroxide (209 mg, 3.16 mmol), ethanol (3.5 mL), and water (3.5 mL) was heated at 80° C. for 45 min, then most of the ethanol was distilled off. The remaining aqueous solution was acidified to pH 1 with 1 M hydrochloric acid solution. The precipitate was collected by filtration and dried to produce the title compound (304 mg, 96%). White solid MS: 299.9 (M+H)+.

The following intermediates were produced in analogy to intermediate 2, replacing methyl 4-hydroxy-7-(trifluoromethyl)quinoline-2-carboxylate and 2-iodopropane by the appropriate starting material and alkylating agent, respectively.

| No. | Systematic name | Starting material | alkylating agent | MS, m/e |
|---|---|---|---|---|
| 2.1 | 1-ethyl-4-(2,2,2-trifluoroethoxy)-1H-indole-6-carboxylic acid | methyl 1-ethyl-4-hydroxy-1H-indole-6-carboxylate (CAS-RN 934617-51-3) | 2,2,2-trifluoroethyl trifluoromethane-sulfonate | 288.4 |
| 2.2 | 4-ethoxy-6-(trifluoromethyl)quinoline-2-carboxylic acid | methyl 4-hydroxy-6-(trifluoromethyl)quinoline-2-carboxylate (CAS-RN 1422284-64-7) | iodoethane | 286.5 |
| 2.3 | 4-(2-methoxyethoxy)-7-(trifluoromethyl)quinoline-2-carboxylic acid | methyl 4-hydroxy-7-(trifluoromethyl)quinoline-2-carboxylate (CAS-RN 1072944-69-4) | 1-bromo-2-methoxyethane | 316.5 $(M + H)^+$ |
| 2.4 | 4-isopropoxy-5,6,7,8-tetrahydronaphthalene-2-carboxylic acid | methyl 4-hydroxy-5,6,7,8-tetrahydronaphthalene-2-carboxylate (CAS-RN 184107-09-3) | 2-iodopropane | 233.3 $(M - H)^-$ |
| 2.5 | 7-chloro-4-ethoxyquinoline-2-carboxylic acid | methyl 7-chloro-4-hydroxyquinoline-2-carboxylate | iodoethane | 252.5 $(M + H)^+$ |
| 2.6 | 1-ethyl-4-propan-2-yloxyindole-6-carboxylic acid | methyl 1-ethyl-4-hydroxy-1H-indole-6-carboxylate (CAS-RN 934617-51-3) | 2-iodopropane | 248.6 $(M + H)^+$ |
| 2.8 | 4-ethoxy-7-methoxyquinoline-2-carboxylic acid | methyl 4-hydroxy-7-methoxyquinoline-2-carboxylate (CAS-RN 259214-73-8) | iodoethane | 248.2 $(M + H)^+$ |
| 2.9 | 4-ethoxy-1-(2,2,2-trifluoroethyl)-1H-indole-6-carboxylic acid | methyl 4-ethoxy-1H-indole-6-carboxylate (CAS-RN 372099-86-0) | 2,2,2-trifluoro-ethyl trifluoro-methanesulfonate | 288.5 $(M + H)^+$ |

Intermediate 3

5-Chloro-6-oxo-1-(2,2,2-trifluoroethyl)-1,6-dihydropyridine-3-carboxylic Acid Lithium hydroxide monohydrate (102 mg, 2.4 mmol) was added to a solution of methyl 5-chloro-6-oxo-1-(2,2,2-trifluoroethyl)-1,6-dihydropyridine-3-carboxylate (328 mg, 1.22 mmol) in tetrahydrofuran (mL) and water (1 mL), then after 16 h the reaction mixture was partially evaporated in order to remove most of the tetrahydrofuran. The remaining aqueous solution was acidified to pH 1 with 1 M aq. hydrochloric acid solution. The precipitate was collected by filtration and dried to afford the title compound (289 mg, 93%). White solid, MS: 254.2 $(M–H)^-$.

The following intermediates were prepared in analogy to intermediate 3, replacing methyl 5-chloro-6-oxo-1-(2,2,2-trifluoroethyl)-1,6-dihydropyridine-3-carboxylate by the appropriate starting material.

| No. | Systematic name | Starting material | MS, m/e |
|---|---|---|---|
| 3.1 | 4-ethoxy-1-ethyl-1H-indole-6-carboxylic acid | methyl 4-ethoxy-1-ethyl-1H-indole-6-carboxylate (CAS-RN 372099-98-4) | 234.5 $(M + H)^+$ |
| 3.2 | 5-(4-chlorophenyl)-6-oxo-1,6-dihydropyridine-2-carboxylic acid | methyl 5-(4-chlorophenyl)-6-hydroxypicolinate | 248.1 $(M − H)^-$ |
| 3.3 | 4-isopropoxy-1H-indole-6-carboxylic acid | methyl 4-isopropoxy-1H-indole-6-carboxylate (intermediate 9, step 1) | 218.3 $(M − H)^-$ |

Intermediate 4

5-Cyclopropyl-4-(2,2,2-trifluoroethoxy)picolinic Acid

5-Cyclopropyl-4-(2,2,2-trifluoroethoxy)picolinonitrile (250 mg, 1.03 mmol) was combined with 25% aq. hydrochloric acid solution (5 mL) and heated at 110° C. for 3 h. After cooling the reaction mixture was evaporated to dryness. The residue was suspended in water (5 mL) basified with 6 M aq. sodium hydroxide solution, then the resulting solution was acidified to pH 1. The precipitate was collected by filtration and dried to produce the title compound (159 mg, 59%). White solid, MS: 262.2 $(M+H)^+$.

Intermediate 5

5-(Methylsulfonyl)-6-(2,2,2-trifluoroethoxy)nicotinic Acid

Step 1: Methyl 5-(methylsulfonyl)-6-(2,2,2-trifluoroethoxy)nicotinate

A mixture of L-proline (88 mg, 0.76 mmol, Eq: 0.8) and sodium hydroxide (31 mg, 0.76 mmol) and dimethyl sulfoxide (5 mL), was stirred at room temperature for 30 min, then methyl 5-bromo-6-(2,2,2-trifluoroethoxy)nicotinate (300 mg, 955 µmol), sodium methanesulfinate (804 mg, 7.64 mmol) and copper(I) iodide (146 mg, 764 µmol) were added, and the reaction mixture was heated at 80° C. for 16 h, then partitioned between 1 M aq. hydrochloric acid solution and ethyl acetate. The organic layer was washed with brine, dried over magnesium sulfate, filtered, and evaporated. The residue was purified by chromatography (silica gel; heptane-ethyl acetate gradient produced the title compound (80 mg, 27%). White solid, MS: 314 $(M+H)^+$.

Step 2: 5-(Methylsulfonyl)-6-(2,2,2-trifluoroethoxy) nicotinic Acid

The title compound was produced in analogy to intermediate 2, step 2 from methyl 5-(methylsulfonyl)-6-(2,2,2-trifluoroethoxy)nicotinate. White solid, MS: 298.1 (M−H)⁻.

Intermediate 6

1-(3-Methoxy-propyl)-1,2,3,4-tetrahydro-quinoline-3-carboxylic Acid

A mixture of methyl 1,2,3,4-tetrahydroquinoline-3-carboxylate (CAS-RN 177202-62-9; 300 mg, 1.57 mmol) 1-bromo-3-methoxypropane (735 mg, 4.71 mmol) and sodium hydrogencarbonate (659 mg, 7.84 mmol) in ethanol (3 mL) was heated at reflux. After 18 h the reaction mixture was evaporated and the residue chromatographed (silica gel; heptane-ethyl acetate gradient) to produce a mixture of 1-(3-methoxy-propyl)-1,2,3,4-tetrahydro-quinoline-3-carboxylic acid methyl ester and 1-(3-methoxy-propyl)-1,2,3,4-tetrahydro-quinoline-3-carboxylic acid ethyl ester (251 mg). This material was combined with ethanol (2.5 mL), water (2.5 mL) and potassium hydroxide (264 mg, 4.71 mmol) and heated at 80° C. for 45 min, then the reaction mixture was partially evaporated in order to remove most of the ethanol. The remaining aqueous solution was partitioned between ethyl acetate and 1 M aq. hydrochloric acid solution. The organic layer was washed with brine, dried over magnesium sulfate, filtered, and evaporated to produce the title compound (190 mg, 49%). Light yellow oil, MS: 248.5 (M−H)⁻.

Intermediate 7

6-(Trifluoromethyl)-3,4-dihydroisoquinoline-2(1H)-carbonyl Chloride

To a white suspension of 6-(trifluoromethyl)-1,2,3,4-tetrahydroisoquinoline hydrochloride (CAS-RN 215798-14-4; 500 mg, 2.04 mmol) and pyridine (339 mg, 4.29 mmol) in dichloromethane (5 mL) was added dropwise a solution of triphosgene (273 mg, 918 μmol,) in dichloromethane (5 mL) at 0° C. After 30 min the ice bath was removed, then after 16 h the reaction mixture was partitioned between 1 M aq. hydrochloric acid solution and dichloromethane. The organic layer was washed with brine, dried over magnesium sulfate, filtered, and evaporated to produce the title compound (546 mg, quant.) as a yellow oil.

Intermediate 8

4-Ethoxy-5,6,7,8-tetrahydroquinoline-2-carboxylic Acid

Step 1: Methyl 4-hydroxy-5,6,7,8-tetrahydroquinoline-2-carboxylate

A solution of methyl 4-hydroxyquinoline-2-carboxylate (CAS-RN 5965-59-3; 1.0 g, 4.92 mmol) in 37% aq. hydrochloric acid solution (36 mL) was stirred at room temperature under an atmosphere of hydrogen (4 bar) in the presence of platinum(IV) oxide (124 mg). After 72 h insoluble material was removed by filtration through diatomaceous earth, and the filtrate was evaporated to produce the title compound (1.06 g, 69%). White solid, MS: 208.3 (M+H)⁺.

Step 2: Methyl 4-ethoxy-5,6,7,8-tetrahydroquinoline-2-carboxylate

The title compound was produced in analogy to intermediate 2, step 1 from methyl 4-hydroxy-5,6,7,8-tetrahydroquinoline-2-carboxylate. White solid, MS: 236.3 (M+H)⁺.

Step 3: 4-Ethoxy-5,6,7,8-tetrahydroquinoline-2-carboxylic Acid

A mixture of methyl 4-ethoxy-5,6,7,8-tetrahydroquinoline-2-carboxylate (156 mg, 663 μmol, Eq: 1.00) in ethanol (2 mL) and water (2 mL) was heated at reflux for 2 h, then most of the ethanol was distilled off and the remaining aqueous solution was acidified to pH 1, then evaporated to dryness. The residue was suspended in dichloromethane, then insoluble material was removed by filtration. The filtrate was evaporated to produce the title compound (172 mg, quant.). White solid, MS: 222.3 (M+H)⁺.

Intermediate 9

4-Isopropoxy-1-methyl-1H-indole-6-carboxylic Acid

Step 1: Methyl 4-isopropoxy-1H-indole-6-carboxylate

Potassium carbonate (651 mg, 4.71 mmol) and 2-iodopropane (275 mg, 1.57 mmol) were added to a solution of methyl 4-hydroxy-1H-indole-6-carboxylate (CAS-RN 77140-48-8; 300 mg, 1.57 mmol) in N,N-dimethylformamide (9 mL) at 0° C. The reaction mixture was stirred for 16 h at 0° C., then partitioned between water and ethyl acetate. The organic layer was washed with brine, dried over magnesium sulfate, filtered and evaporated to give a light brown oil. Chromatography (silica gel; heptane-ethyl acetate gradient) produced the title compound (280 mg, 77%). White solid, MS: 232.2 (M−H)⁻.

Step 2: Methyl 4-isopropoxy-1-methyl-1H-indole-6-carboxylate

Potassium carbonate (296 mg, 2.14 mmol) and iodomethane (183 mg, 1.29 mmol) were added to a solution of methyl 4-isopropoxy-1H-indole-6-carboxylate (100 mg, 429 μmol) in acetone (2.5 mL). The reaction mixture was heated at reflux for 16 h, then partitioned between water and ethyl acetate. The organic layer was washed with brine, dried over magnesium sulfate, filtered and evaporated to give a light brown oil. Chromatography (silica gel; heptane-ethyl acetate gradient) produced the title compound (102 mg, 96%). Colourless oil, MS: 248.2 (M−H)⁻.

Step 3: 4-Isopropoxy-1-methyl-1H-indole-6-carboxylic Acid

The title compound was produced in analogy to intermediate 2, step 2 from methyl 4-isopropoxy-1-methyl-1H-indole-6-carboxylate. Off-white solid, MS: 232.2 (M−H)⁻.

Intermediate 10

4-Fluoro-1H-benzo[d][1,2,3]triazole-5-carboxylic Acid

Step 1: 5-Bromo-4-fluoro-1H-benzo[d][1,2,3]triazole

To a light brown suspension of 4-bromo-3-fluorobenzene-1,2-diamine (1.50 g, 7.32 mmol) in water (15 mL) and acetic acid (5 mL) was added a solution of sodium nitrite (555 mg, 8.05 mmol) in water (1.5 mL) dropwise at 0° C. After 1 h at 0° C. the reaction mixture was heated to 85° C. for 1 h. After cooling the reaction mixture was partitioned between water and ethyl acetate. The organic layer was washed with brine, dried over magnesium sulfate, filtered and evaporated to produce the title compound (1.53 g, 97%). Brown solid, MS: 214.1 (M−H)⁻.

Step 2: Methyl 4-fluoro-1H-benzo[d][1,2,3]triazole-5-carboxylate

A solution of 5-bromo-4-fluoro-1H-benzo[d][1,2,3]triazole (415 mg, 1.92 mmol), 1,1'-bis(diphenylphosphino)ferrocene-palladium(II)dichloride dichloromethane complex (63.4 mg, 76.8 µmol), and triethylamine (253 mg, 2.50 mmol) in methanol (5 mL) was stirred for 18 h under a hydrogen atmosphere (70 bar) at 110° C. After cooling the reaction mixture was evaporated and the residue was purified by chromatography (silica gel; gradient dichloromethane to dichloromethane/methanol 95:5) to produce the title compound (127 mg, 31%). Red solid, MS: 194.2 (M−H)⁻.

Step 3: 4-Fluoro-1H-benzo[d][1,2,3]triazole-5-carboxylic Acid

The title compound was produced in analogy to intermediate 3 from methyl 4-fluoro-1H-benzo[d][1,2,3]triazole-5-carboxylate. Brown solid, MS: 180.2 (M−H)⁻.

Intermediate 11

(+)-(R)-4,5,6,7-Tetrahydro-1H-benzo[d][1,2,3]triazole-5-carboxylic Acid

Racemic 4,5,6,7-tetrahydro-1H-benzo[d][1,2,3]triazole-5-carboxylic acid (CAS-RN 33062-47-4; 1.10 g, 6.58 mmol) was separated by preparative HPLC using a Chiralpak AD column as the stationary phase and heptane/ethanol 3:2 as the mobile phase. This produced the faster eluting (+)-(R)-enantiomer (452 mg, 41%), followed by the slower eluting (−)-(S)-enantiomer (381 mg, 35%). White solid, MS: 166.2 (M−H)⁻.

Intermediate 12

(3aS,3bR,6aS,6bR)-5-(4'-Fluoro-biphenyl-4-sulfonyl)-octahydro-cyclobuta[1,2-c;3,4-c']dipyrrole-2-carboxylic Acid Tert-butyl Ester A solution of 4'-fluorobiphenyl-4-sulfonyl chloride (CAS-RN 116748-66-4; 42.9 mg, 158 µmol) in dichloromethane (1 mL) was added at room temperature to a solution of (3aR,3bS,6aR,6bS)-octahydro-cyclobuta[1,2-c;3,4-c']dipyrrole-2-carboxylic acid tert-butyl ester hydrochloride (intermediate 13; 29 mg, 106 µmol) and pyridine (25.0 mg, 317 µmol) in dichloromethane (1 mL). After 2 h the reaction mixture was concentrated under vacuum, and the residue was purified by chromatography (silica gel; heptane-ethyl acetate gradient) to produce the title compound (30 mg, 60%). White solid, MS: 394.6 (M+Me₃COCO+Na)⁺.

Intermediate 13

(3aR,3bS,6aR,6bS)-Octahydro-cyclobuta[1,2-c;3,4-c']dipyrrole-2-carboxylic Acid Tert-butyl Ester Hydrochloride Step 1: (3aS,3bS,6aR,6bR)-Octahydro-cyclobuta[1,2-c;3,4-c']dipyrrole-2,5-dicarboxylic Acid Di-tert-butyl Ester To a solution of (3aS,3bS,6aR,6bR)-decahydro-cyclobuta[1,2-c;3,4-c']dipyrrole (intermediate 1; 100 mg, 724 µmol) in chloroform (3 ml) was added dropwise a solution of di-tert-butyl dicarbonate (474 mg, 2.17 mmol) in chloroform (3 ml). After 2 h the reaction mixture was evaporated and the residue was chromatographed (silica gel; heptane-ethyl acetate gradient) to produce the title compound (222 mg, 91%). White solid, MS: 338.6 (M+H)⁺.

Step 2: (3aR,3bS,6aR,6bS)-Octahydro-cyclobuta[1,2-c;3,4-c']dipyrrole-2-carboxylic Acid Tert-butyl Ester Hydrochloride Hydrogen chloride solution (5-6 M in 2-propanol, 90 µL, 0.45 mmol) was added at 0° C. to a solution of (3aS,3bS,6aR,6bR)-octahydro-cyclobuta[1,2-c;3,4-c']dipyrrole-2,5-dicarboxylic acid di-tert-butyl ester (76 mg, 225 µmol) in ethyl acetate (2 mL). The reaction mixture was stirred at room temperature for 3 days, then the precipitate was collected by filtration and dried to afford the title compound (33 mg, 48%). White solid, MS: 239.6 (M+H)⁺.

Example A

A compound of formula (I) can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula (I) can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:

1. A compound of formula (I)

(I)

wherein:
R¹ is substituted quinolinyl, substituted 1,2,3,4-tetrahydroquinolinyl, substituted isoquinolinyl, substituted 1,2,3,4-tetrahydroisoquinolinyl, substituted 9H-carbazolyl, substituted chromanyl, substituted indolyl, substituted naphthyl, substituted oxazolyl, substituted phenyl, substituted phenylalkyl, substituted phenoxyalkyl, substituted phenylalkoxy, substituted phenylalkenyl, substituted pyridazinyl, substituted pyridinyl, substituted pyridinonyl, substituted tetralinyl or substituted tetralinonyl,
wherein substituted quinolinyl, substituted 1,2,3,4-tetrahydroquinolinyl, substituted isoquinolinyl, substituted 1,2,3,4-tetrahydroisoquinolinyl, substituted 9H-carbazolyl, substituted chromanyl, substituted indolyl, substituted naphthyl, substituted oxazolyl, substituted phenyl, substituted phenylalkyl, substituted phenoxyalkyl, substituted phenylalkoxy, substituted phenylalkenyl, substituted pyridazinyl, substituted pyridinyl, substituted pyridinonyl, substituted tetralinyl and substituted tetralinonyl are substituted with R⁶, R⁷ and R⁸;
Y is —C(O)— or —S(O)₂—;
R² is substituted pyridinyl, substituted phenyl, or is selected from the ring systems A, B and C, wherein substituted pyridinyl and substituted phenyl are substituted with one substituted aminosulfonyl, wherein substituted aminosulfonyl is substituted on the nitrogen atom with one to two substituents independently selected from H, alkyl, cycloalkyl, cycloalkylalkyl, hydroxyalkyl and alkoxyalkyl;

A

B

C

R³, R⁴ and R⁵ are independently selected from H, alkyl, halogen, haloalkyl and alkoxy; and R⁶, R⁷ and R⁸ are independently selected from H, halogen, cyano, cyanoalkyl, alkyl, hydroxyalkyl, haloalkyl, hydroxyhaloalkyl, cycloalkyl, cycloalkylalkyl, cycloalkylalkoxy, cycloalkoxy, cycloalkoxyalkyl, cycloalkylalkoxyalkyl, alkoxy, alkoxyalkyl, haloalkoxy, alkoxyhaloalkyl, alkoxyalkoxy, alkoxyalkoxyalkyl, alkylsulfonyl, furanyl, tetrahydropyranyl, phenyl, substituted phenyl, phenylalkoxy, and substituted phenylalkoxy, wherein substituted phenyl, and substituted phenylalkoxy are substituted with one to three halogen;
or a pharmaceutically acceptable salt thereof.

2. The compound according to claim 1, or a pharmaceutically acceptable salt thereof, wherein R¹ is substituted quinolinyl, substituted indolyl, substituted naphthyl, substituted phenylalkoxy, substituted phenylalkenyl or substituted pyridinyl,
wherein substituted quinolinyl, substituted indolyl, substituted naphthyl, substituted phenylalkoxy, substituted phenylalkenyl and substituted pyridinyl are substituted with R⁶, R⁷ and R⁸.

3. The compound according to claim 1, or a pharmaceutically acceptable salt thereof, wherein R¹ is substituted quinolinyl, substituted indolyl, substituted naphthyl or substituted pyridinyl,
wherein substituted quinolinyl, substituted indolyl, substituted naphthyl and substituted pyridinyl are substituted with R⁶, R⁷ and R⁸.

4. The compound according to claim 1, or a pharmaceutically acceptable salt thereof, wherein R² is selected from the ring systems A and C.

5. The compound according to claim 1, or a pharmaceutically acceptable salt thereof, wherein R² is the ring system A.

6. The compound according to claim 1, or a pharmaceutically acceptable salt thereof, wherein Y is —C(O)—.

7. The compound according to claim 1, or a pharmaceutically acceptable salt thereof, wherein R³, R⁴ and R⁵ are independently selected from H and halogen.

8. The compound according to claim 1, or a pharmaceutically acceptable salt thereof, wherein R³, R⁴ and R⁵ are H.

9. The compound according to claim 1, or a pharmaceutically acceptable salt thereof, wherein R⁶ is H, halogen, cyano, cyanoalkyl, alkyl, haloalkyl, cycloalkylalkoxy, alkoxy, alkoxyalkyl, haloalkoxy, alkoxyalkoxy, phenyl, phenylalkoxy or phenyl substituted with one to three halogen.

10. The compound according to claim 1, or a pharmaceutically acceptable salt thereof, wherein R⁶ is alkoxy, haloalkoxy or alkoxyalkoxy.

11. The compound according to claim 1, or a pharmaceutically acceptable salt thereof, wherein R⁷ is H, halogen, alkyl, cycloalkyl, alkoxy, haloalkoxy, alkylsulfonyl, furanyl or tetrahydropyranyl.

12. The compound according to claim 1, or a pharmaceutically acceptable salt thereof, wherein R⁷ is H or halogen.

13. The compound according to claim 1, or a pharmaceutically acceptable salt thereof, wherein R⁸ is H or alkyl.

14. The compound according to claim 1, or a pharmaceutically acceptable salt thereof, wherein R⁸ is H.

15. The compound according to claim 1, wherein the compound is:
[(3aS,3bS,6aR,6bR)-5-(1H-benzotriazole-5-carbonyl)-octahydro-cyclobuta[1,2-c;3,4-c']dipyrrol-2-yl]-(6-chloro-naphthalen-2-yl)-methanone;

1-[(3aS,3bR,6aS,6bR)-5-(1H-benzotriazole-5-carbonyl)-octahydro-cyclobuta[1,2-c;3,4-c']dipyrrol-2-yl]-3-(4-trifluoromethoxy-phenyl)-propan-1-one;

[(3aS,3bS,6aR,6bR)-5-(1H-benzotriazole-5-carbonyl)-octahydro-cyclobuta[1,2-c;3,4-c']dipyrrol-2-yl]-(4'-fluoro-biphenyl-4-yl)-methanone;

(E)-1-[(3aS,3bR,6aS,6bR)-5-(1H-benzotriazole-5-carbonyl)-octahydro-cyclobuta[1,2-c;3,4-c']dipyrrol-2-yl]-3-(4-trifluoromethoxy-phenyl)-propenone;

[(3aS,3bS,6aR,6bR)-5-(1H-benzotriazole-5-carbonyl)-octahydro-cyclobuta[1,2-c;3,4-c']dipyrrol-2-yl]-(6-bromo-naphthalen-2-yl)-methanone;

[(3aS,3bS,6aR,6bR)-5-(1H-benzotriazole-5-carbonyl)-octahydro-cyclobuta[1,2-c;3,4-c']dipyrrol-2-yl]-(6-methoxy-naphthalen-2-yl)-methanone;

(E)-1-[(3aS,3bS,6aR,6bR)-5-((R)-4,5,6,7-tetrahydro-1H-benzotriazole-5-carbonyl)-octahydro-cyclobuta[1,2-c;3,4-c']dipyrrol-2-yl]-3-(4-trifluoromethoxy-phenyl)-propenone;

6-[(3aS,3bS,6aR,6bR)-5-(1H-benzotriazole-5-carbonyl)-octahydro-cyclobuta[1,2-c;3,4-c']dipyrrole-2-carbonyl]-naphthalene-2-carbonitrile;

1-[(3aR,3bS,6aR,6bS)-5-(1H-benzotriazole-5-carbonyl)-octahydro-cyclobuta[1,2-c;3,4-c']dipyrrol-2-yl]-2-(4-trifluoromethoxy-phenoxy)-ethanone;

1-[(3aR,3bS,6aR,6bS)-5-(1H-benzotriazole-5-carbonyl)-octahydro-cyclobuta[1,2-c;3,4-c']dipyrrol-2-yl]-2-(2-isopropyl-phenoxy)-ethanone;

[(3aR,3bS,6aR,6bS)-5-(1H-benzotriazole-5-carbonyl)-octahydro-cyclobuta[1,2-c;3,4-c']dipyrrol-2-yl]-(5-trifluoromethoxy-1H-indol-2-yl)-methanone;

[(3aR,3bS,6aR,6bS)-5-(1H-benzotriazole-5-carbonyl)-octahydro-cyclobuta[1,2-c;3,4-c']dipyrrol-2-yl]-(6-trifluoromethoxy-1H-indol-2-yl)-methanone;

[(3aS,3bS,6aR,6bR)-5-(1H-benzotriazole-5-carbonyl)-octahydro-cyclobuta[1,2-c;3,4-c']dipyrrol-2-yl]-naphthalen-2-yl-methanone;

[(3aS,3bS,6aR,6bR)-5-(1H-benzotriazole-5-carbonyl)-octahydro-cyclobuta[1,2-c;3,4-c']dipyrrol-2-yl]-(6-methyl-naphthalen-2-yl)-methanone;

[(3aS,3bS,6aR,6bR)-5-(1H-benzotriazole-5-carbonyl)-octahydro-cyclobuta[1,2-c;3,4-c']dipyrrol-2-yl]-(7-methyl-naphthalen-2-yl)-methanone;

[(3aS,3bS,6aR,6bR)-5-(1H-benzotriazole-5-carbonyl)-octahydro-cyclobuta[1,2-c;3,4-c']dipyrrol-2-yl]-(6-phenyl-naphthalen-2-yl)-methanone;

(6-bromo-naphthalen-2-yl)-[(3aR,3bS,6aR,6bS)-5-((R)-4,5,6,7-tetrahydro-1H-benzotriazole-5-carbonyl)-octahydro-cyclobuta[1,2-c;3,4-c']dipyrrol-2-yl]-methanone;

[(3aS,3bS,6aR,6bR)-5-(1H-benzotriazole-5-carbonyl)-octahydro-cyclobuta[1,2-c;3,4-c']dipyrrol-2-yl]-(4'-chloro-biphenyl-4-yl)-methanone;

(4'-chloro-biphenyl-4-yl)-[(3aR,3bS,6aR,6bS)-5-((R)-4,5,6,7-tetrahydro-1H-benzotriazole-5-carbonyl)-octahydro-cyclobuta[1,2-c;3,4-c']dipyrrol-2-yl]-methanone;

[(3aR,3bS,6aR,6bS)-5-((R)-4,5,6,7-tetrahydro-1H-benzotriazole-5-carbonyl)-octahydro-cyclobuta[1,2-c;3,4-c']dipyrrol-2-yl]-(5-trifluoromethoxy-1H-indol-2-yl)-methanone;

[(3aR,3bS,6aR,6bS)-5-((R)-4,5,6,7-tetrahydro-1H-benzotriazole-5-carbonyl)-octahydro-cyclobuta[1,2-c;3,4-c']dipyrrol-2-yl]-(6-trifluoromethoxy-1H-indol-2-yl)-methanone;

[(3aS,3bS,6aR,6bR)-5-(1H-benzotriazole-5-carbonyl)-octahydro-cyclobuta[1,2-c;3,4-c']dipyrrol-2-yl]-(3-methoxy-naphthalen-2-yl)-methanone;

[(3aS,3bS,6aR,6bR)-5-(1H-benzotriazole-5-carbonyl)-octahydro-cyclobuta[1,2-c;3,4-c']dipyrrol-2-yl]-(1-methoxy-naphthalen-2-yl)-methanone;

[(3aR,3bS,6aR,6bS)-5-(1H-benzotriazole-5-carbonyl)-octahydro-cyclobuta[1,2-c;3,4-c']dipyrrol-2-yl]-(1H-indol-2-yl)-methanone;

[(3aR,3bS,6aR,6bS)-5-(1H-benzotriazole-5-carbonyl)-octahydro-cyclobuta[1,2-c;3,4-c']dipyrrol-2-yl]-(1-methyl-1H-indol-2-yl)-methanone;

[(3aS,3bS,6aR,6bR)-5-(1H-benzotriazole-5-carbonyl)-octahydro-cyclobuta[1,2-c;3,4-c']dipyrrol-2-yl]-(4-cyclopropylmethoxy-naphthalen-2-yl)-methanone;

[(3aS,3bS,6aR,6bR)-5-(1H-benzotriazole-5-carbonyl)-octahydro-cyclobuta[1,2-c;3,4-c']dipyrrol-2-yl]-(4-methoxy-naphthalen-2-yl)-methanone;

2-[(3aR,3bS,6aR,6bS)-5-(1H-benzotriazole-5-carbonyl)-octahydro-cyclobuta[1,2-c;3,4-c']dipyrrole-2-carbonyl]-1H-indole-5-carbonitrile;

[(3aS,3bS,6aR,6bR)-5-(1H-benzotriazole-5-carbonyl)-octahydro-cyclobuta[1,2-c;3,4-c']dipyrrol-2-yl]-(3-methoxy-phenyl)-methanone;

[(3aR,3bS,6aR,6bS)-5-(1H-benzotriazole-5-carbonyl)-octahydro-cyclobuta[1,2-c;3,4-c']dipyrrol-2-yl]-(4-methoxy-quinolin-2-yl)-methanone;

[(3aS,3bS,6aR,6bR)-5-(1H-benzotriazole-5-carbonyl)-octahydro-cyclobuta[1,2-c;3,4-c']dipyrrol-2-yl]-[2-(4-chloro-phenyl)-5-methyl-oxazol-4-yl]-methanone;

[(3aS,3bR,6aS,6bR)-5-(1H-benzotriazole-5-carbonyl)-octahydro-cyclobuta[1,2-c;3,4-c']dipyrrol-2-yl]-(1,2,3,4-tetrahydro-naphthalen-2-yl)-methanone;

[(3aR,3bS,6aR,6bS)-5-(1H-benzotriazole-5-carbonyl)-octahydro-cyclobuta[1,2-c;3,4-c']dipyrrol-2-yl]-(1-methyl-5-trifluoromethoxy-1H-indol-2-yl)-methanone;

[(3aR,3bS,6aR,6bS)-5-(1H-benzotriazole-5-carbonyl)-octahydro-cyclobuta[1,2-c;3,4-c']dipyrrol-2-yl]-(6-chloro-1H-indol-2-yl)-methanone;

[(3aR,3bS,6aR,6bS)-5-(1H-benzotriazole-5-carbonyl)-octahydro-cyclobuta[1,2-c;3,4-c']dipyrrol-2-yl]-(6-chloro-1-methyl-1H-indol-2-yl)-methanone;

[(3aR,3bS,6aR,6bS)-5-(1H-benzotriazole-5-carbonyl)-octahydro-cyclobuta[1,2-c;3,4-c']dipyrrol-2-yl]-(6-methyl-1H-indol-2-yl)-methanone;

{2-[(3aR,3bS,6aR,6bS)-5-(1H-benzotriazole-5-carbonyl)-octahydro-cyclobuta[1,2-c;3,4-c']dipyrrole-2-carbonyl]-indol-1-yl}-acetonitrile;

[(3aR,3bS,6aR,6bS)-5-(1H-benzotriazole-5-carbonyl)-octahydro-cyclobuta[1,2-c;3,4-c']dipyrrol-2-yl]-(1-isobutyl-1H-indol-2-yl)-methanone;

[(3aR,3bS,6aR,6bS)-5-(1H-benzotriazole-5-carbonyl)-octahydro-cyclobuta[1,2-c;3,4-c']dipyrrol-2-yl]-quinolin-2-yl-methanone;

[(3aR,3bS,6aR,6bS)-5-(1H-benzotriazole-5-carbonyl)-octahydro-cyclobuta[1,2-c;3,4-c']dipyrrol-2-yl]-isoquinolin-3-yl-methanone;

[(3aS,3bS,6aR,6bR)-5-(1H-benzotriazole-5-carbonyl)-octahydro-cyclobuta[1,2-c;3,4-c']dipyrrol-2-yl]-(1H-indol-6-yl)-methanone;

3-[(3aS,3bR,6aS,6bR)-5-(1H-benzotriazole-5-carbonyl)-octahydro-cyclobuta[1,2-c;3,4-c']dipyrrole-2-carbonyl]-3,4-dihydro-2H-naphthalen-1-one;

[(3aR,3bS,6aR,6bS)-5-(1H-benzotriazole-5-carbonyl)-octahydro-cyclobuta[1,2-c;3,4-c']dipyrrol-2-yl]-chroman-2-yl-methanone;

[(3aS,3bS,6aR,6bR)-5-(1H-benzotriazole-5-carbonyl)-octahydro-cyclobuta[1,2-c;3,4-c']dipyrrol-2-yl]-(1H-indol-5-yl)-methanone;

(4-methoxy-naphthalen-2-yl)-[(3aR,3bS,6aR,6bS)-5-((R)-4,5,6,7-tetrahydro-1H-benzotriazole-5-carbonyl)-octahydro-cyclobuta[1,2-c;3,4-c']dipyrrol-2-yl]-methanone;

[(3aS,3bS,6aR,6bR)-5-(1H-benzotriazole-5-carbonyl)-octahydro-cyclobuta[1,2-c;3,4-c']dipyrrol-2-yl]-[6-(4-chloro-phenyl)-pyridin-3-yl]-methanone;

[(3aR,3bS,6aR,6bS)-5-(1H-benzotriazole-5-carbonyl)-octahydro-cyclobuta[1,2-c;3,4-c']dipyrrol-2-yl]-(1-methoxy-isoquinolin-3-yl)-methanone;

[(3aR,3bS,6aR,6bS)-5-(1H-benzotriazole-5-carbonyl)-octahydro-cyclobuta[1,2-c;3,4-c']dipyrrol-2-yl]-(4-methyl-quinolin-2-yl)-methanone;

[(3aR,3bS,6aR,6bS)-5-(1H-benzotriazole-5-carbonyl)-octahydro-cyclobuta[1,2-c;3,4-c']dipyrrol-2-yl]-(5-chloro-1H-indol-2-yl)-methanone;

[(3aS,3bS,6aR,6bR)-5-(1H-benzotriazole-5-carbonyl)-octahydro-cyclobuta[1,2-c;3,4-c']dipyrrol-2-yl]-[4-(2-methoxy-ethoxy)-naphthalen-2-yl]-methanone;

[(3aS,3bS,6aR,6bR)-5-(1H-benzotriazole-5-carbonyl)-octahydro-cyclobuta[1,2-c;3,4-c']dipyrrol-2-yl]-(7-phenyl-naphthalen-2-yl)-methanone;

[(3aS,3bS,6aR,6bR)-5-(1H-benzotriazole-5-carbonyl)-octahydro-cyclobuta[1,2-c;3,4-c']dipyrrol-2-yl]-(4-ethoxy-naphthalen-2-yl)-methanone;

[(3aS,3bS,6aR,6bR)-5-(1H-benzotriazole-5-carbonyl)-octahydro-cyclobuta[1,2-c;3,4-c']dipyrrol-2-yl]-(4-isopropoxy-naphthalen-2-yl)-methanone;

[(3aS,3bS,6aR,6bR)-5-(1H-benzotriazole-5-carbonyl)-octahydro-cyclobuta[1,2-c;3,4-c']dipyrrol-2-yl]-(4-benzyloxy-1H-indol-6-yl)-methanone;

[(3aS,3bS,6aR,6bR)-5-(1H-benzotriazole-5-carbonyl)-octahydro-cyclobuta[1,2-c;3,4-c']dipyrrol-2-yl]-(5,6,7,8-tetrahydro-naphthalen-2-yl)-methanone;

[(3aS,3bR,6aS,6bR)-5-(1H-benzotriazole-5-carbonyl)-octahydro-cyclobuta[1,2-c;3,4-c']dipyrrol-2-yl]-(4,4-dimethyl-1,2,3,4-tetrahydro-naphthalen-2-yl)-methanone;

[(3aS,3bR,6aS,6bR)-5-(1H-benzotriazole-5-carbonyl)-octahydro-cyclobuta[1,2-c;3,4-c']dipyrrol-2-yl]-[1-(3-methoxy-propyl)-1,2,3,4-tetrahydro-quinolin-3-yl]-methanone;

[(3aR,3bS,6aR,6bS)-5-(1H-benzotriazole-5-carbonyl)-octahydro-cyclobuta[1,2-c;3,4-c']dipyrrol-2-yl]-[1-(2-methoxy-ethoxy)-isoquinolin-3-yl]-methanone;

[(3aR,3bS,6aR,6bS)-5-(1H-benzotriazole-5-carbonyl)-octahydro-cyclobuta[1,2-c;3,4-c']dipyrrol-2-yl]-(1-cyclopropylmethoxy-isoquinolin-3-yl)-methanone;

(4-isopropoxy-naphthalen-2-yl)-[(3aR,3bS,6aR,6bS)-5-((R)-4,5,6,7-tetrahydro-1H-benzotriazole-5-carbonyl)-octahydro-cyclobuta[1,2-c;3,4-c']dipyrrol-2-yl]-methanone;

[(3aR,3bS,6aR,6bS)-5-(1H-benzotriazole-5-carbonyl)-octahydro-cyclobuta[1,2-c;3,4-c']dipyrrol-2-yl]-[1-(2,2,2-trifluoro-ethoxy)-isoquinolin-3-yl]-methanone;

[(3aS,3bS,6aR,6bR)-5-(1H-benzotriazole-5-carbonyl)-octahydro-cyclobuta[1,2-c;3,4-c']dipyrrol-2-yl]-(4-isopropoxy-1H-indol-6-yl)-methanone;

4-[(3aS,3bS,6aR,6bR)-5-(4-isopropoxy-naphthalene-2-carbonyl)-octahydro-cyclobuta[1,2-c;3,4-c']dipyrrole-2-carbonyl]-benzenesulfonamide;

[6-(4-chloro-phenyl)-pyridin-3-yl]-[(3aR,3bS,6aR,6bS)-5-((R)-4,5,6,7-tetrahydro-1H-benzotriazole-5-carbonyl)-octahydro-cyclobuta[1,2-c;3,4-c']dipyrrol-2-yl]-methanone;

(1-cyclopropylmethoxy-isoquinolin-3-yl)-[(3aR,3bS,6aR,6bS)-5-((R)-4,5,6,7-tetrahydro-1H-benzotriazole-5-carbonyl)-octahydro-cyclobuta[1,2-c;3,4-c']dipyrrol-2-yl]-methanone;

[(3aS,3bS,6aR,6bR)-5-(1H-benzotriazole-5-carbonyl)-octahydro-cyclobuta[1,2-c;3,4-c']dipyrrol-2-yl]-(4-isopropoxy-1-methyl-1H-indol-6-yl)-methanone;

[(3aR,3bS,6aR,6bS)-5-(1H-benzotriazole-5-carbonyl)-octahydro-cyclobuta[1,2-c;3,4-c']dipyrrol-2-yl]-(4-ethoxy-quinolin-2-yl)-methanone;

[(3aR,3bS,6aR,6bS)-5-(1H-benzotriazole-5-carbonyl)-octahydro-cyclobuta[1,2-c;3,4-c']dipyrrol-2-yl]-(4-isopropoxy-quinolin-2-yl)-methanone;

[(3aS,3bS,6aR,6bR)-5-(1H-benzotriazole-5-carbonyl)-octahydro-cyclobuta[1,2-c;3,4-c']dipyrrol-2-yl]-(6-chloro-9H-carbazol-2-yl)-methanone;

[(3aR,3bS,6aR,6bS)-5-(1H-benzotriazole-5-carbonyl)-octahydro-cyclobuta[1,2-c;3,4-c']dipyrrol-2-yl]-[4-(2-methoxy-ethoxy)-quinolin-2-yl]-methanone;

[(3aR,3bS,6aR,6bS)-5-(1H-benzotriazole-5-carbonyl)-octahydro-cyclobuta[1,2-c;3,4-c']dipyrrol-2-yl]-(4-isopropoxy-7-trifluoromethyl-quinolin-2-yl)-methanone;

[(3aR,3bS,6aR,6bS)-5-(1H-benzotriazole-5-carbonyl)-octahydro-cyclobuta[1,2-c;3,4-c']dipyrrol-2-yl]-(4-cyclopropylmethoxy-quinolin-2-yl)-methanone;

[(3aR,3bS,6aR,6bS)-5-(1H-benzotriazole-5-carbonyl)-octahydro-cyclobuta[1,2-c;3,4-c']dipyrrol-2-yl]-[5-(4-chloro-phenyl)-pyridin-2-yl]-methanone;

[(3aR,3bS,6aR,6bS)-5-(1H-benzotriazole-5-carbonyl)-octahydro-cyclobuta[1,2-c;3,4-c']dipyrrol-2-yl]-(1-ethoxy-isoquinolin-3-yl)-methanone;

[(3aS,3bS,6aR,6bR)-5-(1H-benzotriazole-5-carbonyl)-octahydro-cyclobuta[1,2-c;3,4-c']dipyrrol-2-yl]-(1-ethyl-4-isopropoxy-1H-indol-6-yl)-methanone;

6-[(3aR,3bS,6aR,6bS)-5-(1H-benzotriazole-5-carbonyl)-octahydro-cyclobuta[1,2-c;3,4-c']dipyrrole-2-carbonyl]-3-(4-chloro-phenyl)-1H-pyridin-2-one;

1-[(3aR,3bS,6aR,6bS)-5-(1H-benzotriazole-5-carbonyl)-octahydro-cyclobuta[1,2-c;3,4-c']dipyrrol-2-yl]-(7-chloro-4-ethoxy-quinolin-2-yl)-methanone;

(7-chloro-4-ethoxy-quinolin-2-yl)-[(3aR,3bS,6aR,6bS)-5-((R)-4,5,6,7-tetrahydro-1H-benzotriazole-5-carbonyl)-octahydro-cyclobuta[1,2-c;3,4-c']dipyrrol-2-yl]methanone;

[(3aS,3bS,6aR,6bR)-5-(1H-benzotriazole-5-carbonyl)-octahydro-cyclobuta[1,2-c;3,4-c']dipyrrol-2-yl]-(4-isopropoxy-5,6,7,8-tetrahydro-naphthalen-2-yl)-methanone;

(1H-benzotriazol-5-yl)-{(3aS,3bR,6aS,6bR)-5-[4-(2-methoxy-ethoxy)-7-trifluoromethyl-quinoline-2-carbonyl]-octahydro-cyclobuta[1,2-c;3,4-c']dipyrrol-2-yl}-methanone;

(1H-benzotriazol-5-yl)-[(3aS,3bR,6aS,6bR)-5-(4-ethoxy-6-trifluoromethyl-quinoline-2-carbonyl)-octahydro-cyclobuta[1,2-c;3,4-c']dipyrrol-2-yl]-methanone;

[(3aS,3bS,6aR,6bR)-5-(1H-benzotriazole-5-carbonyl)-octahydro-cyclobuta[1,2-c;3,4-c']dipyrrol-2-yl]-(4-ethoxy-1-ethyl-1H-indol-5-yl)-methanone;

[(3aS,3bS,6aR,6bR)-5-(1H-benzotriazole-5-carbonyl)-octahydro-cyclobuta[1,2-c;3,4-c']dipyrrol-2-yl]-[1-ethyl-4-(2,2,2-trifluoro-ethoxy)-1H-indol-5-yl]-methanone;

5-[(3aS,3bR,6aS,6bR)-5-(4-ethoxy-quinoline-2-carbonyl)-octahydro-cyclobuta[1,2-c;3,4-c']dipyrrole-2-carbonyl]-pyridine-2-sulfonic acid amide;

(1H-benzotriazol-5-yl)-{(3aS,3bR,6aS,6bR)-5-[4-(2,2,2-trifluoro-ethoxy)-quinoline-2-carbonyl]-octahydro-cyclobuta[1,2-c;3,4-c']dipyrrol-2-yl}-methanone;

(1H-benzotriazol-5-yl)-{(3aS,3bS,6aR,6bR)-5-[4-ethoxy-1-(2,2,2-trifluoro-ethyl)-1H-indole-6-carbonyl]-octahydro-cyclobuta[1,2-c;3,4-c']dipyrrol-2-yl}-methanone;

(1H-benzotriazol-5-yl)-[(3aS,3bR,6aS,6bR)-5-(5-chloro-4-cyclopropylmethoxy-pyridine-2-carbonyl)-octahydro-cyclobuta[1,2-c;3,4-c']dipyrrol-2-yl]-methanone;

(1H-benzotriazol-5-yl)-[(3aS,3bR,6aS,6bR)-5-(5-cyclopropyl-6-cyclopropylmethoxy-pyridine-2-carbonyl)-octahydro-cyclobuta[1,2-c;3,4-c']dipyrrol-2-yl]-methanone;

(3,4-dimethyl-phenyl)-[(3aS,3bR,6aS,6bR)-5-(4-ethoxy-5,6,7,8-tetrahydro-quinoline-2-carbonyl)-octahydro-cyclobuta[1,2-c;3,4-c']dipyrrol-2-yl]-methanone;

(1H-benzotriazol-5-yl)-[(3aS,3bS,6aR,6bR)-5-(4'-chloro-biphenyl-3-carbonyl)-octahydro-cyclobuta[1,2-c;3,4-c']dipyrrol-2-yl]-methanone;

(1H-benzotriazol-5-yl)-[(3aS,3bR,6aS,6bR)-5-(4-ethoxy-7-methoxy-quinoline-2-carbonyl)-octahydro-cyclobuta[1,2-c;3,4-c']dipyrrol-2-yl]-methanone;

[(3aS,3bS,6aR,6bR)-5-(4-Ethoxy-6-trifluoromethyl-quinoline-2-carbonyl)-octahydro-cyclobuta[1,2-c;3,4-c']dipyrrol-2-yl]-(1H-[1,2,3]triazolo[4,5-b]pyridin-5-yl)-methanone;

[(3aS,3bS,6aR,6bR)-5-(1-ethoxy-isoquinoline-3-carbonyl)-octahydro-cyclobuta[1,2-c;3,4-c']dipyrrol-2-yl]-(1H-[1,2,3]triazolo[4,5-b]pyridin-5-yl)-methanone;

(1H-benzotriazol-5-yl)-[(3aS,3bR,6aS,6bR)-5-(6-cyclopropylmethoxy-5-trifluoromethyl-pyridine-2-carbonyl)-octahydro-cyclobuta[1,2-c;3,4-c']dipyrrol-2-yl]-methanone;

(1H-benzotriazol-5-yl)-{(3aS,3bR,6aS,6bR)-5-[5-cyclopropyl-4-(2,2,2-trifluoro-ethoxy)-pyridine-2-carbonyl]-octahydro-cyclobuta[1,2-c;3,4-c']dipyrrol-2-yl}-methanone;

(1H-benzotriazol-5-yl)-{(3aS,3bR,6aS,6bR)-5-[6-cyclopropyl-5-(2,2,2-trifluoro-ethoxy)-pyridazine-3-carbonyl]-octahydro-cyclobuta[1,2-c;3,4-c']dipyrrol-2-yl]-methanone'}dipyrrol-2-yl}-methanone;

[(3aR,3bS,6aR,6bS)-5-(1H-benzotriazole-5-carbonyl)-octahydro-cyclobuta[1,2-c;3,4-c']dipyrrol-2-yl]-(6-chloro-4-ethoxy-quinolin-2-yl)-methanone;

(1H-benzotriazol-5-yl)-{(3aS,3bR,6aS,6bR)-5-[6-(2,2,2-trifluoro-ethoxy)-5-trifluoromethyl-pyridine-2-carbonyl]-octahydro-cyclobuta[1,2-c;3,4-c']dipyrrol-2-yl}-methanone;

(1H-benzotriazol-5-yl)-{(3aS,3bR,6aS,6bR)-5-[6-(2,2,2-trifluoro-ethoxy)-pyridine-2-carbonyl]-octahydro-cyclobuta[1,2-c;3,4-c']dipyrrol-2-yl}-methanone;

(1H-benzotriazol-5-yl)-{(3aS,3bS,6aR,6bR)-5-[6-(2,2,2-trifluoro-ethoxy)-pyridine-3-carbonyl]-octahydro-cyclobuta[1,2-c;3,4-c']dipyrrol-2-yl}-methanone;

(1H-benzotriazol-5-yl)-{(3aS,3bS,6aR,6bR)-5-[5-bromo-6-(2,2,2-trifluoro-ethoxy)-pyridine-3-carbonyl]-octahydro-cyclobuta[1,2-c;3,4-c']dipyrrol-2-yl}-methanone;

(1H-benzotriazol-5-yl)-{(3aS,3bR,6aS,6bR)-5-[5-(2,2,2-trifluoro-ethoxy)-pyridine-2-carbonyl]-octahydro-cyclobuta[1,2-c;3,4-c']dipyrrol-2-yl}-methanone;

[(3aS,3bR,6aS,6bR)-5-(6-cyclopropylmethoxy-pyridazine-3-carbonyl)-octahydro-cyclobuta[1,2-c;3,4-c']dipyrrol-2-yl]-(3,4-dimethyl-phenyl)-methanone;

(1H-benzotriazol-5-yl)-{(3aS,3bS,6aR,6bR)-5-[5-bromo-2-methyl-6-(2,2,2-trifluoro-ethoxy)-pyridine-3-carbonyl]-octahydro-cyclobuta[1,2-c;3,4-c']dipyrrol-2-yl}-methanone;

(1H-benzotriazol-5-yl)-{(3aS,3bS,6aR,6bR)-5-[5-cyclopropyl-6-(2,2,2-trifluoro-ethoxy)-pyridine-3-carbonyl]-octahydro-cyclobuta[1,2-c;3,4-c']dipyrrol-2-yl}-methanone;

(1H-benzotriazol-5-yl)-{(3aS,3bS,6aR,6bR)-5-[6-(2,2,2-trifluoro-ethoxy)-5-trifluoromethyl-pyridine-3-carbonyl]-octahydro-cyclobuta[1,2-c;3,4-c']dipyrrol-2-yl}-methanone;

(1H-benzotriazol-5-yl)-{(3aS,3bS,6aR,6bR)-5-[5-(tetrahydro-pyran-4-yl)-6-(2,2,2-trifluoro-ethoxy)-pyridine-3-carbonyl]-octahydro-cyclobuta[1,2-c;3,4-c']dipyrrol-2-yl}-methanone;

(1H-benzotriazol-5-yl)-{(3aS,3bR,6aS,6bR)-5-[4-(4-chloro-phenyl)-5-(2,2,2-trifluoro-ethoxy)-pyridine-2-carbonyl]-octahydro-cyclobuta[1,2-c;3,4-c']dipyrrol-2-yl}-methanone;

(1H-benzotriazol-5-yl)-{(3aS,3bS,6aR,6bR)-5-[5-furan-2-yl-6-(2,2,2-trifluoro-ethoxy)-pyridine-3-carbonyl]-octahydro-cyclobuta[1,2-c;3,4-c']dipyrrol-2-yl}-methanone;

(1H-benzotriazol-5-yl)-{(3aS,3bS,6aR,6bR)-5-[5-chloro-6-(2,2,2-trifluoro-ethoxy)-pyridine-3-carbonyl]-octahydro-cyclobuta[1,2-c;3,4-c']dipyrrol-2-yl}-methanone;

[(3aS,3bR,6aS,6bR)-5-(4-ethoxy-quinoline-2-carbonyl)-octahydro-cyclobuta[1,2-c;3,4-c']dipyrrol-2-yl]-(4-fluoro-1H-benzotriazol-5-yl)-methanone;

{(3aS,3bS,6aR,6bR)-5-[5-methanesulfonyl-6-(2,2,2-trifluoro-ethoxy)-pyridine-3-carbonyl]-octahydro-cyclobuta[1,2-c;3,4-c']dipyrrol-2-yl}-phenyl-methanone;

(3aR,3bS,6aR,6bS)-5-(1H-benzotriazole-5-carbonyl)-octahydro-cyclobuta[1,2-c;3,4-c']dipyrrole-2-carboxylicacid 4-trifluoromethoxy-benzyl ester;

(3aR,3bS,6aR,6bS)-5-(1H-benzotriazole-5-carbonyl)-octahydro-cyclobuta[1,2-c;3,4-c']dipyrrole-2-carboxylic acid 3,5-dichloro-benzyl ester;

(1H-benzotriazol-5-yl)-[(3aS,3bR,6aS,6bR)-5-(4'-fluoro-biphenyl-4-sulfonyl)-octahydro-cyclobuta[1,2-c;3,4-c']dipyrrol-2-yl]-methanone;

(1H-benzotriazol-5-yl)-[(3aS,3bR,6aS,6bR)-5-(6-chloro-naphthalene-2-sulfonyl)-octahydro-cyclobuta[1,2-c;3,4-c']dipyrrol-2-yl]-methanone; or

[(3aR,3bS,6aR,6bS)-5-(1H-benzotriazole-5-carbonyl)-octahydro-cyclobuta[1,2-c;3,4-c']dipyrrol-2-yl]-(6-trifluoromethyl-3,4-dihydro-1H-isoquinolin-2-yl)-methanone;

or a pharmaceutically acceptable salts thereof.

16. The compound according claim 1, wherein the compound is:

(E)-1-[(3aS,3bR,6aS,6bR)-5-(1H-benzotriazole-5-carbonyl)-octahydro-cyclobuta[1,2-c;3,4-c']dipyrrol-2-yl]-3-(4-trifluoromethoxy-phenyl)-propenone;

(4-isopropoxy-naphthalen-2-yl)-[(3aR,3bS,6aR,6bS)-5-((R)-4,5,6,7-tetrahydro-1H-benzotriazole-5-carbonyl)-octahydro-cyclobuta[1,2-c;3,4-c']dipyrrol-2-yl]-methanone;

4-[(3aS,3bS,6aR,6bR)-5-(4-isopropoxy-naphthalene-2-carbonyl)-octahydro-cyclobuta[1,2-c;3,4-c']dipyrrole-2-carbonyl]-benzenesulfonamide;

[(3aS,3bS,6aR,6bR)-5-(1H-benzotriazole-5-carbonyl)-octahydro-cyclobuta[1,2-c;3,4-c']dipyrrol-2-yl]-(4-isopropoxy-1-methyl-1H-indol-6-yl)-methanone;

[(3aR,3bS,6aR,6bS)-5-(1H-benzotriazole-5-carbonyl)-octahydro-cyclobuta[1,2-c;3,4-c']dipyrrol-2-yl]-[4-(2-methoxy-ethoxy)-quinolin-2-yl]-methanone;

(1H-benzotriazol-5-yl)-{(3aS,3bS,6aR,6bR)-5-[5-bromo-6-(2,2,2-trifluoro-ethoxy)-pyridine-3-carbonyl]-octahydro-cyclobuta[1,2-c;3,4-c']dipyrrol-2-yl}-methanone; or (3aR,3bS,6aR,6bS)-5-(1H-benzotriazole-5-carbonyl)-octahydro-cyclobuta[1,2-c;3,4-c']dipyrrole-2-carboxylicacid 4-trifluoromethoxy-benzyl ester;

or a pharmaceutically acceptable salt thereof.

17. A pharmaceutical composition, comprising a compound according to claim 1, or a pharmaceutically acceptable salt thereof, and a therapeutically inert carrier.

18. A pharmaceutical composition, comprising a compound according to claim 15, or a pharmaceutically acceptable salt thereof, and a therapeutically inert carrier.

19. A pharmaceutical composition, comprising a compound according to claim 16, or a pharmaceutically acceptable salt thereof, and a therapeutically inert carrier.

20. The compound of claim 1, wherein the compound is:

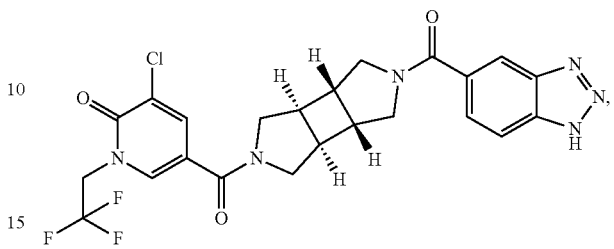

or a pharmaceutically acceptable salt thereof.

* * * * *